US011808677B2

(12) United States Patent
Lee et al.

(10) Patent No.: US 11,808,677 B2
(45) Date of Patent: Nov. 7, 2023

(54) POLYMERASE CHAIN REACTION PATCH, METHOD AND DEVICE FOR DIAGNOSIS USING THE SAME

(71) Applicant: NOUL CO., LTD., Gyeonggi-do (KR)

(72) Inventors: Dong Young Lee, Gyeonggi-do (KR); Chan Yang Lim, Gyeonggi-do (KR); Kyung Hwan Kim, Gyeonggi-do (KR)

(73) Assignee: NOUL CO., LTD., Gyeonggi-do (KR)

(*) Notice: Subject to any disclaimer, the term of this patent is extended or adjusted under 35 U.S.C. 154(b) by 802 days.

(21) Appl. No.: 16/079,360

(22) PCT Filed: Feb. 23, 2017

(86) PCT No.: PCT/KR2017/002026
§ 371 (c)(1),
(2) Date: Aug. 23, 2018

(87) PCT Pub. No.: WO2017/146502
PCT Pub. Date: Aug. 31, 2017

(65) Prior Publication Data
US 2019/0048395 A1    Feb. 14, 2019

Related U.S. Application Data

(60) Provisional application No. 62/298,959, filed on Feb. 23, 2016.

(30) Foreign Application Priority Data

| Jun. 4, 2016 | (KR) | 10-2016-0069936 |
| Jun. 4, 2016 | (KR) | 10-2016-0069937 |
| Jun. 4, 2016 | (KR) | 10-2016-0069938 |
| Jul. 27, 2016 | (KR) | 10-2016-0095739 |
| Sep. 13, 2016 | (KR) | 10-2016-0118462 |
| Nov. 1, 2016 | (KR) | 10-2016-0144551 |
| Feb. 23, 2017 | (KR) | 10-2017-0024387 |

(51) Int. Cl.
| G01N 1/30 | (2006.01) |
| G01N 1/31 | (2006.01) |
| C12Q 1/6844 | (2018.01) |
| C12Q 1/6848 | (2018.01) |
| G01N 33/50 | (2006.01) |
| G01N 21/77 | (2006.01) |
| B01L 3/00 | (2006.01) |
| G01N 15/06 | (2006.01) |
| G01N 33/52 | (2006.01) |
| G01N 33/574 | (2006.01) |
| G01N 15/14 | (2006.01) |
| G01N 33/49 | (2006.01) |
| G01N 33/60 | (2006.01) |
| C12Q 1/686 | (2018.01) |
| C07K 16/30 | (2006.01) |

(Continued)

(52) U.S. Cl.
CPC ............... *G01N 1/312* (2013.01); *B01L 3/00* (2013.01); *C07K 16/3061* (2013.01); *C12Q 1/686* (2013.01); *C12Q 1/6844* (2013.01); *C12Q 1/6848* (2013.01); *C12Q 1/701* (2013.01); *G01N 1/30* (2013.01); *G01N 1/31* (2013.01); *G01N 15/06* (2013.01); *G01N 15/14* (2013.01); *G01N 21/77* (2013.01); *G01N 33/4833* (2013.01); *G01N 33/49* (2013.01); *G01N 33/5082* (2013.01); *G01N 33/52* (2013.01); *G01N 33/533* (2013.01); *G01N 33/5304* (2013.01); *G01N 33/574* (2013.01); *G01N 33/60* (2013.01); *G06T 7/0012* (2013.01); *G06T 7/0014* (2013.01); *B01L 3/505* (2013.01); *B01L 7/52* (2013.01); *G01N 2001/302* (2013.01); *G01N 2015/0065* (2013.01); *G01N 2015/0693* (2013.01); *G01N 2021/7723* (2013.01); *G01N 2021/7786* (2013.01)

(58) Field of Classification Search
None
See application file for complete search history.

(56) References Cited

U.S. PATENT DOCUMENTS 555,270 A    2/1896  Taylor
3,870,146 A    3/1975  Greenfield et al.
(Continued)

FOREIGN PATENT DOCUMENTS

CN    1034617 A    8/1989
CN    1207171 A    2/1999
(Continued)

OTHER PUBLICATIONS

Kim et al. A disposable, self-contained lab chip. vol. 9(4) p. 606-612, Auther manuscript, p. 1-16, 2009.*
(Continued)

*Primary Examiner* — Teresa E Strzelecka
*Assistant Examiner* — Olayinka A Oyeyemi
(74) *Attorney, Agent, or Firm* — KILPATRICK TOWNSEND & STOCKTON LLP

(57) ABSTRACT

According to an aspect of the present disclosure, there is provided a polymerase chain reaction (PCR) patch which is provided as a gel type having a net-like structure forming micro-cavities, wherein at least a part of a plurality of reagents used in a PCR are contained in the micro-cavities, and when the patch contacts with an external region, the reagents contained in the micro-cavities move to at least a portion of the external region, and a PCR of a target DNA included in a sample located in the external region is performed.

9 Claims, 67 Drawing Sheets

(51) Int. Cl.
  *C12Q 1/70* (2006.01)
  *G01N 33/483* (2006.01)
  *G06T 7/00* (2017.01)
  *G01N 33/53* (2006.01)
  *G01N 33/533* (2006.01)
  *B01L 7/00* (2006.01)
  *G01N 15/00* (2006.01)

(56) References Cited

U.S. PATENT DOCUMENTS

| | | |
|---|---|---|
| 4,250,257 A | 2/1981 | Lee et al. |
| 4,839,297 A | 6/1989 | Freitag et al. |
| 4,938,593 A | 7/1990 | Morris et al. |
| 5,143,714 A | 9/1992 | Cosgrove et al. |
| 5,552,270 A | 9/1996 | Khrapko et al. |
| 5,552,279 A | 9/1996 | Weisburg et al. |
| 5,776,684 A | 7/1998 | Chirikjian et al. |
| 5,779,982 A | 7/1998 | Aota et al. |
| 5,928,879 A | 7/1999 | Dumler et al. |
| 6,063,029 A | 5/2000 | Saita et al. |
| 6,174,683 B1 | 1/2001 | Hahn et al. |
| 7,183,356 B2 | 2/2007 | Ishida |
| 7,261,800 B1 | 8/2007 | Nakazato |
| 7,522,757 B2 | 4/2009 | Tsipouras et al. |
| 7,767,414 B1 | 8/2010 | Smith et al. |
| 8,293,487 B1 | 10/2012 | Zhang |
| 8,305,579 B2 | 11/2012 | Treynor et al. |
| 8,409,849 B2 | 4/2013 | Yamasaki |
| 8,597,574 B2 | 12/2013 | Gumbrecht et al. |
| 8,628,787 B2 | 1/2014 | Soldani et al. |
| 8,809,027 B1 | 8/2014 | Lynch et al. |
| 8,936,912 B2 | 1/2015 | Mitra et al. |
| 10,234,447 B2 | 3/2019 | Manaresi et al. |
| 10,254,286 B2 | 4/2019 | Pirie-Shepherd et al. |
| 10,345,204 B2 | 7/2019 | Lee et al. |
| 10,371,610 B2 | 8/2019 | Lee et al. |
| 11,041,842 B2 | 6/2021 | Lee et al. |
| 2002/0055126 A1 | 5/2002 | Schaffler et al. |
| 2003/0083294 A1 | 5/2003 | Sullenger et al. |
| 2003/0124619 A1 | 7/2003 | Weigl et al. |
| 2003/0211507 A1 | 11/2003 | Hatch et al. |
| 2004/0038306 A1 | 2/2004 | Agnew et al. |
| 2004/0126826 A1 | 7/2004 | Yusuf et al. |
| 2004/0175710 A1 | 9/2004 | Haushalter |
| 2005/0139511 A1 | 6/2005 | Burns et al. |
| 2005/0175987 A1 | 8/2005 | Jansen et al. |
| 2005/0175997 A1 | 8/2005 | Ono et al. |
| 2005/0202567 A1 | 9/2005 | Zanzucchi et al. |
| 2005/0244976 A1 | 11/2005 | Gee et al. |
| 2006/0088847 A1 | 4/2006 | Gu et al. |
| 2006/0111331 A1 | 5/2006 | Eishingdrelo et al. |
| 2006/0115905 A1 | 6/2006 | Hatch et al. |
| 2006/0121474 A1 | 6/2006 | Kim et al. |
| 2006/0172278 A1 | 8/2006 | Bonner et al. |
| 2007/0051630 A1 | 3/2007 | Larsson et al. |
| 2007/0087362 A1* | 4/2007 | Church .............. C12N 15/1093 506/4 |
| 2007/0117177 A1 | 5/2007 | Luo et al. |
| 2007/0128073 A1 | 6/2007 | Tappen |
| 2007/0224701 A1 | 9/2007 | Rosenstein |
| 2008/0090267 A1 | 4/2008 | Komatsu et al. |
| 2008/0138842 A1 | 6/2008 | Boehringer et al. |
| 2008/0166745 A1 | 7/2008 | Khan et al. |
| 2008/0182287 A1 | 7/2008 | Smith et al. |
| 2009/0098165 A1 | 4/2009 | Arulanandam et al. |
| 2009/0220968 A1 | 9/2009 | Issadore et al. |
| 2009/0226911 A1* | 9/2009 | Mauk ..................... G01N 31/20 435/6.11 |
| 2010/0047790 A1 | 2/2010 | Southern et al. |
| 2010/0168390 A1 | 7/2010 | Brix et al. |
| 2011/0041978 A1 | 2/2011 | Wallace et al. |
| 2011/0070606 A1 | 3/2011 | Winkelman et al. |
| 2011/0257666 A1 | 10/2011 | Ladet et al. |
| 2012/0040397 A1 | 2/2012 | Luo et al. |
| 2012/0064041 A1 | 3/2012 | Alexanian |
| 2012/0171290 A1 | 7/2012 | Coursaget et al. |
| 2013/0213811 A1 | 8/2013 | Kennedy et al. |
| 2013/0288273 A1 | 10/2013 | Takagi et al. |
| 2013/0296761 A1 | 11/2013 | Goto et al. |
| 2013/0338016 A1 | 12/2013 | McDonough et al. |
| 2014/0004527 A1 | 1/2014 | Oka et al. |
| 2014/0038230 A1 | 2/2014 | Beck et al. |
| 2014/0073063 A1 | 3/2014 | Lieber et al. |
| 2014/0242607 A1 | 8/2014 | Sogabe et al. |
| 2014/0273088 A1 | 9/2014 | Winther |
| 2015/0080252 A1 | 3/2015 | Godwin et al. |
| 2015/0139511 A1 | 5/2015 | Yoon et al. |
| 2016/0265028 A1 | 9/2016 | Kim et al. |
| 2019/0025281 A1 | 1/2019 | Lee et al. |
| 2019/0049349 A1 | 2/2019 | Lee et al. |
| 2019/0049426 A1 | 2/2019 | Lee et al. |
| 2019/0056296 A1 | 2/2019 | Lee et al. |
| 2019/0056298 A1 | 2/2019 | Lee et al. |
| 2019/0064140 A1 | 2/2019 | Lee et al. |
| 2019/0316995 A1 | 10/2019 | Lee et al. |
| 2020/0011772 A1 | 1/2020 | Lee et al. |
| 2020/0240882 A1 | 7/2020 | Lee et al. |
| 2020/0249134 A1 | 8/2020 | Lee et al. |

FOREIGN PATENT DOCUMENTS

| | | |
|---|---|---|
| CN | 1363006 A | 8/2002 |
| CN | 1409110 A | 4/2003 |
| CN | 1561202 A | 1/2005 |
| CN | 1747703 A | 3/2006 |
| CN | 1971276 A | 5/2007 |
| CN | 101004377 A | 7/2007 |
| CN | 101225430 A | 7/2008 |
| CN | 101464237 A | 6/2009 |
| CN | 101598731 A | 12/2009 |
| CN | 101610847 A | 12/2009 |
| CN | 102245305 A | 11/2011 |
| CN | 102245755 A | 11/2011 |
| CN | 102272595 A | 12/2011 |
| CN | 102665917 A | 9/2012 |
| CN | 103038639 A | 4/2013 |
| CN | 103261872 A | 8/2013 |
| CN | 103328651 A | 9/2013 |
| CN | 103800040 A | 5/2014 |
| CN | 103808551 A | 5/2014 |
| CN | 104271191 A | 1/2015 |
| CN | 104349769 A | 2/2015 |
| CN | 104651473 A | 5/2015 |
| CN | 105122034 A | 12/2015 |
| CN | 105136795 A | 12/2015 |
| CN | 105259095 A | 1/2016 |
| EP | 2072993 A2 | 6/2009 |
| EP | 2072993 A3 | 6/2009 |
| EP | 2206462 A1 | 4/2010 |
| EP | 2940474 A1 | 11/2015 |
| JP | S 63-281050 A | 11/1988 |
| JP | H 08-271390 A | 10/1996 |
| JP | S 52-89375 A | 7/1997 |
| JP | 2003344394 A | 12/2003 |
| JP | 2004077387 A | 3/2004 |
| JP | 2008518662 A | 6/2008 |
| JP | 2008164520 A | 7/2008 |
| JP | 2009518651 A | 5/2009 |
| JP | 2012515931 A | 7/2012 |
| JP | 5198399 B2 | 5/2013 |
| JP | 2013515235 A | 5/2013 |
| JP | 2013515955 A | 5/2013 |
| KR | 10-0601831 B1 | 7/2006 |
| KR | 10-2006-0112258 A | 10/2006 |
| KR | 10-2011-0084636 A | 7/2011 |
| KR | 10-2011-0136782 A | 12/2011 |
| KR | 10-2013-0138153 A | 12/2013 |
| KR | 10-2014-0082757 A | 7/2014 |
| KR | 10-2014-0100580 A | 8/2014 |
| KR | 10-2014-0103350 A | 8/2014 |
| KR | 10-1453796 B1 | 10/2014 |
| KR | 10-2015-0048964 A | 5/2015 |
| KR | 10-1540845 B1 | 7/2015 |

(56) References Cited

FOREIGN PATENT DOCUMENTS

| WO | WO-9617083 A1 * | 6/1996 | ............ C12N 11/04 |
|---|---|---|---|
| WO | WO 2000077293 A1 | 12/2000 | |
| WO | WO 2002072081 A1 | 9/2002 | |
| WO | WO 2004024955 A1 | 3/2004 | |
| WO | WO 2004071469 A2 | 8/2004 | |
| WO | WO 2004071469 A3 | 8/2004 | |
| WO | WO 2006050032 A2 | 5/2006 | |
| WO | WO 2006050032 A3 | 5/2006 | |
| WO | WO 2006053770 A1 | 5/2006 | |
| WO | WO 2006108087 A2 | 10/2006 | |
| WO | WO 2006108087 A3 | 10/2006 | |
| WO | WO 2007067847 A2 | 6/2007 | |
| WO | WO 2007067847 A3 | 6/2007 | |
| WO | WO 2008075086 A1 | 6/2008 | |
| WO | WO 2010039627 A2 | 4/2010 | |
| WO | WO 2010039627 A3 | 4/2010 | |
| WO | WO 2010041088 A1 | 4/2010 | |
| WO | WO 2010052543 A1 | 5/2010 | |
| WO | WO 2010052543 A8 | 5/2010 | |
| WO | WO 2010082820 A2 | 7/2010 | |
| WO | WO 2010082820 A3 | 7/2010 | |
| WO | WO 2011066449 A1 | 6/2011 | |
| WO | WO 2011076705 A1 | 6/2011 | |
| WO | WO 2011080539 A1 | 7/2011 | |
| WO | WO 2011143075 A2 | 11/2011 | |
| WO | WO 2011143075 A3 | 11/2011 | |
| WO | WO 2012003579 A1 | 1/2012 | |
| WO | WO 2012030313 A1 | 3/2012 | |
| WO | WO 2012048154 A1 | 4/2012 | |
| WO | WO 2012072980 A1 | 6/2012 | |
| WO | WO 2012137506 A1 | 10/2012 | |
| WO | WO 2013095896 A1 | 12/2012 | |
| WO | WO 2013086015 A1 | 6/2013 | |
| WO | WO 2013103712 A1 | 7/2013 | |
| WO | WO 2013111054 A1 | 8/2013 | |
| WO | WO 2013169924 A1 | 11/2013 | |
| WO | WO 2014041093 A1 | 3/2014 | |
| WO | WO 2014146062 A2 | 9/2014 | |
| WO | WO 2014146062 A3 | 9/2014 | |
| WO | WO 2015137595 A1 | 9/2015 | |
| WO | WO 2017048871 A1 | 3/2017 | |

OTHER PUBLICATIONS

Becton, Dickinson and Company, 2013, "BD™ EMB Agar (Eosin Methylene Blue Agar), Modified Intended Use," retrieved from the internet: URL: https://legacy.bd.com/RESOURCE.ASPX?IDX=8973 [retrieved on Apr. 2, 2020] (3 pages).

Cardinal Health, 2013, "Histology vol. II: Laboratory products for your Histology needs," retrived from the Internet: URL:http://www.henryschein.com/assets/medical/2883001.pdf [retreived on Apr. 2, 2020] (95 pages).

Deiss et al., 2014, "Antimicrobial susceptibility assays in paper-based portable culture devices," Lab on a Chip, 14(1):167-171.

Dictionary.com, definition of "mesh," retrieved from internet: https://www.dictionary.com/browse/mesh?s=t on Feb. 3, 2020 (6 pages).

English translation of the International Search Report and Written Opinion of International Patent Application No. PCT/KR2017/002026 (published as WO 2017/146502) dated May 29, 2017 (7 pages).

English translation of the International Search Report and Written Opinion of International Patent Application No. PCT/KR2017/002027 (published as WO 2017/146503) dated May 29, 2017 (8 pages).

English translation of the International Search Report and Written Opinion of International Patent Application No. PCT/KR2017/002028 (published as WO 2017/146504) dated Jul. 6, 2017 (9 pages).

English translation of the International Search Report and Written Opinion of International Patent Application No. PCT/KR2017/002029 (published as WO 2017/146505) dated May 29, 2017 (9 pages).

English translation of the International Search Report and Written Opinion of International Patent Application No. PCT/KR2017/002030 (published as WO 2017/146506) dated May 29, 2017 (9 pages).

English translation of the International Search Report and Written Opinion of International Patent Application No. PCT/KR2017/002031 (published as WO 2017/146507) dated May 29, 2017 (12 pages).

English translation of the International Search Report and Written Opinion of International Patent Application No. PCT/KR2017/002032 (published as WO 2017/146508) dated May 29, 2017 (11 pages).

Geckil et al., 2010, "Engineering hydrogels as extracellular matrix mimics," Nanomedicine (Lond), 5(3):469-484.

Horibata et al., 2015, "Utilization of the Soft Agar Colony Formation Assay to Identify Inhibitors of Tumorigenicity in Breast Cancer Cells," J Vis Exp., (99):e52727 (7 pages).

Hudzicki, 2009, "Kirby-Bauer Disk Diffusion Susceptibility Test Protocol," American Society for Microbiology, retrieved from the internet: https://www.asm.org/getattachment/2594ce26-bd44-47f6-8287-0657aa9185ad/kirby-bauer-disk-diffusion-susceptibility-test-protocol-pdf.pdf, retreived on Jul. 23, 2019 (23 pages).

Liu et al., 2009, "Aptamer-nanoparticle strip biosensor for sensitive detection of cancer cells," Anal Chem., 81(24):10013-10018.

Massart et al., 2009, "Striatal GPR88 expression is confined to the whole projection neuron population and is regulated by dopaminergic and glutamatergic afferents," Eur J Neurosci., 30(3):397-414.

Matsuo et al., 2001, "A simple method for classification of cell death by use of thin layer collagen gel for the detection of apoptosis and/or necrosis after cancer chemotherapy," Jpn J Cancer Res., 92(7):813-819.

Notodihardjo et al., 2015, "Gelatin hydrogel impregnated with platelet-rich plasma releasate promotes angiogenesis and wound healing in murine model," J Artif Organs., 18(1):64-71.

Oss-Ronen et al., 2011, "Polymer-conjugated albumin and fibrinogen composite hydrogels as cell scaffolds designed for affinity-based drug delivery," Acta Biomater, 7(1):163-170.

Punyani et al., 2006, "Sustained release of iodine from a polymeric hydrogel device for water disinfection," Journal of Applied Polymer Science, 103(5):3334-3340.

Rand, 1996, "Crystal violet can be used to visualize DNA bands during gel electrophoresis and to improve cloning efficiency," Technical Tips Online, 1:23-24.

Romano et al., 2015, "Controlled antiseptic/eosin release from chitosan-based hydrogel modified fibrous substrates," Cathohydr Polym., 131:306-314.

Wakayama et al., 2013, "Design of a single-step immunoassay principle based on the combination of an enzyme-labeled antibody release coating and a hydrogel copolymerized with a fluorescent enzyme substrate in a microfluidic capillary device," Lab Chip, 13(22):4304-4307.

Wu et al., 2008, "Disposable reagentless electrochemical immunosensor array based on a biopolymer/sol-gel membrane for simultaneous measurement of several tumor markers," Clin Chem., 54(9):1481-1488.

Zhu et al., 2015, "Microbiology Experiment and Learning Guide—Experiment 6 In Vitro Antibacterial Test of Drug," Fourth Force Medical University Press, pp. 24-26 (in Chinese with English translation), 11 pages.

Zustiak et al., 2010, "Solute diffusion and interactions in cross-linked poly(ethylene glycol) hydrogels studied by Fluorescence Correlation Spectroscopy," Soft Matter, 6(15):3609-3618.

Beck, M., et al., "On-chip sample preparation by controlled release of antibodies for simple CD4 counting", Lab Chip, 2012, 12, 167, 7 pages.

Man et al., 2011, "Currently Used Markers for CTC Isolation—Advantages, Limitations and Impact on Cancer Prognosis," J Clinic Experiment Pathol, 1:1 (7 pages).

* cited by examiner (a)

(b)

POLYMERASE CHAIN REACTION PATCH, METHOD AND DEVICE FOR DIAGNOSIS USING THE SAME

CROSS-REFERENCES TO RELATED APPLICATIONS

This application is a U.S. national phase application, pursuant to 35 U.S.C. § 371, of PCT/KR2017/002026, filed Feb. 23, 2017, designating the United States, which claims the benefit of U.S. Provisional Application No. 62/298,959, filed Feb. 23, 2016, and claims priority to Korean Application No. 10-2016-0069936, filed Jun. 4, 2016, to Korean Application No. 10-2016-0069937, filed Jun. 4, 2016, to Korean Application No. 10-2016-0069938, filed Jun. 4, 2016, to Korean Application No. 10-2016-0095739, filed Jul. 27, 2016, to Korean Application No. 10-2016-0118462, filed Sep. 13, 2016, to Korean Application No. 10-2016-0144551, filed Nov. 1, 2016, and to Korean Application No. 10-2017-0024387, filed Feb. 23, 2017. The entire contents of the aforementioned patent applications are incorporated herein by this reference.

TECHNICAL FIELD

The present disclosure relates to a polymerase chain reaction (PCR) patch, a method and device for diagnosis using the same, and more particularly, to a patch that comes into contact with a sample such as blood so as to amplify a target gene included in the sample, and a method of and device for diagnosis for performing a PCR using the same.

BACKGROUND ART

Polymerase chain reaction (hereinafter referred to as PCR) is a testing method for a more accurate diagnosis, in which a specific target genetic material desired to be detected is amplified so as to amplify small amounts of genetic materials with the same base sequence. PCR testing is not only used in amplifying a human's DNA to diagnose a genetic disorder, but may also be applied to the DNA of bacteria, viruses, or fungi and be used in diagnosing an infectious disease.

Particularly, in the case of a viral disease, due to the possibility of infection, a failure to respond quickly may become a national problem. For example, in the case of Middle East Respiratory Syndrome (MERS) in 2015, beginning from an initial infected person, over 100 people were definitively diagnosed with MERS, and about 30 people died. Therefore, it is essential to promptly perform testing on people who are subject to diagnosis and perform accurate diagnosis to prevent the increase of infected people by methods such as letting infected people self-quarantine.

A conventional PCR diagnosis method is performed by a method in which a sample is inserted into a tube for PCR testing, the sample is mixed with a reagent used in PCR testing, and a temperature of the sample mixed with the reagent is adjusted. Accordingly, there are problems in that the amount of reagent should be measured in the process in which the reagent is mixed with the sample, and a large amount of time is taken to adjust the temperature of the sample mixed with the reagent.

Accordingly, a means for providing a reagent used in diagnosis to a sample through a convenient procedure and also reducing time taken for temperature adjustment is required.

SUMMARY

An aspect of the present disclosure is to provide a patch capable of storing a substance.

An aspect of the present disclosure is to provide a patch capable of providing a reaction space for a substance.

An aspect of the present disclosure is to provide a patch capable of providing a substance.

An aspect of the present disclosure is to provide a patch capable of absorbing a substance.

An aspect of the present disclosure is to provide a patch capable of providing an environment.

An aspect of the present disclosure is to provide a patch that contains a reagent used in a polymerase chain reaction (PCR).

An aspect of the present disclosure is to provide a method for a PCR using a patch.

According to an aspect of the present disclosure, there is provided a polymerase chain reaction (PCR) patch which is provided as a gel type having a net-like structure forming micro-cavities, wherein at least a part of a plurality of reagents used in a PCR are contained in the micro-cavities, and when the patch contacts with an external region, the reagents contained in the micro-cavities move to at least a portion of the external region, and a PCR of a target DNA is performed, wherein the target DNA is included in a sample located in the external region.

According to another aspect of the present disclosure, there is provided a PCR patch set that includes a plurality of patches used in performing a PCR, the patches provided as a gel type having a net-like structure forming micro-cavities, the PCR patch set including a first patch configured to contain at least a first reagent among a plurality of reagents used in the PCR in the micro-cavities, and a second patch configured to contain at least a second reagent among the plurality of reagents used in the PCR in the micro-cavities, wherein the first reagent is different from the second reagent.

According to still another aspect of the present disclosure, there is provided a PCR method for performing a PCR of a target DNA by using a patch which is provided as a gel type having a net-like structure forming micro-cavities, the PCR method including providing, with using a first patch being configured to contain at least a part of a plurality of reagents used in the PCR in the micro cavities, the reagents contained in the first patch to a sample provided on a plate, and adjusting temperature of the sample to cause the PCR.

According to yet another aspect of the present disclosure, there is provided a diagnostic apparatus for perform a PCR of a target DNA included in a sample with using a patch provided as a gel type having a net-like structure forming micro-cavities and containing a reagent used in a PCR, the diagnostic apparatus including a relative movement adjusting module configured to relatively move the patch and a region where the sample is provided to each other in order to provide the reagent contained in the patch to the sample, a temperature adjusting module configured to adjust the temperature of the sample to a temperature that causes the PCR, and an image acquiring module configured to acquire an image of the sample to detect the target DNA included in the sample.

According to the present disclosure, containing, providing, and absorption of a substance can be easily performed.

According to the present disclosure, a reaction region for a substance can be provided or a predetermined environment can be provided to a target region.

According to the present disclosure, PCR testing can be more conveniently performed, and a diagnosis result can be promptly obtained.

According to the present disclosure, delivery and absorption of a substance can be properly adjusted using a patch, and thus an amount of solution required for diagnosis can be significantly reduced.

According to the present disclosure, multiple target DNAs can be amplified simultaneously and detected.

Advantageous effects of the present disclosure are not limited to those mentioned above, and unmentioned advantageous effects should be clearly understood by those of ordinary skill in the art to which the present disclosure pertains from the present specification and the accompanying drawings.

DETAILED DESCRIPTION

Figure 1:
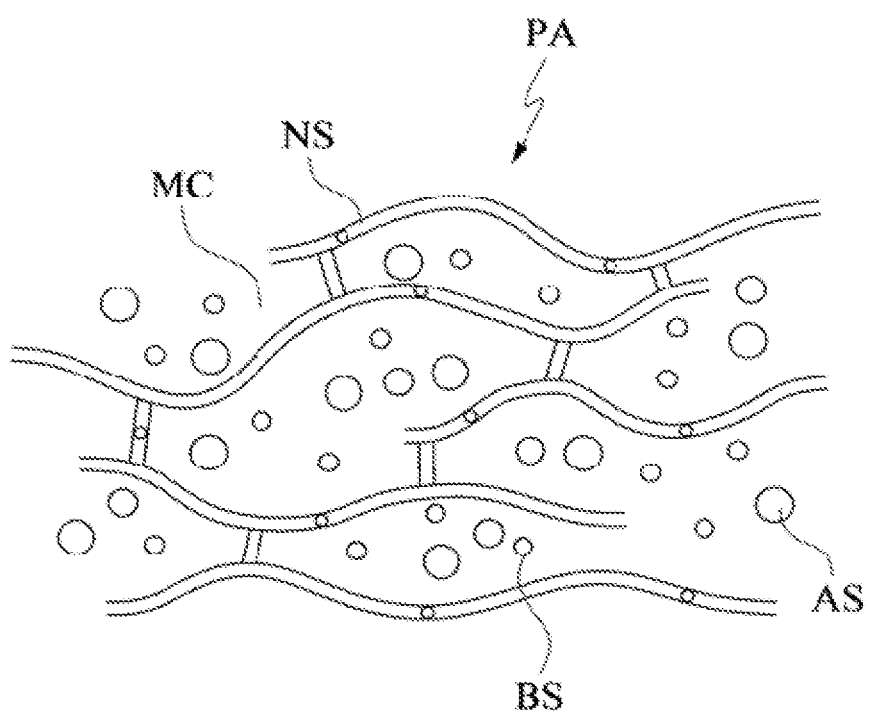
FIG. 1 illustrates an example of a patch in detail according to the present application.

Since embodiments described herein are for clearly describing the spirit of the present application to those of ordinary skill in the art to which the present application pertains, the present application is not limited to the embodiments described herein, and the scope of the present application should be construed as including revised examples or modified examples not departing from the spirit of the present application.

General terms currently being used as widely as possible have been selected as terms used herein in consideration of functions in the present application, but the terms may be changed according to intentions and practices of those of ordinary skill in the art to which the present application pertains or the advent of new technologies, etc. However, instead, when a particular term is defined as a certain meaning and used, the meaning of the term will be separately described. Consequently, the terms used herein should be construed on the basis of substantial meanings of the terms and content throughout the present specification instead of simply on the basis of names of the terms.

The accompanying drawings herein are for easily describing the present application. Since shapes illustrated in the drawings may have been exaggeratedly depicted as much as necessary to assist in understanding the present application, the present application is not limited by the drawings.

When detailed description of a known configuration or function related to the present application is deemed to obscure the gist of the present application in the present specification, the detailed description related thereto will be omitted as necessary.

According to an aspect of the present application, there is provided a polymerase chain reaction (PCR) patch which is provided as a gel type having a net-like structure forming micro-cavities, wherein at least a part of a plurality of reagents used in a PCR are contained in the micro-cavities, and when the patch contacts with an external region, the reagents contained in the micro-cavities move to at least a portion of the external region, and a PCR of a target DNA is performed, wherein the target DNA is included in a sample located in the external region.

The reagents contained in the micro-cavities of the patch may include a first substance that reacts specifically with the target DNA.

The reagents contained in the micro-cavities of the patch may include a second substance that reacts with a DNA bound to the first substance, and a third substance that provides an environment for a PCR of the second substance.

The first substance may be bound to a substance that induces fluorescence.

The first substance may include a fourth substance that reacts specifically with a first target DNA and a fifth substance that reacts specifically with a second target DNA.

The patch may include a first region and a second region, wherein a reagent contained in the first region may not move to the second region, and a reagent contained in the second region may not move to the first region.

The first region may include a fourth substance that reacts specifically with a first target DNA and the second region may include a fifth substance that reacts specifically with a second target DNA.

The external region may be a plate on which the sample is providable, and the sample may be provided in a single layer on the plate.

At least a part of the plurality of reagents used in the PCR may be applied on the plate, and when the patch and the plate come into contact, the reagents applied on the plate may become involved in the PCR of the target DNA included in the sample.

The reagents applied on the plate may include a second substance that reacts with a DNA bound to a primer, and the reagents contained in the micro-cavities of the patch may include a third substance that provides an environment for a PCR of the second substance.

According to another aspect of the present application, there is provided a PCR patch set that includes a plurality of patches used in performing a PCR, the patches provided as a gel type having a net-like structure forming micro-cavities, the PCR patch set including a first patch configured to contain at least a first reagent from among a plurality of reagents used in the PCR in the micro-cavities, and a second patch configured to contain at least a second reagent from among the plurality of reagents used in the PCR in the micro-cavities, wherein the first reagent is different from the second reagent.

The first reagent may include a first substance that reacts specifically with a target DNA, and the second reagent may react specifically with the target DNA and have a base sequence complementary to the first substance.

The first reagent may include a first substance that reacts specifically with a target DNA, and the second reagent may include a second substance that reacts with a DNA bound to the first substance.

The first reagent may include a second substance that reacts with a DNA bound to a primer, and the second reagent may include a third substance that provides an environment for a PCR of the second substance.

According to still another aspect of the present application, there is provided a PCR method for performing a PCR of a target DNA by using a patch provided as a gel type having a net-like structure forming micro-cavities, the PCR method including providing, with using a first patch being configured to contain at least a part of a plurality of reagents used in the PCR in the micro cavities, the reagents contained in the first patch to a sample provided on a plate, and adjusting temperature of the sample to cause the PCR.

The providing the reagents contained in the first patch may include contacting the first patch and the plate.

The adjusting the temperature of the sample may include adjusting temperature of the plate in order to adjust the temperature of the sample provided on the plate.

The PCR method may further include separating the contact between the plate and the first patch when temperature of the plate is higher than or equal to a reference temperature.

The adjusting the temperature of the sample may include adjusting temperature of the first patch in order to adjust the temperature of the sample.

The adjusting the temperature of the first patch may be performed prior to the contacting the plate and the first patch.

The adjusting the temperature of the sample may include contacting the plate and a temperature-adjusted metal material in order to adjust the temperature of the sample.

The PCR method may further include providing, with using a second patch being configured to contain at least a part of a plurality of reagents used in the PCR in the micro cavities, the reagents contained in the second patch to a sample provided on the plate, and wherein a first reagent contained in the first patch may not be contained in the second patch.

A second reagent contained in the second patch may be contained in the first patch.

The providing the reagents contained in the second patch may include contacting the second patch and the plate.

The adjusting the temperature of the sample may include at least one of adjusting temperature of the first patch and adjusting temperature of the second patch.

The providing the reagents contained in the first patch may be performed after the adjusting the temperature of the first patch, and the providing of the reagents contained in the second patch may be performed the adjusting the temperature of the second patch.

The reagents contained in the first patch may include a first substance that reacts specifically with a target DNA, and the reagents contained in the second patch may include a second substance that reacts with a DNA bound to the first substance.

The providing the reagents contained in the second patch may include contacting the second patch and the first patch.

The providing the reagents contained in the first patch may include contacting the first patch and the plate in several times.

According to yet another aspect of the present application, there is provided a diagnostic apparatus for perform a PCR of a target DNA included in a sample with using a patch which is provided as a gel type having a net-like structure forming micro-cavities and containing a reagent used in a PCR, the diagnostic apparatus including a relative movement adjusting module configured to relatively move the patch and a region in which the sample is provided in order to provide the reagent contained in the patch to the sample, a temperature adjusting module configured to adjust the temperature of the sample to a temperature that causes the PCR, and an image acquiring module configured to acquire an image of the sample to detect the target DNA included in the sample.

1. Patch 1.1 Meaning of Patch

In the present application, a patch for managing a liquid substance is disclosed.

The liquid substance may mean a substance which is in a liquid state and can flow.

The liquid substance may be a substance formed of a single component having fluidity. Alternatively, the liquid substance may be a mixture that includes a substance formed of a plurality of components.

When the liquid substance is a substance formed of a single component, the liquid substance may be a substance formed of a single chemical element or a compound including a plurality of chemical elements.

When the liquid substance is a mixture, a portion of the substance formed of a plurality of components may serve as a solvent, and the other portion may serve as a solute. That is, the mixture may be a solution.

A plurality of components constituting the mixture which forms the substance may be uniformly distributed. Alternatively, the mixture including the substance formed of a plurality of components may be a uniformly mixed mixture.

The substance formed of a plurality of components may include a solvent and a substance that is not dissolved in the solvent and is uniformly distributed.

A portion of the substance formed of a plurality of components may be non-uniformly distributed. The non-uniformly distributed substance may include non-uniformly distributed particle components in the solvent. In this case, the non-uniformly distributed particle components may be in a solid phase.

For example, a substance that may be managed using the patch may be in a state of 1) a liquid formed of a single component, 2) a solution, or 3) a colloid, or according to circumstances, may be in a state in which 4) solid particles are non-uniformly distributed within another liquid substance.

Hereinafter, the patch according to the present application will be described in more detail.

1.2 General Nature of Patch

1.2.1 Configuration

Figure 2:
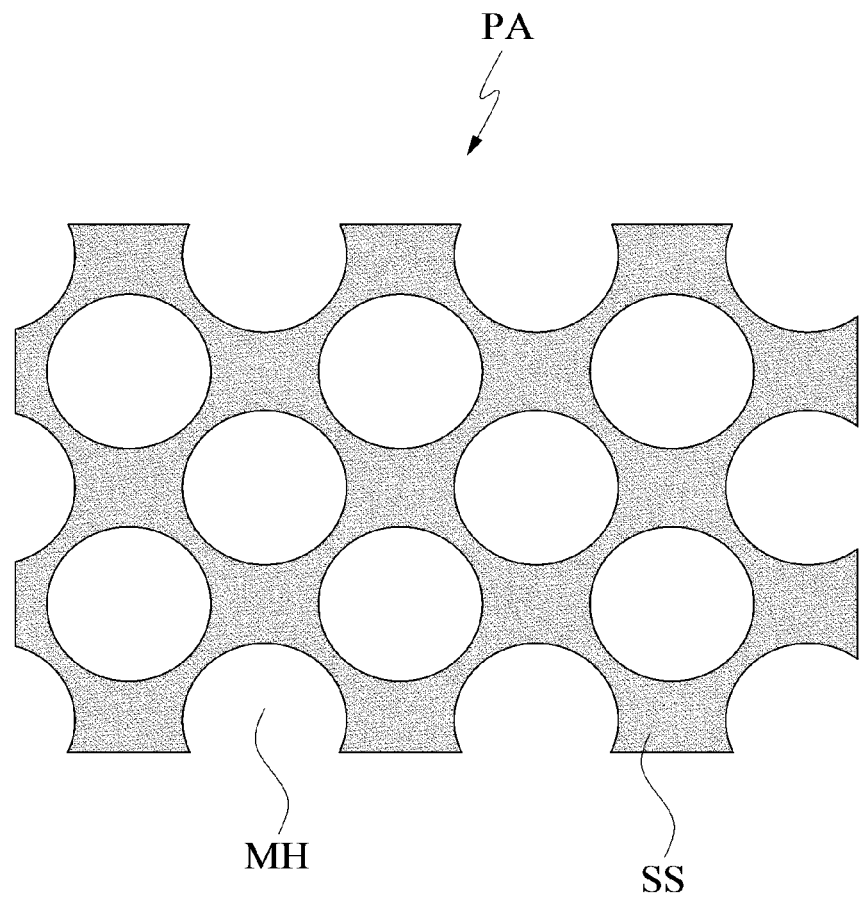
FIG. 2 illustrates an example of a patch in detail according to the present application.

FIGS. 1 and 2 are views illustrating an example of a patch according to the present application. The patch according to the present application will be described below with reference to FIGS. 1 and 2.

Referring to FIG. 1, a patch PA according to the present application may include a mesh structural body NS and a liquid substance.

As the liquid substance, a base substance BS and an additive substance AS may be taken into consideration separately.

The patch PA may be in a gel state(gel type). The patch PA may be implemented as a gel-type structural body in which colloidal molecules are bound and mesh tissues are formed.

The patch PA according to the present application is a structure for managing a liquid substance SB, and may include a three-dimensional mesh (net-like) structural body NS. The mesh structural body NS may be a continuously distributed solid structure. The mesh structural body NS may have a mesh structure in which a plurality of micro-threads are intertwined. However, the mesh structural body NS is not limited to the mesh form in which the plurality of micro-threads are intertwined, and may also be implemented in the form of an arbitrary three-dimensional matrix that is formed by connection of a plurality of micro-structures. For example, the mesh structural body NS may be a frame structural body that includes a plurality of micro-cavities. In other words, the mesh structural body NS may form a plurality of micro-cavities MC.

FIG. 2 illustrates a structure of a patch according to an embodiment of the present application. Referring to FIG. 2, the mesh structural body of the patch PA may have a sponge structure SS. The mesh structural body of the sponge structure SS may include a plurality of micro-holes MH. Hereinafter, the terms micro-holes MH and the micro-cavities MC may be used interchangeably, and unless particularly mentioned otherwise, the term micro-cavities MC is defined as encompassing the concept of the micro-holes MH.

The mesh structural body NS may have a regular or irregular pattern. Furthermore, the mesh structural body NS may include both a region having a regular pattern and a region having an irregular pattern.

A density of the mesh structural body NS may have a value within a predetermined range. Preferably, the predetermined range may be set within a limit in which the form of the liquid substance SB captured in the patch PA is maintained in a form that corresponds to the patch PA. The density may be defined as a degree to which the mesh structural body NS is dense or a mass ratio, a volume ratio, or the like that the mesh structural body NS occupies in the patch.

The patch according to the present application may manage the liquid substance SB by having a three-dimensional mesh structure.

The patch PA according to the present application may include the liquid substance SB, and the fluidity of the liquid substance SB included in the patch PA may be limited by the form of the mesh structural body NS of the patch PA.

The liquid substance SB may freely flow within the mesh structural body NS. In other words, the liquid substance SB is placed in the plurality of micro-cavities formed by the mesh structural body NS. An exchange of liquid substance SB may occur between neighboring micro-cavities. In this case, the liquid substance SB may be present in a state in which the liquid substance SB permeating into a frame structural body that forms the mesh tissues. In such a case, nano-sized pores into which the liquid substances SB may permeate may be formed in the frame structural body.

Further, whether to the liquid substance SB is filled in the frame structural body of the mesh structure may be determined depending on a molecular weight or a particle size of the liquid substance SB to be captured in the patch PA. A substance having a relatively large molecular weight may be captured in the micro-cavities, and a substance having a relatively small molecular weight may be captured by the frame structural body and filled in the micro-cavities and/or the frame structural body of the mesh structural body NS.

In the present specification, the term "capture" may be defined as a state in which the liquid substance SB is placed in the plurality of micro-cavities and/or nano-sized holes formed by the mesh structural body NS. As described above, the state in which the liquid substance SB is captured in the patch PA is defined as including a state in which the liquid substance SB may flow between the micro-cavities and/or the nano-sized holes.

As in the following, the base substance BS and the additive substance AS may be taken into consideration separately as the liquid substance SB.

The base substance BS may be a liquid substance SB having fluidity.

The additive substance AS may be a substance that is mixed with the base substance BS and has fluidity. In other words, the base substance BS may be a solvent. The additive substance AS may be a solute that is dissolved in the solvent or may be particles that are not melted in the solvent.

The base substance BS may be a substance capable of flowing inside a matrix formed by the mesh structural body NS. The base substance BS may be uniformly distributed in the mesh structural body NS or may be distributed only in a partial region of the mesh structural body NS. The base substance BS may be a liquid having a single component.

The additive substance AS may be a substance that is mixed with the base substance BS or dissolved in the base substance BS. For example, the additive substance AS may serve as a solute while the base substance BS is a solvent. The additive substance AS may be uniformly distributed in the base substance BS.

The additive substance AS may be fine particles that are not dissolved in the base substance BS. For example, the additive substance AS may include colloidal molecules and fine particles such as microorganisms.

The additive substance AS may include particles larger than the micro-cavities formed by the mesh structural body NS. When the size of the micro-cavities is smaller than the size of the particles included in the additive substance AS, fluidity of the additive substance AS may be limited.

According to an embodiment, the additive substance AS may include a component that is selectively included in the patch PA.

The additive substance AS does not necessarily refer to a substance that is lower in quantity or inferior in function in comparison to the above-described base substance BS.

Hereinafter, characteristics of the liquid substance SB captured in the patch PA may be presumed as characteristics of the patch PA. That is, the characteristics of the patch PA may depend on characteristics of a substance captured in the patch PA.

1.2.2 Characteristics

As described above, the patch PA according to the present application may include the mesh structural body NS. The patch PA may manage the liquid substance SB through the mesh structural body NS. The patch PA may allow the liquid substance SB captured in the patch PA to maintain at least some of its unique characteristics.

For example, diffusion of a substance may occur in a region of the patch PA in which the liquid substance SB is distributed, and a force such as surface tension may come into action.

The patch PA may provide a liquid environment in which diffusion of a target substance is caused due to thermal motion of a substance or a difference in density or concentration thereof. Generally, "diffusion" refers to a phenomenon in which particles that constitute a substance are spread from a side at which concentration is high to a side at which a concentration is low due to a difference in concentration. Such a diffusion phenomenon may be basically understood as a phenomenon that occurs due to motion of molecules (translational motion in a gas or liquid, vibrational motion in a solid, and the like). In the present application, in addition to referring to the phenomenon in which particles are spread from a side at which a concentration is high toward a side at which a concentration is low due to a difference in concentration or density, "diffusion" also refers to a phenomenon in which particles move due to irregular motion of molecules that occurs even when a concentration is uniform. The expression "irregular motion" may also have the same meaning as "diffusion" unless particularly mentioned otherwise. The diffused substance may be a solute that is dissolved in the liquid substance SB, and the diffused substance may be provided in a solid, liquid, or gas state.

More specifically, a non-uniformly-distributed substance in the liquid substance SB captured by the patch PA may be diffused in a space provided by the patch PA. In other words, the additive substance AS may be diffused in a space defined by the patch PA.

The non-uniformly-distributed substance or the additive substance AS in the liquid substance SB managed by the patch PA may be diffused within the micro-cavities provided by the mesh structural body NS of the patch PA. A region in which the non-uniformly-distributed substance or the additive substance AS may be diffused may be changed by the patch PA being connected or coming into contact with another substance.

Even when, after the concentration of the substance or the additive substance AS has become uniform, as a result of diffusion of the non-uniformly-distributed substance or the additive substance AS within the patch PA or within an external region connected to the patch PA, the substance or the additive substance AS may continuously move due to irregular motion of molecules inside the patch PA and/or within the external region connected to the patch PA.

The patch PA may be implemented to exhibit a hydrophilic or hydrophobic property. In other words, the mesh structural body NS of the patch PA may have a hydrophilic or hydrophobic property.

When properties of the mesh structural body NS and the liquid substance SB are similar, the mesh structural body NS may be able to manage the liquid substance SB more effectively.

The base substance BS may be a polar hydrophilic substance or a nonpolar hydrophobic substance. The additive substance AS may exhibit a hydrophilic or hydrophobic property.

The properties of the liquid substance SB may be related to the base substance BS and/or the additive substance AS. For example, when both the base substance BS and the additive substance AS are hydrophilic, the liquid substance SB may be hydrophilic, and when both the base substance BS and the additive substance AS are hydrophobic, the liquid substance SB may be hydrophobic. When polarities of the base substance BS and the additive substance AS are different, the liquid substance SB may be hydrophilic or hydrophobic.

When polarities of both the mesh structural body NS and the liquid substance SB are hydrophilic or hydrophobic, an attractive force may come into action between the mesh structural body NS and the liquid substance SB. When polarities of the mesh structural body NS and the liquid substance SB are opposite, e.g., when the polarity of the mesh structural body NS is hydrophobic and the polarity of the liquid substance SB is hydrophilic, a repulsive force may act between the mesh structural body NS and the liquid substance SB.

On the basis of the above-described properties, the patch PA may be solely used, a plurality of patches PA may be used, or the patch PA may be used with another medium to induce a desired reaction. Hereinafter, functional aspects of the patch PA will be described.

However, hereinafter, for convenience of description, the patch PA is assumed as being a gel type that may include a hydrophilic solution. In other words, unless particularly mentioned otherwise, the mesh structural body NS of the patch PA is assumed to have a hydrophilic property.

However, the scope of the present application should not be interpreted as being limited to the gel-type patch PA having a hydrophilic property. In addition to a gel-type patch PA that includes a solution exhibiting a hydrophobic property, a gel-type patch PA from which a solvent is removed and even a sol-type patch PA, as long as it is capable of implementing functions according to the present application, may belong to the scope of the present application.

2. Functions of Patch

Due to the above-described characteristics, the patch according to the present application may have some useful functions. In other words, by capturing the liquid substance SB, the patch may become involved in behavior of the liquid substance SB.

Accordingly, hereinafter, in accordance with forms of behavior of the substance with respect to the patch PA, a reservoir function in which a state of the substance is defined in a predetermined region formed by the patch PA and a channeling function in which a state of the substance is defined in a region including an external region of the patch PA will be separately described.

2.1 Reservoir

2.1.1 Meaning

As described above, the patch PA according to the present application may capture the liquid substance SB. In other words, the patch PA may perform a function as a reservoir.

The patch PA may capture the liquid substance SB in the plurality of micro-cavities formed in the mesh structural body NS using the mesh structural body NS. The liquid substance SB may occupy at least a portion of the fine micro-cavities formed by the three-dimensional mesh structural body NS of the patch PA or be penetrated in the nano-sized pores formed in the mesh structural body NS.

The liquid substance SB placed in the patch PA does not lose properties of a liquid even when the liquid substance SB is distributed in the plurality of micro-cavities. That is, the liquid substance SB has fluidity even in the patch PA, and diffusion of a substance may occur in the liquid substance SB distributed in the patch PA, and an appropriate solute may be dissolved in the substance.

The reservoir function of the patch PA will be described below in more detail.

2.1.2 Containing

In the present application, the patch PA may capture a target substance due to the above-described characteristics. The patch PA may have resistance to a change in an external environment within a predetermined range. In this way, the patch PA may maintain a state in which the substance is captured therein. The liquid substance SB, which is a target to be captured, may occupy the three-dimensional mesh structural body NS.

Hereinafter, for convenience, the above-described function of the patch PA will be referred to as "containing."

However, "the patch PA containing the liquid substance" is defined to encompass a case in which the liquid substance is contained in a space formed by the mesh structure and/or a case in which the liquid substance is contained in the frame structural body constituting the mesh structural body NS.

The patch PA may contain the liquid substance SB. For example, the patch PA may contain the liquid substance SB, due to an attractive force that acts between the mesh structural body NS of the patch PA and the liquid substance SB. The liquid substance SB may be bound to the mesh structural body NS with an attractive force of a predetermined strength or higher and contained in the patch PA.

Properties of the liquid substance SB contained in the patch PA may be classified in accordance with properties of the patch PA. More specifically, when the patch PA exhibits a hydrophilic property, the patch PA may be bound to a hydrophilic liquid substance SB which is polar in general and contain the hydrophilic liquid substance SB in the three-dimensional micro-cavities. Alternatively, when the patch PA exhibits a hydrophobic property, the hydrophobic liquid substance SB may be contained in the micro-cavities of the three-dimensional mesh structural body NS.

The amount of substance that may be contained in the patch PA may be proportional to a volume of the patch PA. In other words, the amount of substance contained in the patch PA may be proportional to an amount of three-dimensional mesh structural body NS that serves as a support body that contributes to the form of the patch PA. However, there is no constant proportional factor between the amount of substance that may be contained in the patch PA and the volume of the patch PA, and thus the relationship between the amount of substance that may be contained in the patch PA and the volume of the patch PA may be changed in accordance with the design or manufacturing method of the mesh structure.

The amount of substance contained in the patch PA may be reduced due to evaporation, loss, etc. with time. The substance may be additionally injected into the patch PA to increase or maintain the content of the substance contained in the patch PA. For example, a moisture keeping agent for suppressing evaporation of moisture may be added to the patch PA.

The patch PA may be implemented in a form in which it is easy to store the liquid substance SB. This signifies that, when the substance is affected by environmental factors such as humidity level, amount of light, and temperature, the patch PA may be implemented to minimize denaturalization of the substance. For example, to prevent the patch PA from being denaturalized due to external factors such as bacteria, the patch PA may be treated with a bacteria inhibitor.

A liquid substance SB having a plurality of components may be contained in the patch PA. In this case, the substance formed of a plurality of components may be placed together in the patch PA before a reference time point, or a primarily-injected substance may be first contained in the patch PA and then a secondary substance may be contained in the patch PA after a predetermined amount of time. For example, when a liquid substance SB formed of two components is contained in the patch PA, the two components may be contained in the patch PA upon manufacturing the patch PA, only one component may be contained in the patch PA upon manufacturing the patch PA and the other component may be contained therein later, or the two components may be sequentially contained in the patch PA after the patch PA is manufactured.

As described above, the substance contained in the patch may exhibit fluidity, and the substance may move irregularly or be diffused due to molecular motion in the patch PA.

2.1.3 Providing of Reaction Space

Figure 3:
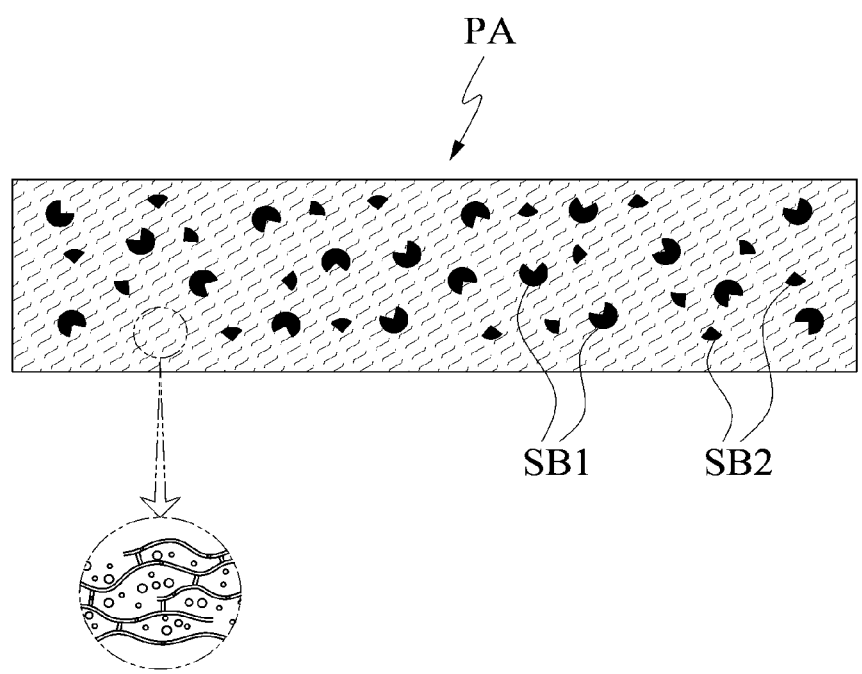
FIG. 3 illustrates providing of a reaction space as an example of a function of a patch according to the present application.
Figure 4:
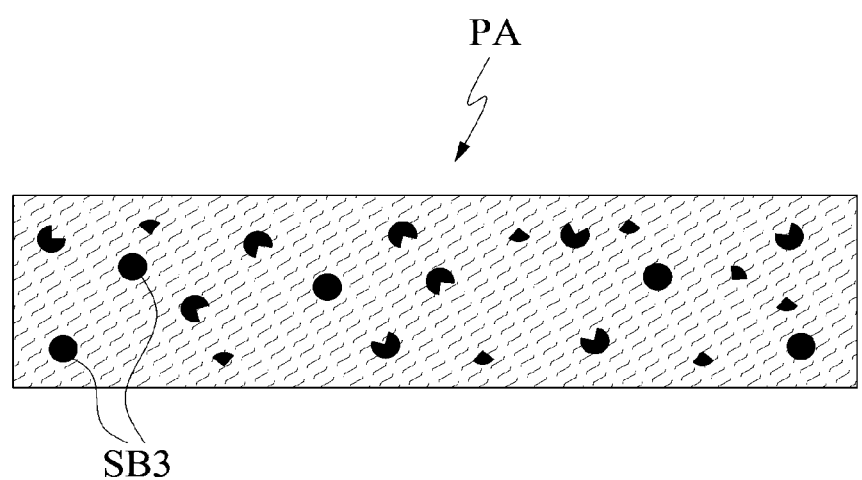
FIG. 4 illustrates providing of a reaction space as an example of a function of a patch according to the present application.

FIGS. 3 and 4 are views illustrating providing a reaction space as an example of a function of the patch according to the present application.

As illustrated in FIGS. 3 and 4, the patch PA according to the present application may perform a function of providing a space. In other words, the patch PA may provide a space in which the liquid substance SB may move through a space formed by the mesh structural body NS and/or a space constituting the mesh structural body NS.

The patch PA may provide a space for activity other than diffusion of particles and/or irregular motion of particles (hereinafter referred to as activity other than diffusion). The activity other than diffusion may refer to a chemical reaction, but is not limited thereto, and may also refer to a physical state change. More specifically, the activity other than diffusion may include a chemical reaction in which a chemical composition of the substance changes after the activity, a specific binding reaction between components included in the substance, homogenization of solutes or particles included in the substance and non-uniformly distributed therein, condensation of some components included in the substance, or a biological activity of a portion of the substance.

When a plurality of substances become involved in the activity, the plurality of substances may be placed together in the patch PA before a reference time point. The plurality of substances may be sequentially inserted into the patch PA.

By changing environmental conditions of the patch PA, efficiency of the function of providing a space for activities other than diffusion in the patch PA may be enhanced. For example, the activity may be promoted or a start of the activity may be induced by changing a temperature condition of the patch PA or adding an electrical condition thereto.

According to FIGS. 3 and 4, a first substance SB1 and a second substance SB2 placed in the patch PA may react inside the patch PA and be deformed into a third substance SB3 or generate the third substance SB3.

2.2 Channel

2.2.1 Meaning

Movement of a substance may occur between the patch PA and an external region. The substance may be moved from the patch PA to the external region of the patch PA or may be moved from the external region to the patch PA.

The patch PA may form a substance movement path or get involved in movement of the substance. More specifically, the patch PA may become involved in movement of the liquid substance SB captured in the patch PA or become involved in movement of an external substance through the liquid substance SB captured in the patch PA. The base substance BS or the additive substance AS may move out from the patch PA, or an external substance may be introduced from an external region to the patch PA.

The patch PA may provide a substance movement path. That is, the patch PA may become involved in movement of the substance and provide a substance movement channel. The patch PA may provide a substance movement channel based on unique properties of the liquid substance SB.

In accordance with whether the patch PA is connected to the external region, the patch PA may be in a state in which the liquid substance SB is movable between the patch PA and the external region or a state in which the liquid substance SB is immovable between the patch PA and the external region. When channeling between the patch PA and the external region begins, the patch PA may have unique functions.

Hereinafter, the state in which the substance is movable and the state in which the substance is immovable will be described first, and the unique functions of the patch PA will be described in detail in connection with whether the patch PA and the external region are connected.

Basically, irregular motion and/or diffusion of the substance are fundamental causes of movement of the liquid substance SB between the patch PA and the external region. However, controlling an external environmental factor (e.g., controlling a temperature condition, controlling an electrical condition, or the like) in order to control movement of a substance between the patch PA and the external region has already been described.

2.2.2 Movable State

In the state in which the substance is movable, a flow may occur between the liquid substance SB captured in the patch PA and/or the substance placed in the external region. In the state in which the substance is movable, substance movement may occur between the liquid substance SB captured in the patch PA and the external region.

For example, in the state in which the substance is movable, the liquid substance SB or some components of the liquid substance SB may be diffused to the external region or moved due to irregular motion. Alternatively, in the state in which the substance is movable, an external substance placed in the external region or some components of the external substance may be diffused to the liquid substance SB in the patch PA or moved due to irregular motion.

The state in which the substance is movable may be caused by contact. The contact may refer to connection between the liquid substance SB captured in the patch PA and the external region. Contact may refer to at least a partial overlap between a flow region of the liquid substance SB and the external region. The contact may refer to the external substance being connected to at least a portion of the patch PA. It may be understood that the range in which the captured liquid substance SB may flow is expanded in the state in which the substance is movable. In other words, in the state in which the substance is movable, the range in which the liquid substance SB may flow may be expanded to include at least a portion of the external region of the captured liquid substance SB. For example, when the liquid substance SB is in contact with the external region, the range in which the captured liquid substance SB may flow may be expanded to include at least a portion of the external region in contact. More specifically, when the external region is an external plate, the region in which the liquid substance SB may flow may be expanded to include a region of the external plate in contact with the liquid substance SB.

2.2.3 Immovable State

In the state in which the substance is immovable, substance movement may not occur between the liquid substance SB captured in the patch PA and the external region. However, substance movement may respectively occur in the liquid substance SB captured in the patch PA and in external substance placed in the external region.

The state in which the substance is immovable may be a state in which the contact is released. In other words, in the state in which contact between the patch PA and the external region is released, substance movement is not possible between the liquid substance SB remaining in the patch PA and the external region or the external substance.

More specifically, the state in which the contact is released may refer to a state in which the liquid substance SB captured in the patch PA is not connected to the external region. The state in which the contact is released may refer to a state in which the liquid substance SB is not connected to an external substance placed in the external region. For example, the state in which movement of the substance is impossible may be caused by separation between the patch PA and the external region.

In the present specification, although "movable state" has a meaning differentiated from that of "immovable state," a transition may occur between the states due to an elapse of time, an environmental change, and the like. In other words, the patch PA may be in the immovable state after being in the movable state, in the movable state after being in the immovable state, or may be in the movable state again, after being in the immovable state after being in the movable state.

2.2.4 Differentiation of Functions

2.2.4.1 Delivery

In the present application, due to the above-described characteristics, the patch PA may deliver at least a portion of the liquid substance SB captured in the patch PA to a desired external region. The delivery of the substance may refer to separation of a portion of the liquid substance SB captured in the patch PA from the patch PA due to a predetermined condition being satisfied. The separation of the portion of the liquid substance SB may refer to the portion of the substance being extracted, emitted, or released from a region that is affected by the patch PA. This is a concept subordinate to the above-described channeling function of the patch PA, and may be understood as defining transfer(delivery) of the substance placed in the patch PA to the outside of the patch PA.

The desired external region may be another patch PA, a dried region, or a liquid region.

The predetermined condition for the delivery to occur may be set as an environmental condition such as a temperature change, a pressure change, a change in an electrical characteristic, and a change in a physical state. For example, when the patch PA is in contact with an object whose force of binding to the liquid substance SB is larger than a force of binding to the mesh structural body NS of the patch PA, the liquid substance SB may be chemically bound with the object in contact, and as a result, at least a portion of the liquid substance SB may be provided to the object.

Hereinafter, for convenience, the above-described function of the patch PA will be referred to as "delivery."

The delivery may occur between the patch PA and the external region, via the state in which the liquid substance SB is movable and the state in which the liquid substance SB is immovable between the patch PA and the external region.

More specifically, when the liquid substance SB is in the movable state, the liquid substance SB may be diffused between the patch PA and the external region or may be moved to the external region due to irregular motion. In other words, the base solution and/or the additive substance AS included in the liquid substance SB may be moved from the patch PA to the external region. In the state in which the liquid substance SB is immovable, the liquid substance SB is unable to move between the patch PA and the external region. In other words, due to a transition from the movable state to the immovable state, a portion of the substance that has moved from the patch PA to the external region due to diffusion and/or irregular motion of the liquid substance SB become unable to move back to the patch PA. Thus, a portion of the liquid substance SB may be provided to the external region.

The delivery may be performed due to a difference between an attractive force between the liquid substance SB and the mesh structural body NS and an attractive force between the liquid substance SB and the external region or the external substance. The attractive force may be caused by similarity between polarities or a specific binding relationship.

More specifically, when the liquid substance SB is hydrophilic and the external region or the external substance is more hydrophilic than the mesh structural body NS, at least a portion of the liquid substance SB captured in the patch PA may be provided to the external region via the movable state and the immovable state.

The delivery of the liquid substance SB may also be performed selectively. For example, when a specific binding relationship exists between some components included in the liquid substance SB and the external substance, some of the ingredients may be selectively delivered via the state in which the substance is movable and the state in which the substance is immovable.

More specifically, when it is assumed that the patch PA provides a substance to an external plate PL, which is in a form of a flat plate, a substance that binds specifically to a portion of the liquid substance SB captured in the patch PA (e.g., a portion of a solute) may be applied on the external plate PL. In this case, the patch PA may selectively deliver a portion of the solute that binds specifically to the substance applied on the external plate PL from the patch PA to the plate PL via the movable state and the immovable state.

The delivery as a function of the patch PA will be described below according to a few examples of different regions to which the substance is moved. However, in giving the detailed description, the concepts of "release" of the liquid substance SB and "delivery" of the liquid substance SB may be interchangeably used.

Here, a case in which the liquid substance SB is provided from the patch PA to a separate external plate PL will be described. For example, a case in which the substance is moved from the patch PA to a plate PL, such as a slide glass, may be taken into consideration.

As the patch PA and the plate PL come into contact, at least a portion of the liquid substance SB captured in the patch PA is diffused to the plate PL or moved due to irregular motion. When the contact between the patch PA and the plate PL is released, the portion of the substance that has been moved from the patch PA to the plate PL (that is, the portion of the liquid substance SB) become unable to move back to the patch PA. As a result, the portion of the substance may be provided from the patch PA to the plate PL. In this case, the portion of the substance being provided may be the additive substance AS. For a substance in the patch PA to be "provided" by the contact and separation, an attractive force and/or binding force that acts between the substance and the plate PL should be present, and the attractive force and/or the binding force should be larger than the attractive force acting between the substance and the patch PA. Therefore, if the above-described "delivery condition" is not satisfied, delivery of a substance may not occur between the patch PA and the plate PL.

The delivery of a substance may be controlled by providing a temperature condition or an electrical condition to the patch PA.

The movement of a substance from the patch PA to the plate PL may depend on an extent of a contact area between the patch PA and the plate PL. For example, the substance movement efficiency between the patch PA and the plate PL may be increased or decreased in accordance with an extent of an area in which the patch PA and the plate PL come into contact.

When the patch PA includes a plurality of components, only some of the components may be selectively moved to the external plate PL. More specifically, a substance that binds specifically to some of the plurality of components may be fixed to the external plate PL. In this case, the substance fixed to the external plate PL may be in a liquid or solid state, or may be fixed to a different region. In this case, a portion of the substance of the plurality of components moves to the plate PL and binds specifically to the plate PL due to contact between the patch PA and the different region, and when the patch PA is separated from the plate PL, only some of the components may be selectively released to the plate PL.

Figure 5:
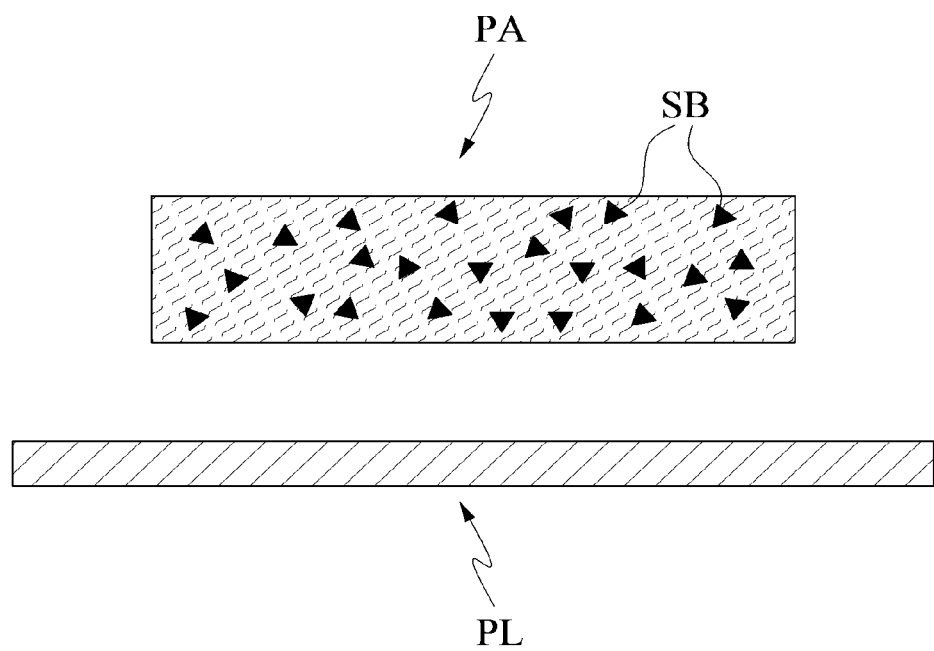
FIG. 5 illustrates providing of a substance as an example of a function of a patch according to the present application.
Figure 6:
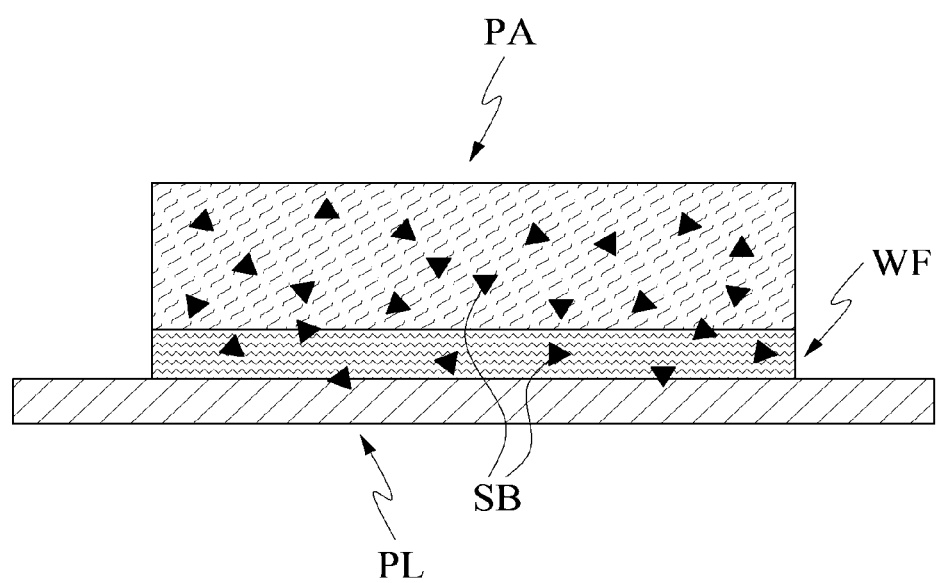
FIG. 6 illustrates providing of a substance as an example of a function of a patch according to the present application.
Figure 7:
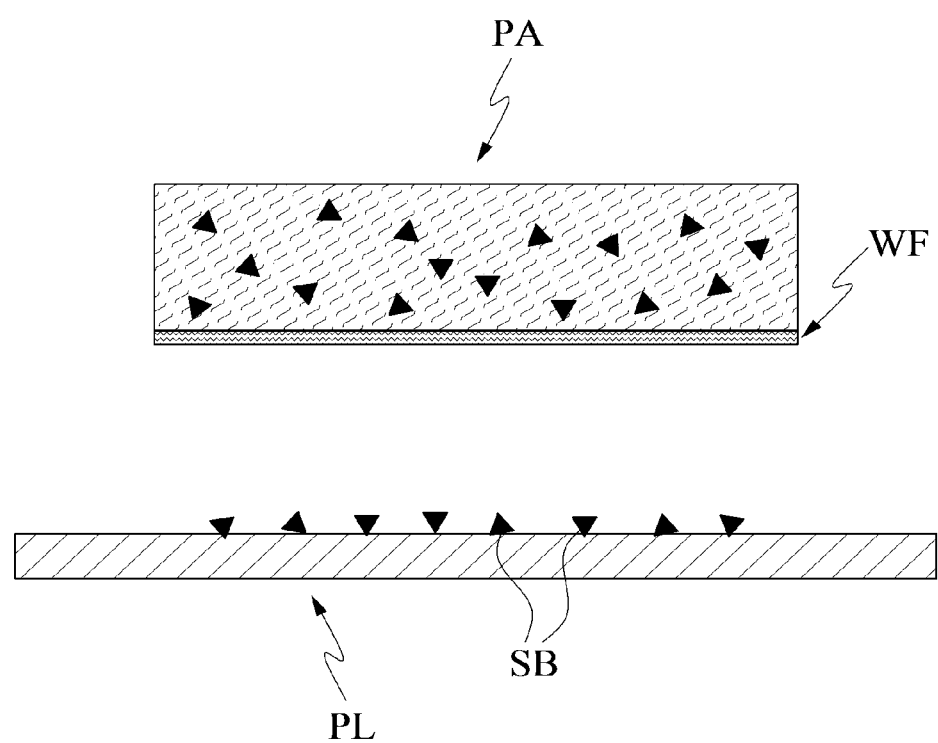
FIG. 7 illustrates providing of a substance as an example of a function of a patch according to the present application.

FIGS. 5 to 7 illustrate delivery of a substance from the patch PA to the external plate PL as an example of delivery of a substance from among the functions of the patch PA according to the present application. According to FIGS. 5 to 7, by the patch PA coming into contact with the external plate PL, a portion of a substance contained in the patch PA may be provided to the plate PL. In this case, providing of the substance may become possible by the patch PA coming into contact with the plate so that the substance is movable.

In this case, a water film WF may be formed in the vicinity of a contact surface at which the plate and the patch PA come into contact, and the substance may be movable through the formed water film WF.

Here, a case in which the liquid substance SB is provided from the patch PA to a substance having fluidity SL will be described. The substance having fluidity SL may be a liquid substance that is held in other containing space or that is flowing.

As the patch PA and the substance having fluidity come into contact (for example, the patch PA is put into a solution), at least a portion of the liquid substance SB captured in the patch PA may be diffused or moved due to irregular motion to the substance having fluidity SL. When the patch PA and the substance having fluidity SL are separated, a portion of the liquid substance SB that has been moved from the patch PA to the substance having fluidity become unable to move back to the patch PA so that a portion of the substance in the patch PA may be provided to the substance having fluidity.

The substance movement between the patch PA and the substance having fluidity SL may depend on an extent of a contact area between the patch PA and the substance having fluidity SL. For example, the substance movement efficiency between the patch PA and the substance having fluidity SL may be increased or decreased in accordance with an extent of an area at which the patch PA and the substance having fluidity SL come into contact (for example, a depth at which the patch PA is immersed into a solution or the like).

The substance movement between the patch PA and the substance having fluidity SL may be controlled through physical separation between the patch PA and the substance having fluidity.

A partial concentration of the additive substance AS in the liquid substance SB and a partial concentration of the additive substance AS in the substance having fluidity may be different, and the additive substance AS may be provided from the patch PA to the substance having fluidity.

However, in the patch PA providing the liquid substance SB to the substance having fluidity SL, the physical separation between the patch PA and the substance having fluidity SL is not essential. For example, when a force (driving force/casual force) that causes a substance to move from the patch PA to a liquid having fluidity disappears or is decreased to a reference value or lower, the movement of the substance may be stopped.

In "delivery" between the patch PA and the substance having fluidity SL, the above-described "delivery condition" between the patch PA and the substance having fluidity SL may not be required. It may be understood that substances that have already moved to the substance having fluidity SL are diffused and/or moved due to irregular motion in the substance having fluidity SL, and the substance has been provided to the substance having fluidity SL when a distance between the moved substance and the patch PA become larger a predetermined distance. Since, while in the case of the plate PL, a movable range expanded due to the contact is extremely limited, and thus the attractive force between the patch PA and the substances that have moved to the plate PL may be significant, in the relationship between the patch PA and the substance having fluidity, a movable range expanded due to contact between the patch PA and the plate PL is relatively much wider, and thus the attractive force between the patch PA and the substances that have moved to the substance having fluidity SL is insignificant.

Figure 8:
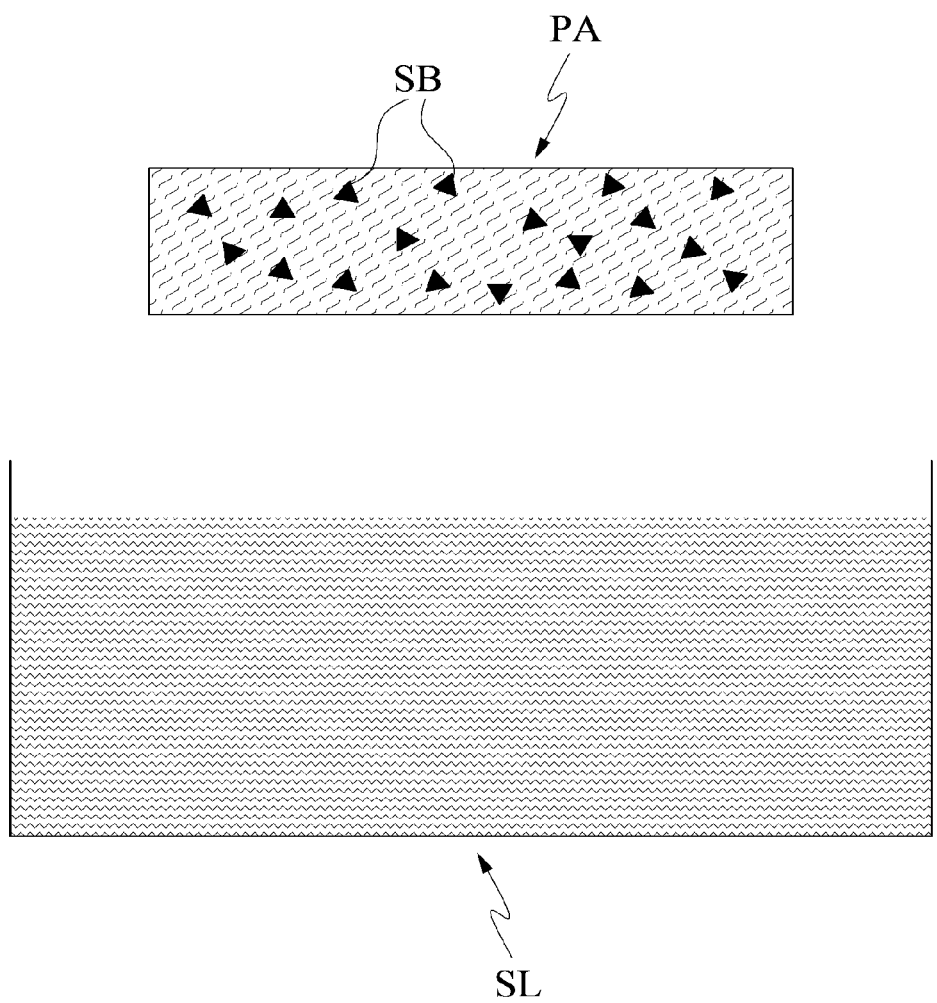
FIG. 8 illustrates providing of a substance as an example of a function of a patch according to the present application.
Figure 9:
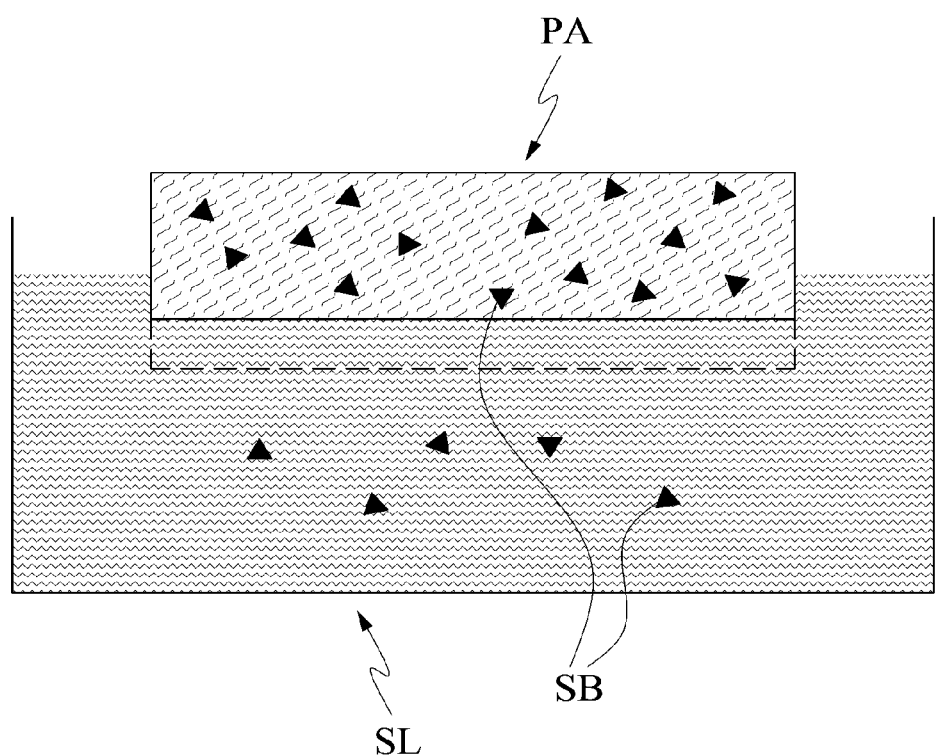
FIG. 9 illustrates providing of a substance as an example of a function of a patch according to the present application.
Figure 10:
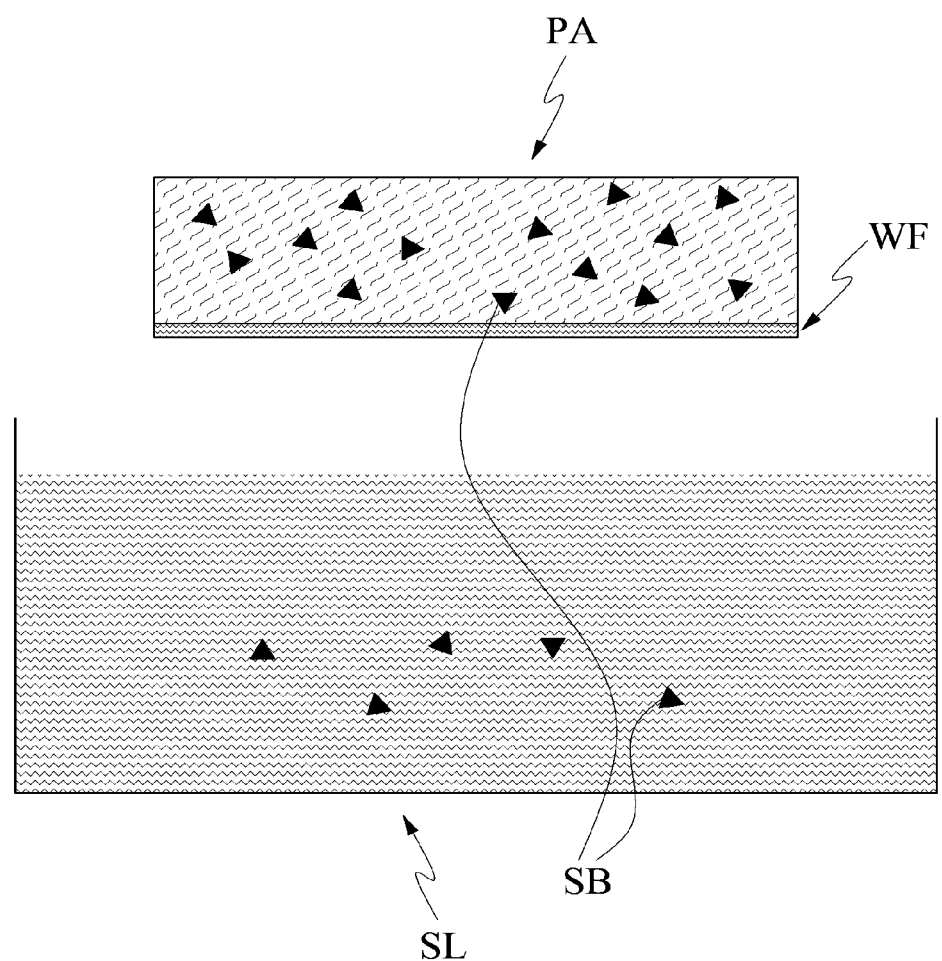
FIG. 10 illustrates providing of a substance as an example of a function of a patch according to the present application.

FIGS. 8 to 10 illustrate delivery of a substance from the patch PA to the substance having fluidity as an example of delivery of a substance from among the functions of the patch PA according to the present application. According to FIGS. 8 to 10, the patch PA may deliver a portion of a substance contained in the patch PA to an external substance having fluidity. The delivery of the portion of the contained substance may be performed by the patch PA being inserted into or coming into contact with the substance having fluidity so that substance movement is possible between the liquid substance SB captured in the patch PA and the substance having fluidity.

Here, it is assumed that a substance is moved from the patch PA to another patch PA. In a contact region in which the patch PA and the other patch PA are in contact, at least a portion of the liquid substance B provided in the patch PA may be moved to the other patch PA.

In the contact region, the liquid substance SB provided in each patch PA may be diffused and moved to the other patch PA. In this case, due to the movement of the substance, a concentration of the liquid substance SB provided in each patch PA may be changed. Also in the present embodiment, as described above, the patch PA and the other patch PA may be separated, and a portion of the liquid substance SB in the patch PA may be provided to the other patch PA.

The substance movement between the patch PA and the other patch PA may be performed through a change in an environmental condition including a change in a physical state.

The substance movement between the patch PA and another patch PA may depend on an extent of a contact area between the patch PA and the other patch PA. For example, the substance movement efficiency between the patch PA and the other patch PA may be increased or decreased in accordance with an extent of an area where the patch PA comes into contact with the other patch PA.

Figure 11:
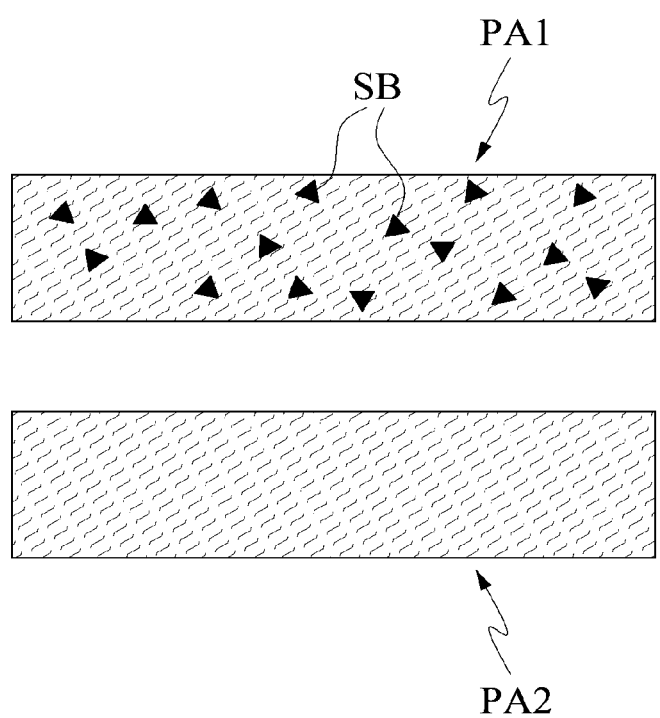
FIG. 11 illustrates providing of a substance as an example of a function of a patch according to the present application.
Figure 12:
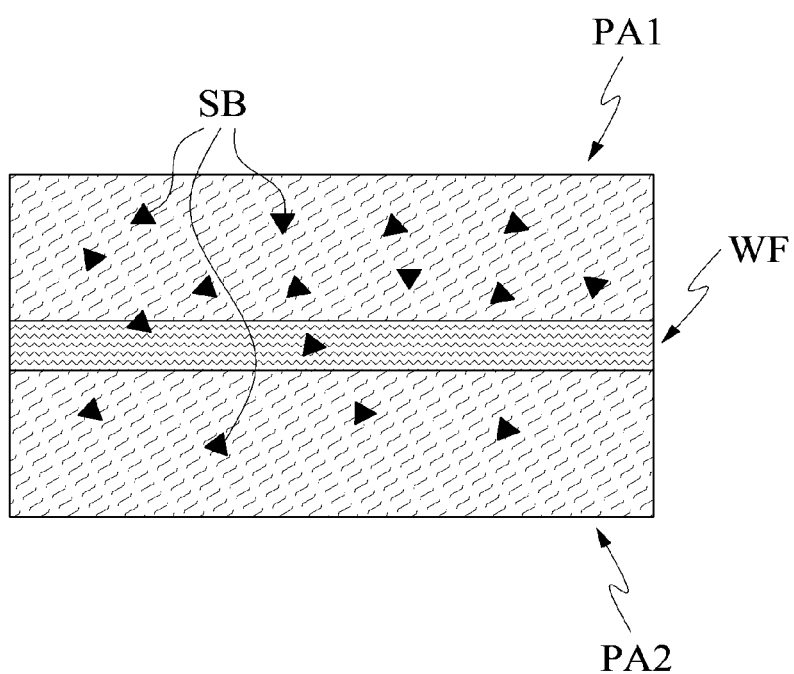
FIG. 12 illustrates providing of a substance as an example of a function of a patch according to the present application.
Figure 13:
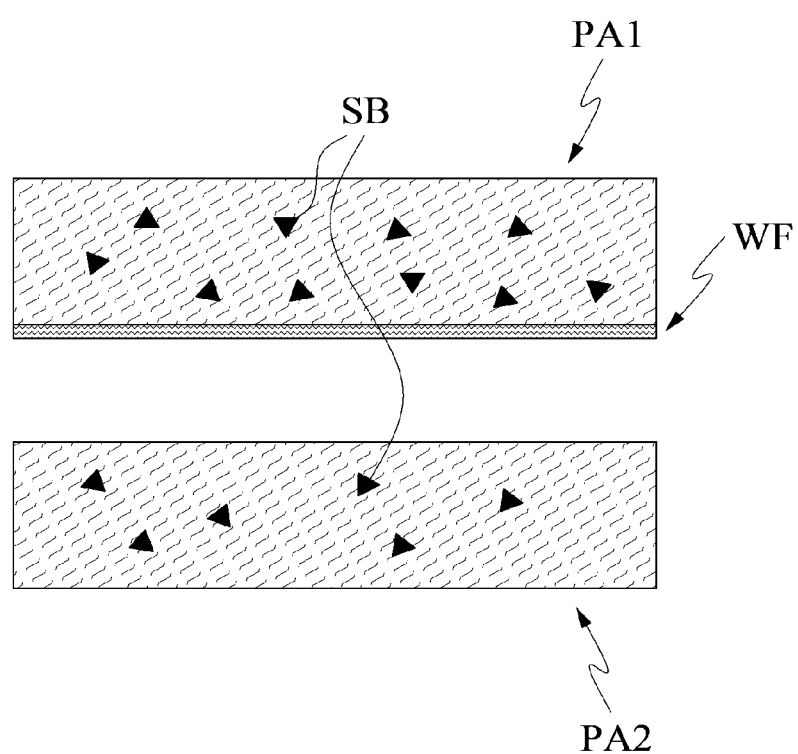
FIG. 13 illustrates providing of a substance as an example of a function of a patch according to the present application.

FIGS. 11 to 13 illustrate delivery of a substance from a patch PA1 to another patch PA2 as an example of delivery of a substance among the functions of the patch PA according to the present application. According to FIGS. 11 to 13, the patch PA1 may deliver a portion of a substance contained in the patch PA1 to the other patch PA2. The delivery of the portion of the substance may be performed by the patch PA1 coming into contact with the other patch PA2 and becoming a state in which a liquid substance SB captured in the patch PA1 and a substance captured in the other patch PA2 are exchangeable.

2.2.4.2 Absorption

Prior to description, it should be noted that, among the functions of the patch PA according to the present application, "absorption" may be managed similarly as the above-described "delivery" in some embodiments. For example, in a case in which a substance moves due to a concentration differences between substances, the "absorption" may be similar to the "delivery" in that a concentration of the liquid substance SB, particularly, a concentration of the additive substance AS, may be changed to control a direction in which the substance is moved. The "absorption" may also be similar to "delivery" in terms of controlling movement and selective absorption of a substance through a release of physical contact with the patch PA, and this may be clearly understood by those of ordinary skill in the art to which the present application pertains.

Due to the above-described characteristics, the patch PA according to the present application may capture an external substance. The patch PA may pull in an external substance present outside a region defined by the patch PA toward a region affected by the patch PA. The pulled external substance may be captured along with the liquid substance SB of the patch PA. The pulling of the external substance may be caused by an attractive force between the external substance and the liquid substance SB already captured in the patch PA. Alternatively, the pulling of the external substance may be caused by an attractive force between the external substance and a region of the mesh structural body NS not occupied by the liquid substance SB. The pulling of the external substance may be caused by a force of surface tension.

Hereinafter, for convenience, the above-described function of the patch PA will be referred to as "absorption." Absorption may be understood as a concept subordinate to the above-described channeling function of the patch PA, the concept defining movement of an external substance to the patch PA.

The absorption may occur by the patch PA via a state in which the substance is movable and a state in which the substance is immovable.

A substance that is absorbable by the patch PA may be in a liquid or solid state. For example, when the patch PA comes into contact with an external substance including a solid state substance, absorption of the substance may be performed due to an attractive force between the solid state substance included in the external substance and the liquid substance SB placed in the patch PA. As another example, when the patch PA comes into contact with a liquid external substance, the absorption may be performed due to binding between the liquid external substance and the liquid substance SB placed in the patch PA.

The external substance absorbed into the patch PA may be moved to the inside of the patch PA through the microcavities of the mesh structural body NS forming the patch PA or may be distributed on a surface of the patch PA. Positions at which the external substance is distributed may be set on the basis of a molecular weight or a particle size of the external substance.

While the absorption is performed, the form of the patch PA may be changed. For example, the volume, color, and the like of the patch PA may be changed. While the absorption into the patch PA is being performed, the absorption into the patch PA may be activated or delayed by adding external conditions such as a temperature change and a physical state change to an absorption environment of the patch PA.

The absorption will be described below as a function of the patch PA according to some examples of an external region that provides a substance to be absorbed into the patch PA when the absorption occurs.

Hereinafter, it will be assumed that the patch PA absorbs an external substance from a external plate PL. An example of the external plate may include a plate PL in which the external substance may be placed while the external substance is not absorbed thereinto.

A substance may be applied on the external plate PL. Particularly, a substance may be applied in a form of powder on the plate PL. The substance applied on the plate PL may be a single component or a mixture of a plurality of components.

The plate PL may have the shape of a flat plate. The shape of the plate PL may be deformed for improvement in ability to contain the substance or the like. For example, a well may be formed to improve the ability to contain the substance, a surface of the plate PL may be deformed by engraving or embossing, or a patterned plate PL may be used to improve contact with the patch PA.

The absorption of a substance from the plate PL by the patch PA according to the present application may be performed through contact between the plate PL and the patch PA. In this case, in a contact region in the vicinity of a contact surface between the plate PL and the patch PA, a water film WF may be formed due to the liquid substance SB captured in the patch PA and/or the substance applied on the plate PL. When the water film (aquaplane, hydroplane) WF is formed in the contact region, the substance applied on the plate PL may be captured by the water film WF. The substance captured in the water film WF may freely flow within the patch PA.

When the patch PA is spaced a predetermined distance or more apart and separated from the plate PL, the water film WF may be moved along with the patch PA, and the substance applied on the plate PL may be absorbed into the patch PA. The substance applied on the plate PL may be absorbed into the patch PA as the patch PA is separated a predetermined distance or more apart from the plate PL. When the patch PA and the plate PL are spaced apart and separated, the liquid substance SB provided to the patch PA may not be moved to the plate PL, or only an insignificant amount thereof may be absorbed into the patch PA.

A portion of or the entire substance applied on the plate PL may react specifically with a portion of or the entire substance captured in the patch PA. In this respect, absorption of a substance from the plate PL by the patch PA may be selectively performed. Particularly, the absorption may be performed selectively when the patch PA has a stronger attractive force than the plate PL with respect to a portion of the substance captured in the patch PA.

As an example, a portion of the substance may be fixed to the plate PL. In other words, a portion of the substance may be fixed to the plate PL while another portion of the substance is applied to have fluidity or not be fixed. In this case, when the patch PA and the plate PL are brought into contact and separated, the substance, excluding the portion of the substance fixed to the plate PL of the substance applied on the plate PL, may be selectively absorbed into the patch PA. Instead, the selective absorption may also occur due to polarities of a substance placed on the plate PL and a substance captured in the patch PA regardless of whether the substance is fixed.

As another example, when the liquid substance SB captured in the patch PA is bound specifically to at least a portion of a substance applied on the plate PL, only the portion of the substance applied on the plate PL bound specifically to the liquid substance SB may be absorbed into the patch PA when the patch PA is brought into contact with and then separated from the substance applied on the plate PL.

As yet another example, a portion of the substance applied on the plate PL may react specifically with a substance fixed to the plate PL in advance. In this case, only a remaining substance, excluding the substance that reacts specifically with the substance fixed to the plate PL in advance of the substance being applied to the plate PL, may be absorbed into the patch PA.

Figure 14:
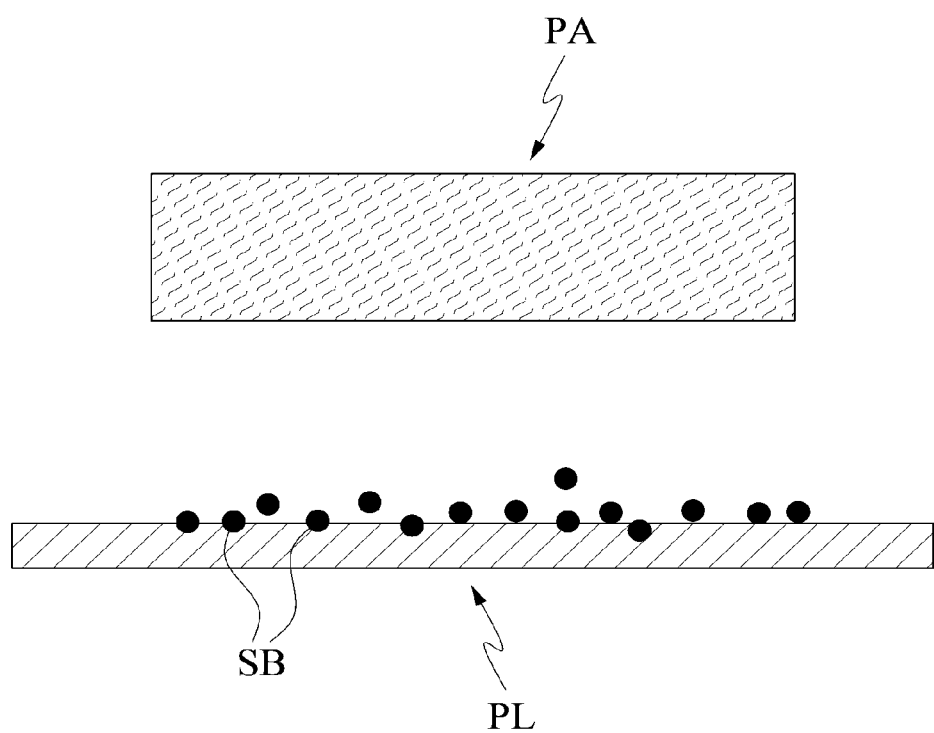
FIG. 14 illustrates absorbing of a substance as an example of a function of a patch according to the present application.
Figure 15:
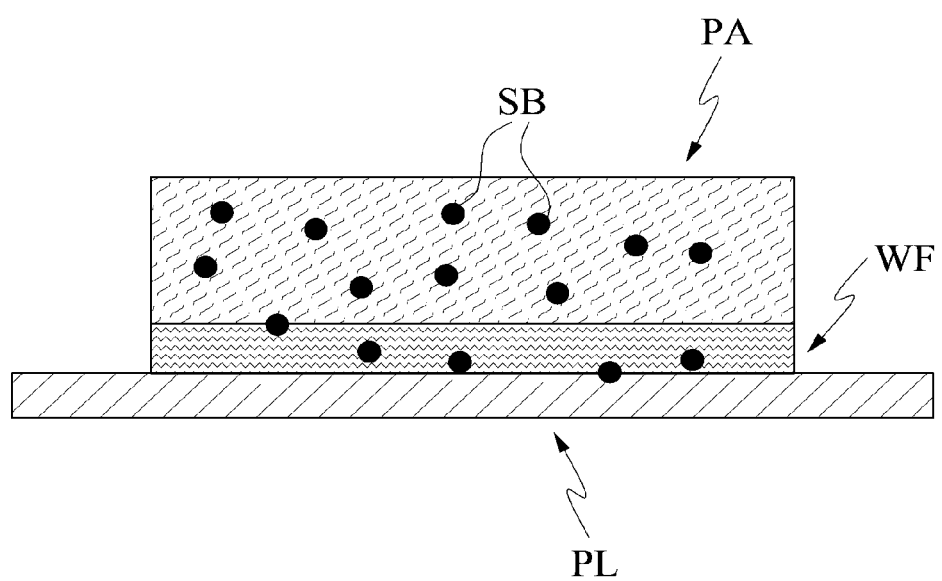
FIG. 15 illustrates absorbing of a substance as an example of a function of a patch according to the present application.
Figure 16:
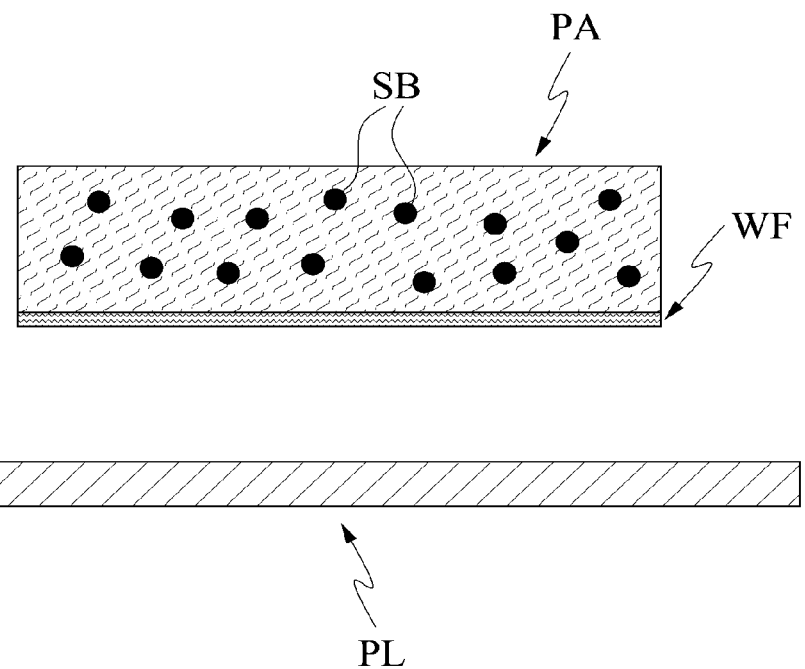
FIG. 16 illustrates absorbing of a substance as an example of a function of a patch according to the present application.

FIGS. 14 to 16 illustrate absorption of a substance from an external plate PL by the patch PA as an example of absorption of a substance from among the functions of the patch PA according to the present application. According to FIGS. 14 to 16, the patch PA may absorb a portion of a substance placed on the external plate PL from the external plate PL. The absorption of the substance may be performed by the patch PA coming into contact with the external plate PL, the water film WF being formed in the vicinity of a contact region between the external plate PL and the patch PA, and the substance being movable to the patch PA through the water film WF.

Here, it will be assumed that a substance is absorbed into the patch PA from the substance having fluidity SL. The substance having fluidity SL may refer to a liquid external substance that is held in other containing space or that is flowing. More specifically, by having an environment in which the substance having fluidity SL and the liquid substance SB captured in the patch PA may flow to and from each other, a portion of or the entire substance having fluidity SL may be absorbed into the patch PA. In this case, the environment in which the substance having fluidity SL and the liquid substance SB may flow to and from each other may be formed by the patch PA coming into contact with at least a portion of the substance having fluidity SL.

When the patch PA comes into contact with the substance having fluidity SL, the patch PA may be in a state in which a substance is movable from the substance having fluidity SL. When the patch PA is separated from the substance having fluidity SL, at least a portion of the substance having fluidity SL may be absorbed into the patch PA.

The absorption of a substance into the patch PA from the substance having fluidity SL may depend on a concentration difference between the substance captured in the patch PA and the substance having fluidity SL. In other words, when the concentration of the liquid substance SB captured in the patch PA with respect to a predetermined additive substance AS is lower than the concentration of the substance having fluidity SL with respect to the predetermined additive substance AS, the predetermined additive substance AS may be absorbed into the patch PA.

When a substance is absorbed into the patch PA from the substance having fluidity SL, in addition to the absorption depending on the concentration difference while the patch PA and the substance having fluidity SL are in contact as described above, the absorption into the patch PA may also be controlled by adding an electrical factor or changing a physical condition. Further, without direct contact between the substance captured in the patch PA and a substance to be absorbed, the absorption of a substance may also be performed through indirect contact therebetween via a medium.

Figure 17:
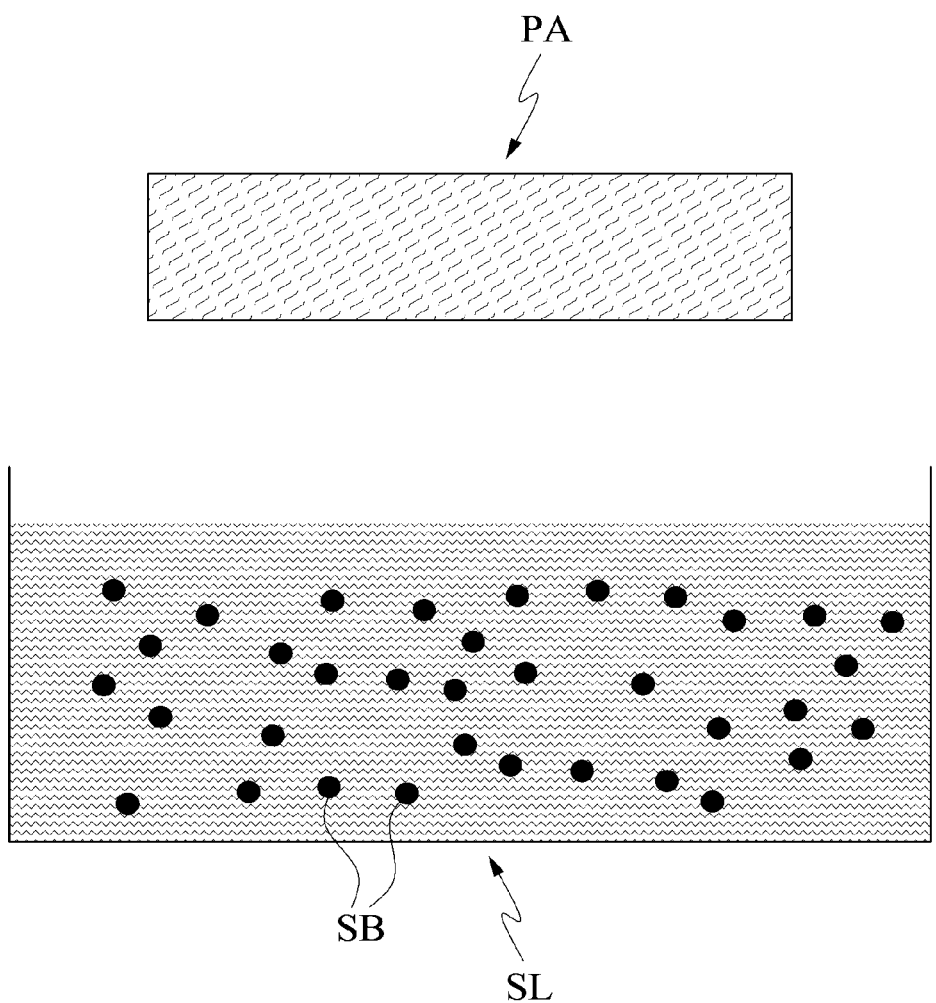
FIG. 17 illustrates absorbing of a substance as an example of a function of a patch according to the present application.
Figure 18:
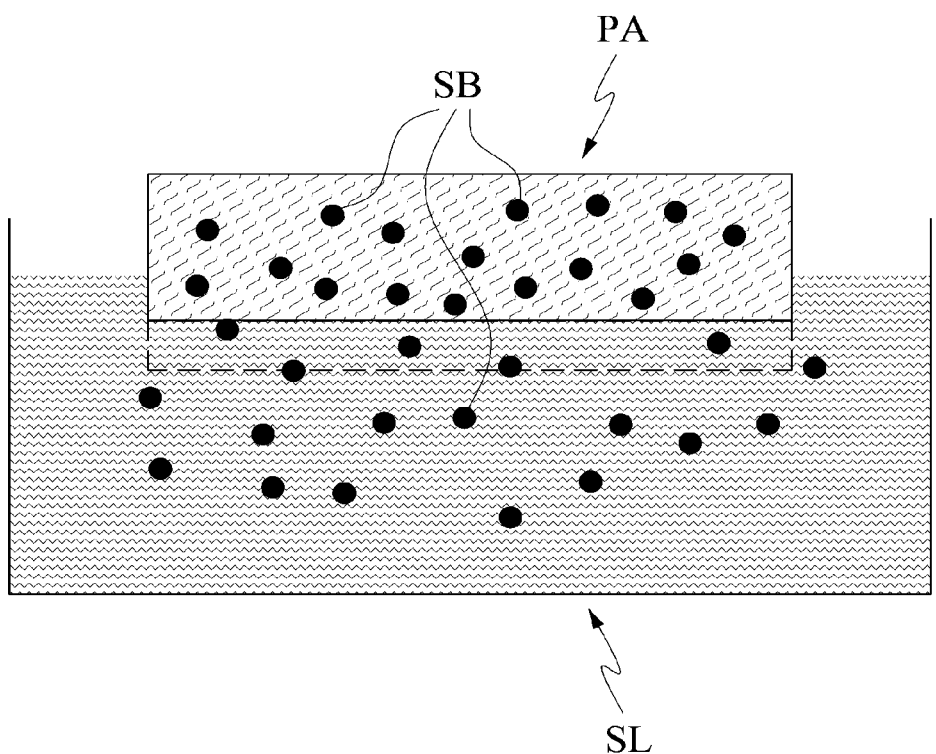
FIG. 18 illustrates absorbing of a substance as an example of a function of a patch according to the present application.
Figure 19:
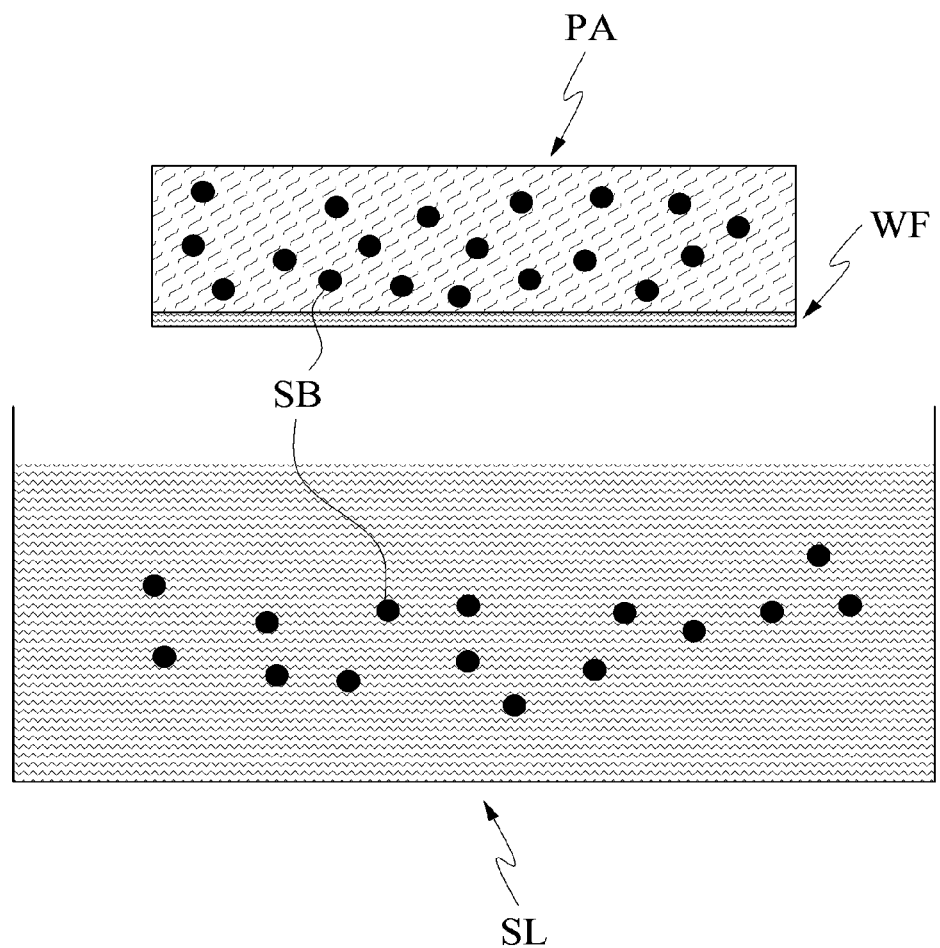
FIG. 19 illustrates absorbing of a substance as an example of a function of a patch according to the present application.

FIGS. 17 to 19 illustrate absorption of a substance from the substance having fluidity SL by the patch PA as an example of absorption of a substance from among the functions of the patch PA according to the present application. According to FIGS. 17 to 19, the patch PA may absorb a portion of the substance having fluidity SL. The absorption of a substance may be performed by the patch PA being immersed into the substance having fluidity SL or coming into contact with the substance having fluidity SL so that the liquid substance SB captured in the patch PA and the substance having fluidity SL are movable to and from each other.

Here, it will be assumed that the patch PA absorbs an external substance from another patch PA.

The absorption of an external substance from another patch PA by the patch PA may be performed due to a difference in binding force between the absorbed external substance and the substance already captured in the patch PA and between the absorbed external substance and the external substance not absorbed into the patch PA. For example, when the absorbed substance exhibits hydrophilic property, the patch PA exhibits hydrophilic property, and an attractive force between the absorbed substance and the patch PA is stronger than an attractive force between the other patch PA and the absorbed substance (that is, when the patch PA is more hydrophilic than the other patch PA), at least a portion of the external substance may be absorbed into the patch PA when the patch PA and the other patch PA are separated after being brought into contact.

Figure 20:
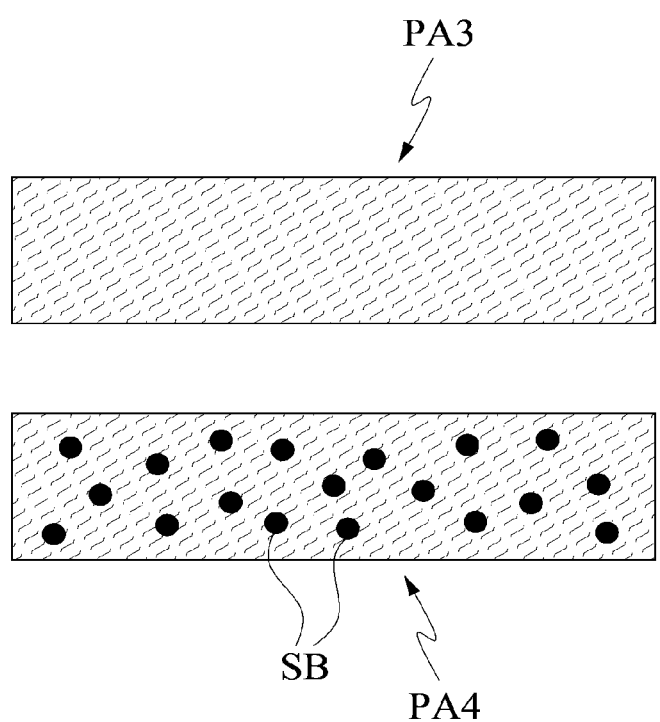
FIG. 20 illustrates absorbing of a substance as an example of a function of a patch according to the present application.
Figure 21:
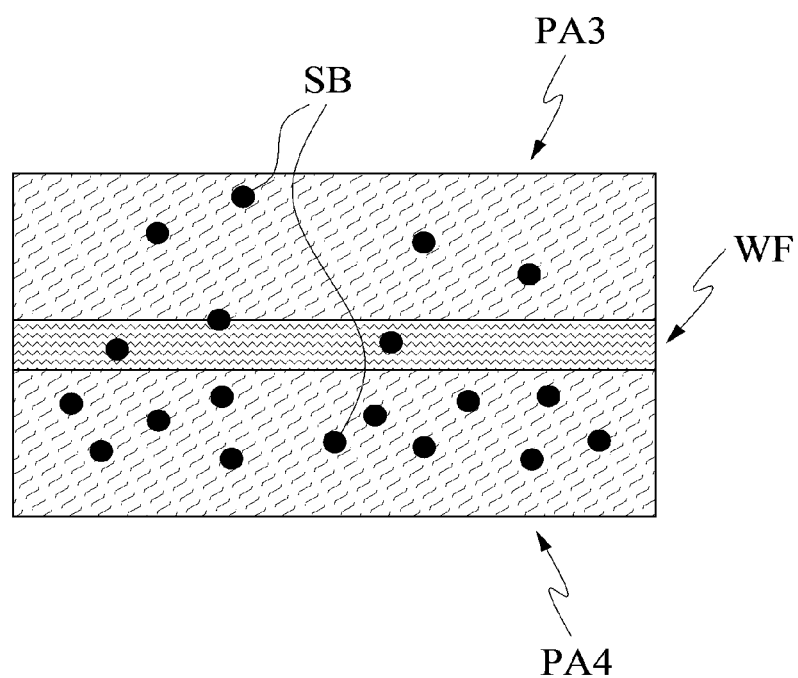
FIG. 21 illustrates absorbing of a substance as an example of a function of a patch according to the present application.
Figure 22:
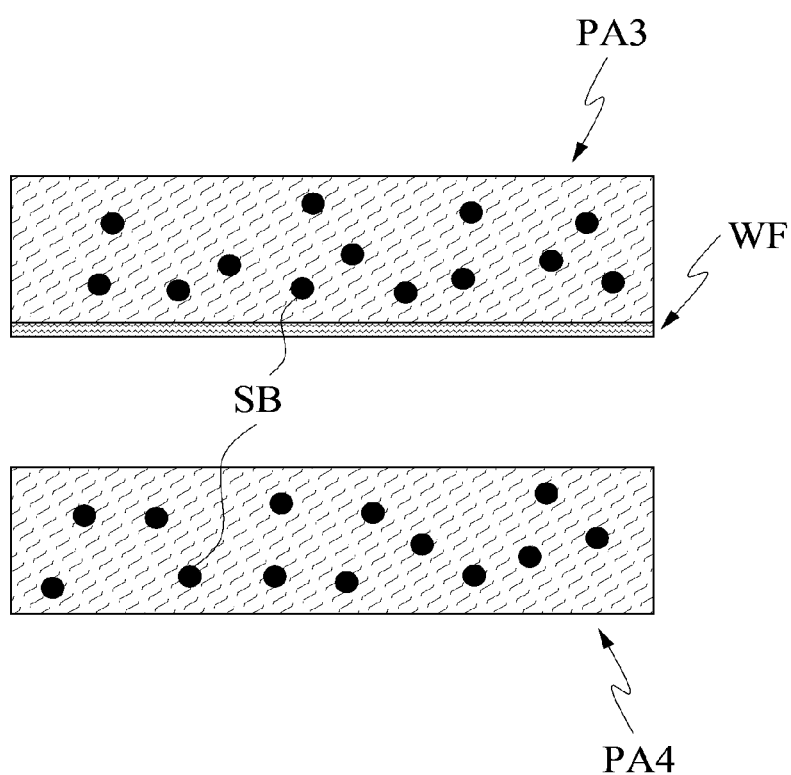
FIG. 22 illustrates absorbing of a substance as an example of a function of a patch according to the present application.

FIGS. 20 to 22 illustrate absorption of a substance from another patch PA4 by a patch PA3 as an example of absorption of a substance among the functions of the patch PA according to the present application. According to FIGS. 20 to 22, the patch PA3 may absorb a portion of a substance placed in the other patch PA4. The absorption of the substance may be performed by the patch PA3 coming into contact with the other patch PA4 so that a liquid substance SB captured in the patch PA3 and a liquid substance SB captured in the other patch PA4 are exchangeable.

A binding force of the patch PA to the external substance absorbed thereinto may be changed in accordance with a proportion of a frame structural body of the three-dimensional mesh structural body NS constituting the patch PA with respect to the total volume of the patch PA. For example, as the proportion of a volume occupied by the frame structural body in the entire patch PA increases, the amount of substance captured in the structural body may be reduced. In this case, a binding force between the patch PA and a target substance may be reduced due to a reason such as reduction in a contact area between the target substance and the substance captured in the patch PA.

In relation to this, ratios of materials that constitutes the mesh structural body NS may be adjusted during manufacturing process of the patch PA so that polarity of the patch PA is controlled. For example, in the case of a patch PA manufactured using agarose, a concentration of the agarose may be controlled to adjust a degree of the absorption.

When the certain region has a weaker binding force than the patch PA with respect to a substance provided from the patch PA, and the patch PA and another patch PA are brought into contact and then separated, the absorbed external substance may be separated from the other patch PA along with the patch PA.

2.2.4.3 Providing of Environment

Due to the above-described characteristics, the patch PA according to the present application may perform a function of adjusting an environmental condition of a desired region. The patch PA may provide an environment due to the patch PA to the desired region.

The environmental condition due to the patch PA may depend on the liquid substance SB captured in the patch PA. The patch PA may create a desired environment in a substance placed in an external region on the basis of characteristics of a substance accommodated in the patch PA or for a purpose of making the environment correspond to characteristics of the substance accommodated in the patch PA.

The adjustment of the environment may be understood as changing an environmental condition of the desired region. The changing of the environmental condition of the desired region may be implemented in a form in which a region affected by the patch PA is expanded to include at least a portion of the desired region or a form in which an environment of the patch PA is shared with the desired region.

Hereinafter, for convenience, the above-described function of the patch PA will be referred to as "providing of an environment."

The providing of an environment by the patch PA may be performed in a state in which a substance is movable between the patch PA and an external region subject to provide the environment. The providing of an environment by the patch PA may be performed through contact. For example, when the patch PA comes into contact with a desired region (for example, an external substance, a plate PL, or the like), a specific environment may be provided to the desired region by the patch PA.

The patch PA may adjust an environment of a target region TA by providing an environment with an appropriate pH, osmotic pressure, humidity level, concentration, temperature, and the like. For example, the patch PA may provide fluidity(liquidity) to the target region TA or a target substance. Such providing of fluidity may occur due to movement of a portion of a substance captured in the patch PA. A moist environment may be provided to the target region TA through the liquid substance SB or the base substance BS captured in the patch PA.

The environmental factors provided by the patch PA may be constantly maintained in accordance with a purpose. For example, the patch PA may provide homeostasis to the desired region. As another example, as a result of providing an environment, the substance captured in the patch PA may be adapted to an environmental condition of the desired region The providing of an environment by the patch PA may result from diffusion of the liquid substance SB included in the patch PA. That is, when the patch PA and the desired region come into contact, a substance may be movable through a contact region that is formed due to contact between the patch PA and the desired region. In relation to this, an environmental change due to an osmotic pressure, an environmental change due to a change in ionic concentration, providing of a moist environment, and a change in a pH level may be implemented in accordance with a direction in which the substance is diffused.

Figure 23:
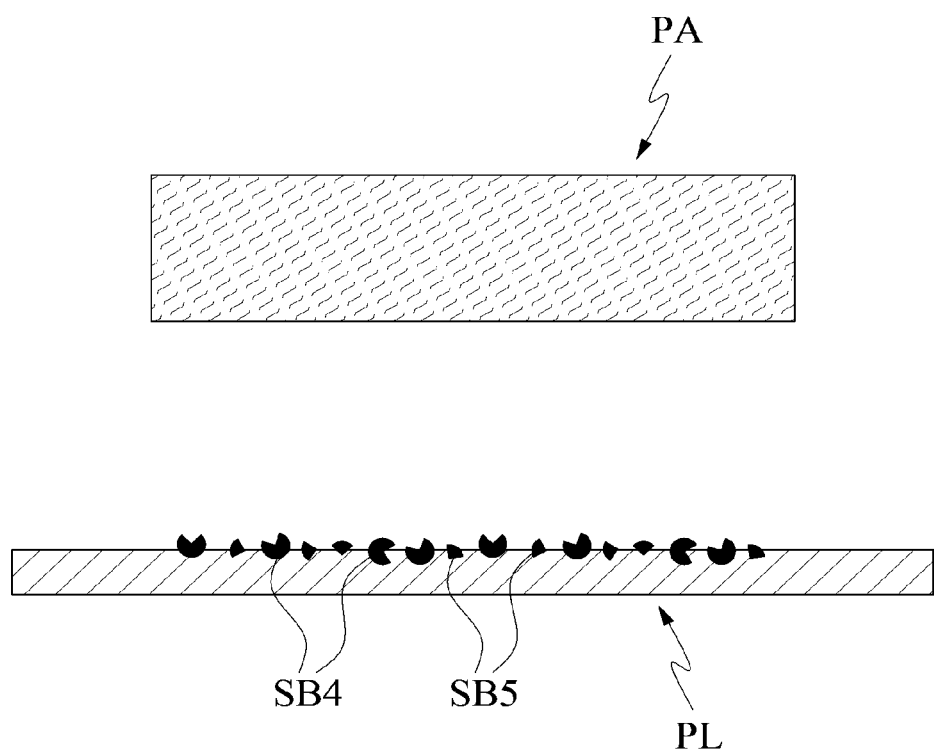
FIG. 23 illustrates providing of an environment as an example of a function of a patch according to the present application.
Figure 24:
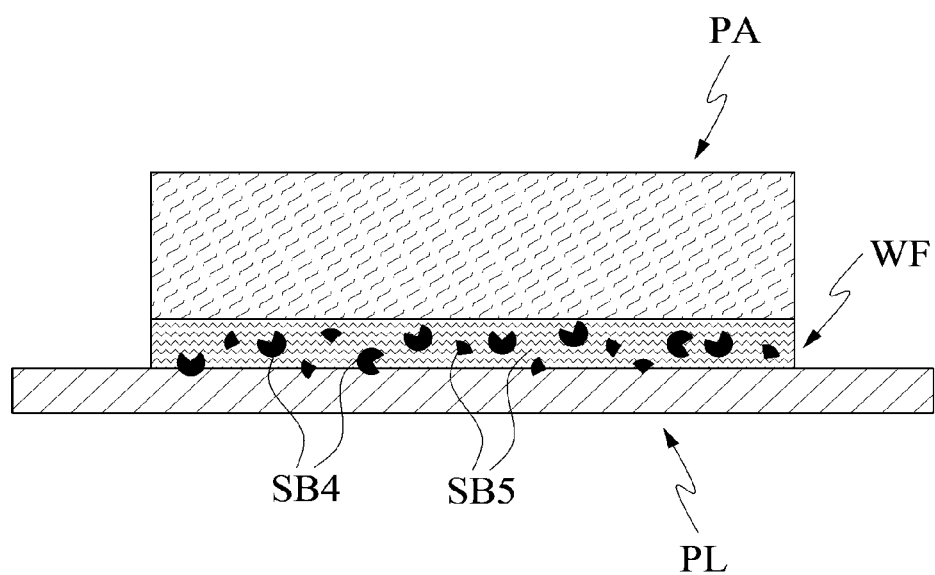
FIG. 24 illustrates providing of an environment as an example of a function of a patch according to the present application.
Figure 25:
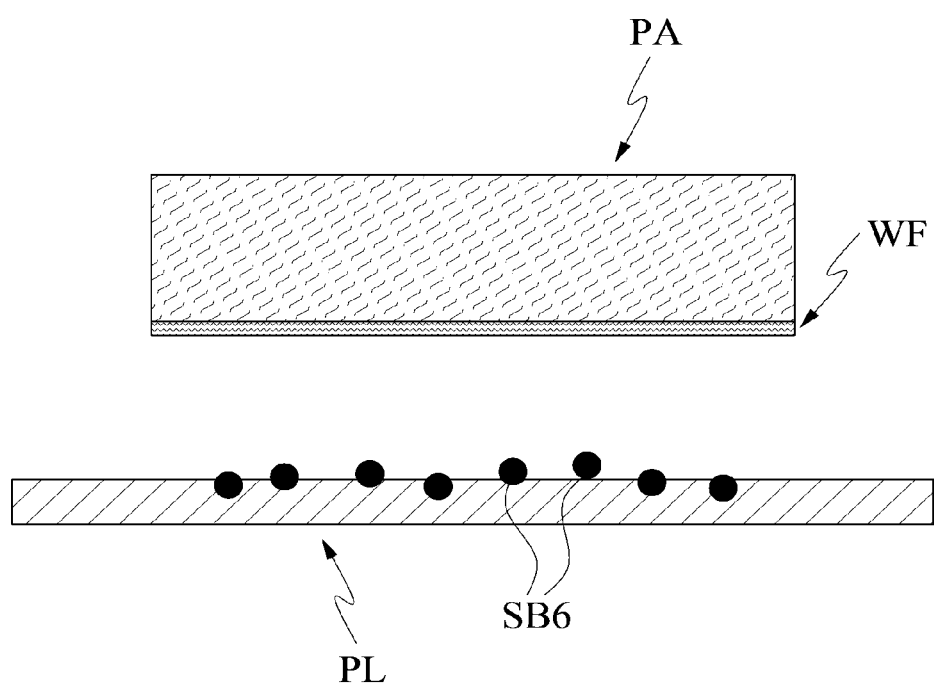
FIG. 25 illustrates providing of an environment as an example of a function of a patch according to the present application.

FIGS. 23 to 25 illustrate providing of a predetermined environment to an external plate PL by the patch PA as an example of providing of an environment among the functions of the patch PA according to the present application. According to FIGS. 23 to 25, the patch PA may provide a predetermined environment to an external plate PL on which a fourth substance SB4 and a fifth substance SB5 are placed. For example, the patch PA may provide a predetermined environment to the plate PL for the fourth substance SB4 and the fifth substance SB5 to react and form a sixth substance SB6. The providing of the environment may be performed by the patch PA coming into contact with the plate PL so that a water film WF is formed in the vicinity of a contact region and the fourth substance SB4 and the fifth substance SB5 are captured in the water film WF.

3. Application of Patch

The patch PA according to the present application may be implemented to perform various functions by suitably applying the above-described functions of the patch PA.

The technical spirit of the present application will be described below by disclosing some embodiments. However, the technical scope to which functions of the patch PA disclosed by the present application are applied may be interpreted in a broad sense within the scope that may be easily derived by those of ordinary skill in the art, and the scope of the present application should not be interpreted as being limited by the embodiments disclosed herein.

3.1. In-Patch

The patch PA may provide a reaction region for a substance. In other words, a reaction of a substance may occur in at least a portion of a spatial region affected by the patch PA. In this case, the reaction of a substance may be a reaction between liquid substances SB captured in the patch PA and/or a reaction between the captured liquid substance SB and a substance provided from the outside of the patch PA. The providing of a reaction region for a substance may activate or promote a reaction of a substance.

In this case, the liquid substance SB captured in the patch PA may include at least one of a substance added upon manufacturing the patch PA, a substance additive into the patch PA after the manufacturing of the patch PA and contained in the patch PA, and a substance temporarily captured in the patch PA. In other words, regardless of a form in which a substance is captured in the patch PA, any substance captured in the patch PA at a time point at which a reaction in the patch PA is activated may react in the patch PA. Further, a substance injected after the manufacturing of the patch PA may also act as a reaction initiator.

The providing of a reaction region for a reaction related to the liquid substance SB captured in the patch PA may be a concept subordinate, in terms of embodiment, to the above-described Section 2.1.3 (that is, providing of reaction space). Alternatively, the providing of a reaction region for a reaction related to the liquid substance SB captured in the patch PA may consist of multiple concepts that perform combined functions of the above-described Section 2.1.3 and Section 2.2.4.2 (that is, absorption). The providing of a reaction region for a reaction related to the liquid substance SB captured in the patch PA is not limited thereto and may be implemented in the form in which two or more functions are combined.

3.1.1 First Embodiment

Hereinafter, description will be given by assuming that the function of absorption into the patch PA and the function of providing of a reaction space (hereinafter referred to as "providing function") are performed by a single patch PA. In this case, the absorption function and the providing function may be simultaneously-performed functions, functions performed at different time points, or functions sequentially performed to perform another function. The patch PA further including other functions in addition to the absorption and providing functions may also be considered as belonging to the present embodiment.

As described above, the patch PA may perform a function of capturing a substance, and the substance may have fluidity even when the substance is captured. When some components of the liquid substance SB are non-uniformly distributed, the non-uniform components may be diffused. Even when components of the liquid substance SB are uniformly distributed, the liquid substance SB may have a predetermined level of mobility due to irregular motion of particles. In this case, a reaction between substances, for example, specific binding between substances, may occur inside the patch PA.

For example, in the patch PA, in addition to a reaction between captured substances, a reaction in a form in which a substance having fluidity that is newly captured in the patch PA and the substance that has been captured in the patch PA bind specifically to each other may also be possible.

The reaction between the substance having fluidity and the substance that has been captured in the patch PA may also occur after the substance patch being separated from an space that has been provided. For example, after the patch PA absorbs the substance having fluidity from an arbitrary space, the patch PA may be separated from the arbitrary space, and a reaction between the absorbed substance and the substance that has been captured in the patch PA may occur in the patch PA.

In addition, the patch PA may allow a reaction of a substance captured therein to occur by performing the absorption function with respect to a substance having fluidity. In other words, the absorption of the substance having fluidity by the patch PA may act as a trigger for a reaction between the absorbed substance and the substance that has been captured in the patch PA. The reaction may occur inside a space defined by the patch PA.

A composition of the liquid substance SB captured in the patch PA may be changed due to the reaction occurring inside the patch PA. When, particularly, a substance captured inside the patch PA is a compound, a chemical composition thereof may be changed before and after a reaction. Alternatively, a composition distribution of a substance may be changed in accordance with a position of the substance in the patch PA. For example, this may be due to diffusion or particles having an attractive force specific to another substance.

When the composition of the liquid substance SB is changed due to a reaction inside the patch PA, a portion of the substance may be absorbed into the patch PA due to a concentration difference between the patch PA and a substance outside the patch PA (when a substance in contact with the patch PA is present, the corresponding substance), or the substance may be released from the patch PA to the substance outside the patch PA.

3.1.2 Second Embodiment

Hereinafter, an embodiment in which the containing function of the patch PA and the function of providing of a reaction space for a substance are performed together for at least a predetermined amount of time will be described. More specifically, the patch PA may perform a function of providing a space for at least a portion of the liquid substance SB contained in the patch PA to react.

The patch PA may contain a substance and provide a reaction space for the contained substance. In this case, the reaction space provided by the patch PA may be the microcavities formed by the mesh structural body NS of the patch PA or a surface region of the patch PA. Particularly, when a substance contained in the patch PA and a substance applied on a surface of the patch PA react, the reaction space may be the surface region of the patch PA.

The reaction space provided by the patch PA may serve to provide a specific environmental condition. While a reaction occurs in the liquid substance SB placed in the patch PA, an environmental condition of the reaction may be adjusted by the patch PA. For example, the patch PA may serve as a buffer solution.

By containing a substance through a mesh structure, the patch PA does not require a container, separately. When the reaction space of the patch PA is a surface of the patch PA, a reaction may be easily observed through the surface of the patch PA. For this, the shape of the patch PA may be deformed into a shape that facilitates the observation.

The liquid substance SB contained in the patch PA may be denaturalized or react with a different type of substance. The composition of the liquid substance SB contained in the patch PA may be changed with time.

The reaction may refer to a chemical reaction in which a chemical formula is changed, a physical state change, or a biological reaction. In this case, the liquid substance SB contained in the patch PA may be a substance formed of a single component or a mixture including a plurality of components.

3.2 Providing of Movement Path (Channeling)

Hereinafter, the patch PA that performs a function of providing a substance movement path will be described. More specifically, as described above, the patch PA may capture, absorb, release, and/or contain a substance having fluidity. Various embodiments of the patch PA that performs the function of providing a substance movement path may be implemented by each of the above-described functions of the patch PA or a combination thereof. However, a few embodiments will be disclosed for a better understanding.

3.2.1 Third Embodiment

The patch PA may be implemented to perform functions described in Section 2.2.4.1 (that is, the section related to delivery) and Section 2.2.4.2 (that is, the section related to absorption) among the above-described functions of the patch PA. In this case, the absorption function and the delivery function may be provided together or sequentially provided.

The patch PA may perform the absorption and delivery functions together to provide a substance movement path. Particularly, the patch PA may absorb an external substance and provide the absorbed external substance to an external region, thereby providing a movement path to the external substance.

The providing of the movement path of the external substance by the patch PA may be performed by absorbing the external substance and releasing the external substance. More specifically, the patch PA may come into contact with the external substance, absorb the external substance, come into contact with the external region, and deliver the external substance to the external region. In this case, the capturing of the external substance and the delivery of the captured external substance to the external region by the patch PA may be performed through a process similar to those of the above-described absorption and delivery.

The external substance absorbed into the patch PA and provided may be in a liquid phase or a solid phase.

In this way, the patch PA may allow a portion of the external substance to be provided to another external substance. The external substance and the other external substance may simultaneously come into contact with the patch PA. The external substance and the other external substance may come into contact with the patch PA at different time points.

The external substance and the other external substance may come into contact with the patch PA at different time points. When the external substances come into contact with the patch PA at different time points, the external substance may come into contact with the patch PA first, and after the external substance and the patch PA are separated, the patch PA and the other external substance may come into contact. In this case, the patch PA may temporarily contain a substance captured from the external substance.

The patch PA may simultaneously provide a substance movement path and additionally provide a time delay. The patch PA may perform a function of suitably adjusting an amount of substance provided to another external substance and a speed of such providing.

Such a series of processes may be carried out in one direction with respect to the patch PA. As a specific example, absorption of a substance may be performed through a surface of the patch PA, an environment may be provided in an inner space of the patch PA, and the substance may be released through another surface facing the surface.

3.2.2 Fourth Embodiment

The patch PA may perform the absorbing and releasing of a substance among the above-described functions of the patch PA and the providing of a reaction space for the substance simultaneously. In this case, the absorption and release of the substance and the providing of the reaction space may be performed simultaneously or sequentially.

According to an embodiment, in performing the processes of absorbing and releasing an external substance, the patch PA may provide a reaction space to the absorbed external substance for at least a predetermined amount of time. The patch PA may provide a specific environment for at least some time to the liquid substance SB captured in the patch PA, including the absorbed external substance.

The liquid substance SB that has been captured in the patch PA and the external substance captured in the patch PA may react inside the patch PA. The external substance absorbed into the patch PA may be affected by an environment provided by the patch PA. The substance released from the patch PA may include at least a portion of a substance generated through the reaction. The external substance may be released from the patch PA after the composition, characteristics, and the like of the external substance are changed.

The absorbed substance may be released from the patch PA. The external substance being absorbed into the patch PA and being released from the patch PA may be understood as the external substance passing through the patch PA. The external substance that has passed through the patch PA may lose integrity due to a reaction inside the patch PA or an influence of an environment provided by the patch PA.

The above-described processes of absorption of an external substance, reaction of a substance, and providing of the substance may be carried out in one direction. In other words, the absorption of a substance may be performed at one position of the patch PA, the providing of an environment may be performed at another position of the patch PA, and the release of the substance may be performed at yet another position of the patch PA.

Figure 26:
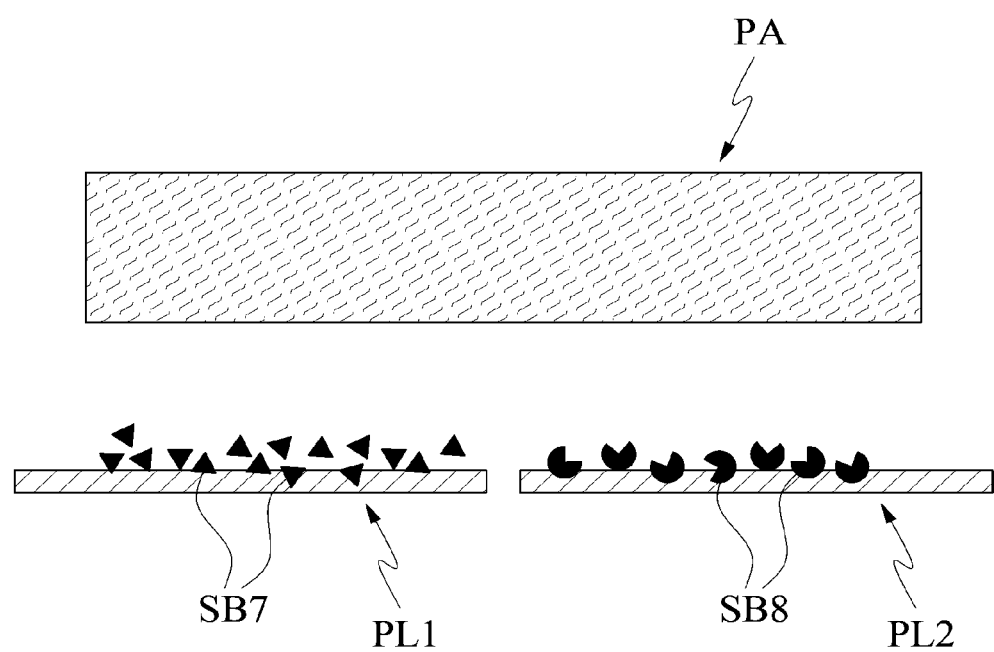
FIG. 26 illustrates performance of absorbing and providing of a substance as an embodiment of a patch according to the present application.
Figure 27:
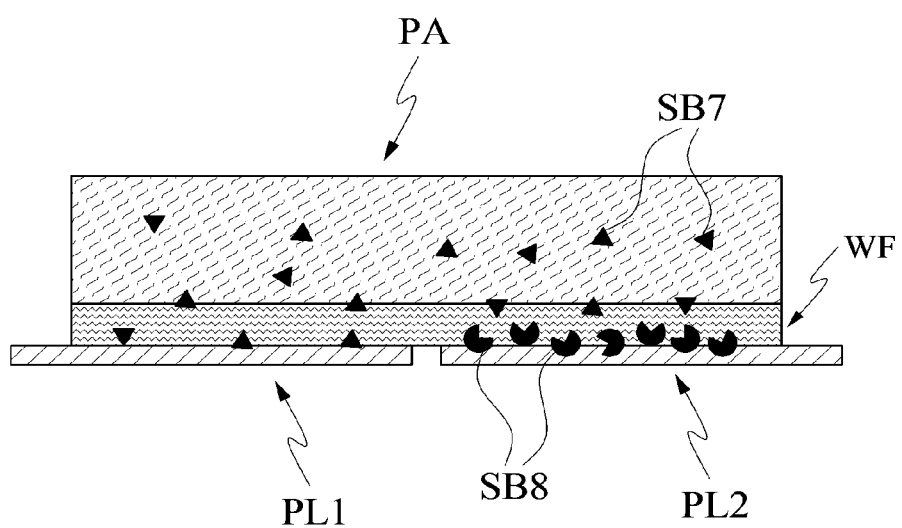
FIG. 27 illustrates performance of absorbing and providing of a substance as an embodiment of a patch according to the present application.
Figure 28:
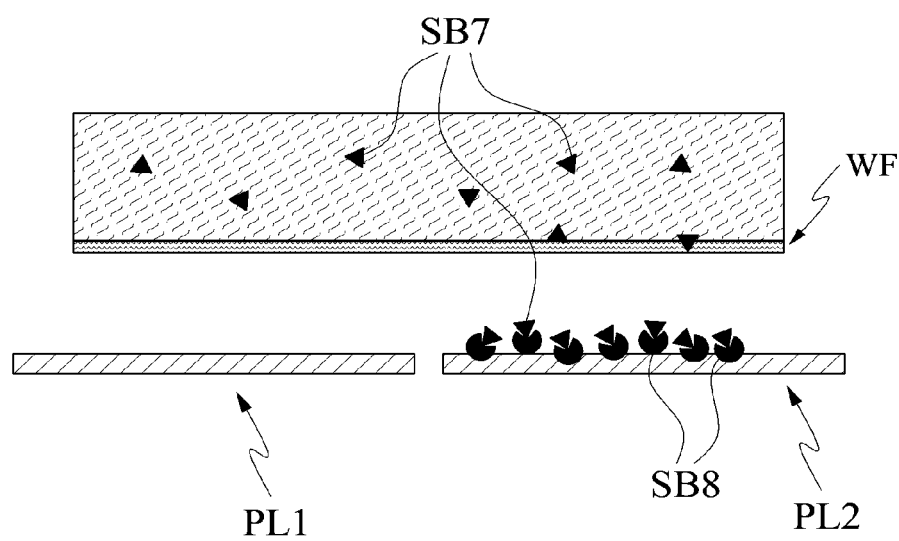
FIG. 28 illustrates performance of absorbing and providing of a substance as an embodiment of a patch according to the present application.

FIGS. 26 to 28 illustrate providing of a substance movement path between two plates PL as an embodiment of the patch PA according to the present application. According to FIGS. 26 to 28, the patch PA may provide a substance movement path between a plate PL1 on which a seventh substance SB7 is applied and a plate PL2 on which an eighth substance SB8 is applied. As a specific example, when the seventh substance SB7 is capable of binding to the eighth substance, and the eighth substance is fixed to the plate PL2, the patch PA may come into contact with the plates PL1 and PL2 so that the seventh substance SB7 is moved through the patch PA and bound to the eighth substance SB8. The seventh substance SB7 and the eighth substance SB8 may be connected to the patch PA through a water film WF formed by the patch PA coming into contact with the plates PL1 and PL2.

Figure 29:
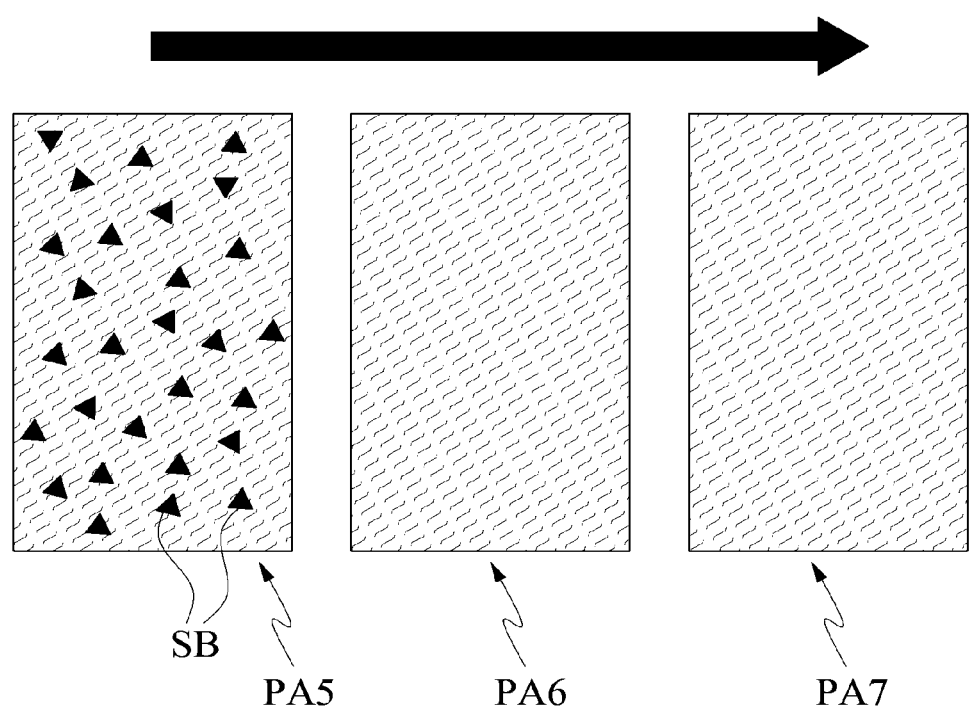
FIG. 29 illustrates performance of absorbing and providing of a substance as an embodiment of a patch according to the present application.
Figure 30:
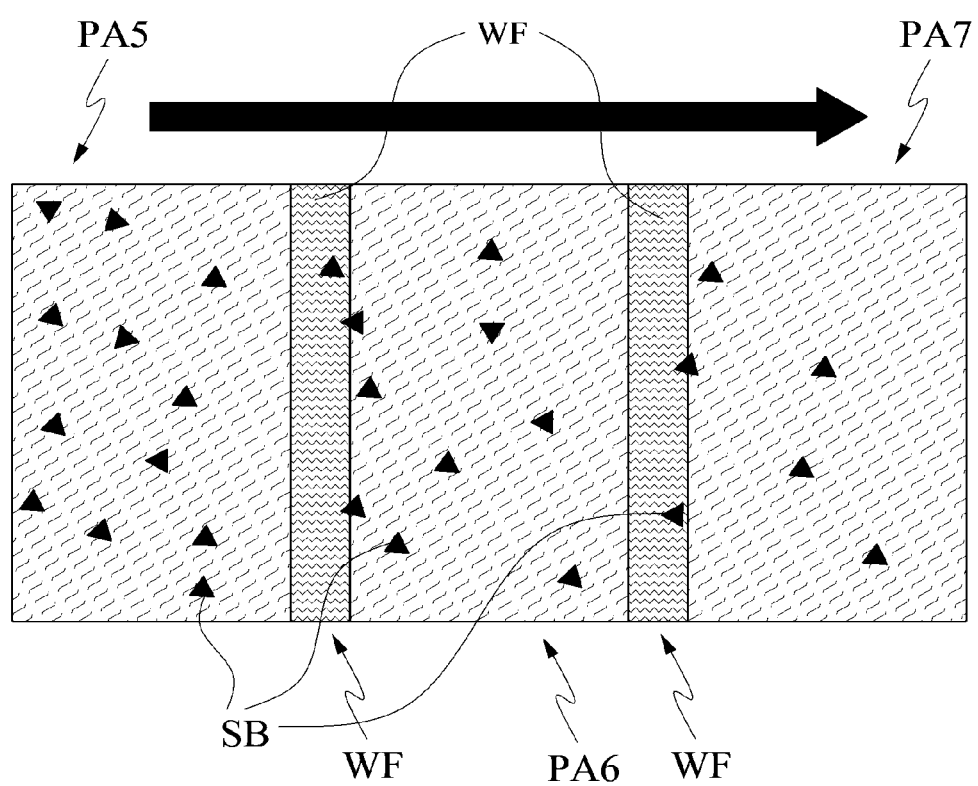
FIG. 30 illustrates performance of absorbing and providing of a substance as an embodiment of a patch according to the present application.

FIGS. 29 and 30 illustrate providing of a substance movement path between two patches as an embodiment of the patch PA according to the present application. According to FIGS. 29 and 30, a patch PA6 configured to provide the movement path may be in contact with a patch PA5 configured to contain a substance to be moved, and a patch PA7 configured to receive the substance to be moved. The patch PA6 configured to provide the movement path may come into contact with the patch PA5 configured to contain the substance to be moved and the patch PA7 configured to receive the substance to be moved, and the substance to be moved may be moved to the patch PA7 configured to receive the substance to be moved. The movement of the substance between the patches may be performed by a water film WF formed in the vicinity of a contact region between the patches.

Figure 31:
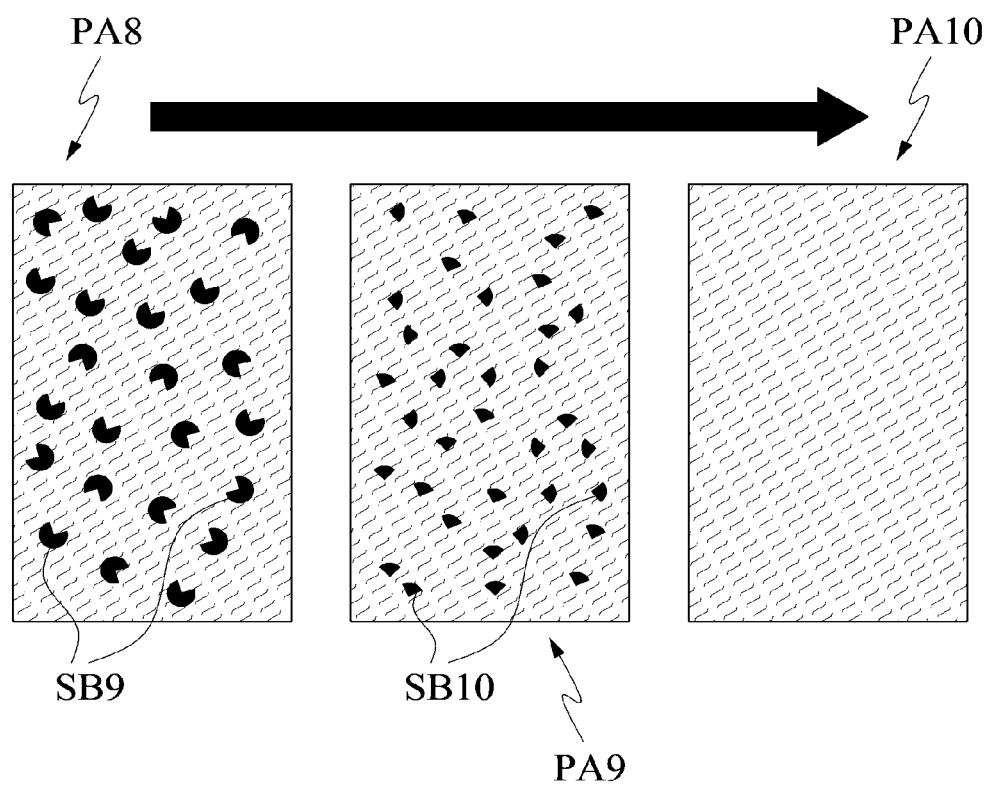
FIG. 31 illustrates performance of absorbing and providing of a substance and providing of an environment as an embodiment of a patch according to the present application.
Figure 32:
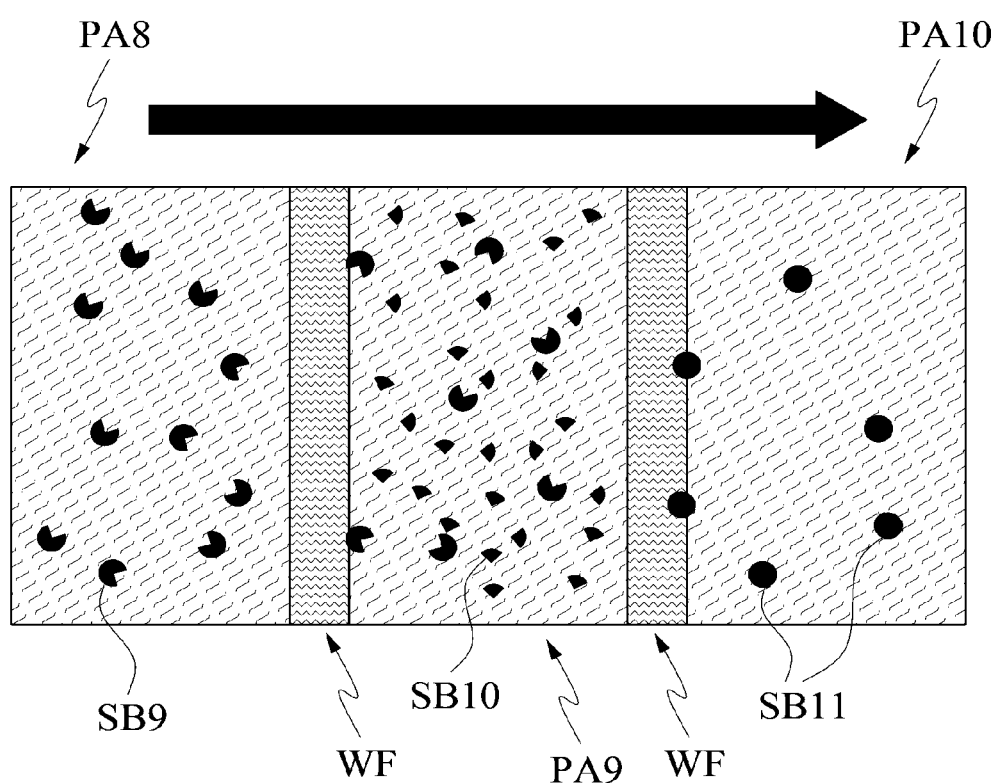
FIG. 32 illustrates performance of absorbing and providing of a substance and providing of an environment as an embodiment of a patch according to the present application.

FIGS. 31 and 32 illustrate providing of a substance movement path between two patches as an embodiment of the patch according to the present application. According to FIGS. 29 and 30, a patch PA9 configured to provide the movement path may be in contact with a patch PA8 configured to contain a ninth substance SB9 and a patch PA10 configured to receive a substance. The patch PA9 providing the movement path may come into contact with the patch PA8 configured to contain the ninth substance SB9 to absorb the ninth substance SB9. The absorbed ninth substance SB9 may react with a tenth substance SB10 contained in the patch PA9, which is configured to provide the movement path, and generate an eleventh substance. An eleventh substance SB11 may be provided from the patch PA9 configured to provide the movement path to the patch PA10 configured to receive the substance. The movement of a substance between the patches PA may be performed through a water film WF formed in the vicinity of a contact region between the patches PA.

3.3 Multi-Patch

A patch PA may be solely used, or a plurality of patches PA may be used together. In this case, the plurality of patches PA being able to be used together includes a case in which the plurality of patches PA are sequentially used as well as a case in which the plurality of patches PA are used simultaneously.

When the plurality of patches PA are used simultaneously, the patches PA may perform different functions. Although each patch PA of the plurality of patches PA may contain the same substance, the plurality of patches PA may also contain different substances.

When the plurality of patches PA are used simultaneously, the patches PA may not come into contact with each other such that substance movement does not occur between the patches PA, or a desired function may be performed in a state in which substances contained in the patches PA are exchangeable.

Although the plurality of patches PA used together may be manufactured in shapes similar to each other or in the same size, the plurality of patches PA may be used together even when the plurality of patches PA have different shapes. Each patch PA constituting the plurality of patches PA may be manufactured such that densities of the mesh structural bodies NS are different or components constituting the mesh structural bodies NS are different.

3.3.1 Contact with Plurality of Patches

When a plurality of patches PA are used, the plurality of patches PA may come into contact with a single target region TA. The plurality of patches PA may come into contact with the single target region TA and perform a desired function.

When a plurality of target regions TA are present, the plurality of patches PA may come into contact with different target regions TA. When the plurality of target regions TA are present, the plurality of patches PA may respectively come into contact with corresponding target regions TA and perform a desired function.

The plurality of patches PA may come into contact with a substance applied on the target region TA. In this case, the substance applied on the target region TA may be fixed or have fluidity.

The desired function may be a function of providing or absorbing the substance. However, each patch PA does not necessarily provide the same substance or absorb the same substance, and the patches PA may provide different substances to the target region TA or absorb different components from a substance placed in the target region TA.

The desired function may be different for each patch PA constituting the plurality of patches PA. For example, one patch PA may perform the function of providing a substance to the target region TA, and another patch PA may perform the function of absorbing the substance from the target region TA.

The plurality of patches PA may include different substances, and the different substances may be provided to a single target region TA and used to induce a desired reaction. When a plurality of components of a substance is required for the desired reaction to occur, the plurality of components may be contained in a plurality of patches PA respectively and provided to the target region TA. Such use of the plurality of patches PA may be particularly useful when properties of substances required for a desired reaction are lost or altered when the substances required for the reaction being mixed for reasons such as being contained in a single patch PA.

According to an embodiment, when the plurality of patches PA include substances formed of different components, and the substances formed of different components have different specific binding relationships, the substances formed of different components may be provided to the target region TA. The plurality of patches PA may be used to detect a plurality of specific bindings from the substances applied on the target region TA, by providing the substances including different components.

According to another embodiment, the plurality of patches PA may include substances formed of the same component, but each patch PA may have a different concentration with respect to the substance formed of the same component. The plurality of patches PA including the substances formed of the same component may come into contact with the target region TA and be used to determine an influence in accordance with a concentration of the substance included in the plurality of patches PA.

When the plurality of patches PA are used as described above, the patches PA may be grouped into more efficient forms and used. In other words, the configuration of the plurality of patches PA being used may be changed every time the plurality of patches PA are used. The plurality of patches PA may be manufactured in the form of a cartridge and used. In this case, the form of each patch PA being used may be suitably standardized and manufactured.

The plurality of patches PA in the form of a cartridge may be suitable when patches PA configured to contain a plurality of types of substances are manufactured to be used by being chosen as necessary.

Particularly, when attempting to detect a specific reaction of each substance from the target region TA using a plurality of types of substances, a combination of specific reactions to be detected may be changed every time the detection is performed.

Figure 33:
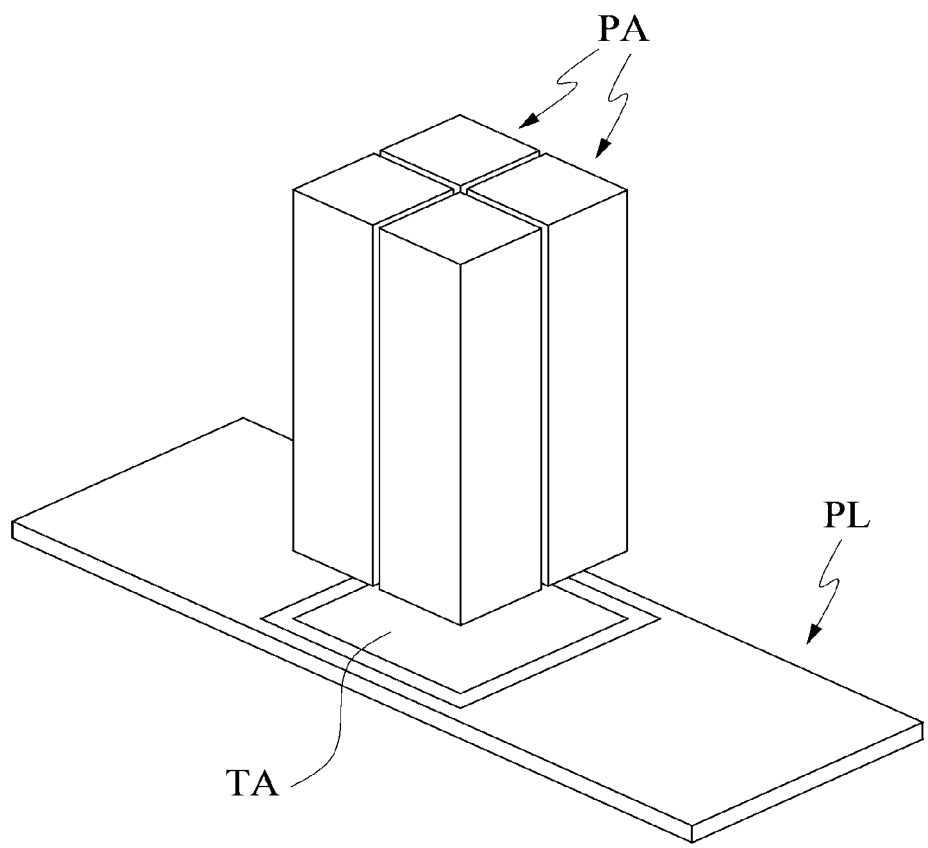
FIG. 33 illustrates an implementation of a plurality of patches as an embodiment of a patch according to the present application.

FIG. 33 illustrates a case in which the plurality of patches PA are used together as an embodiment of the patch PA according to the present application. According to FIG. 33, the plurality of patches PA according to an embodiment of the present application may simultaneously come into contact with a target region TA placed on a plate PL. The patches PA constituting the plurality of patches PA may have a standardized form. The plurality of patches PA may include a first patch and a second patch, and a substance contained in the first patch may be different from a substance contained in the second patch.

Figure 34:
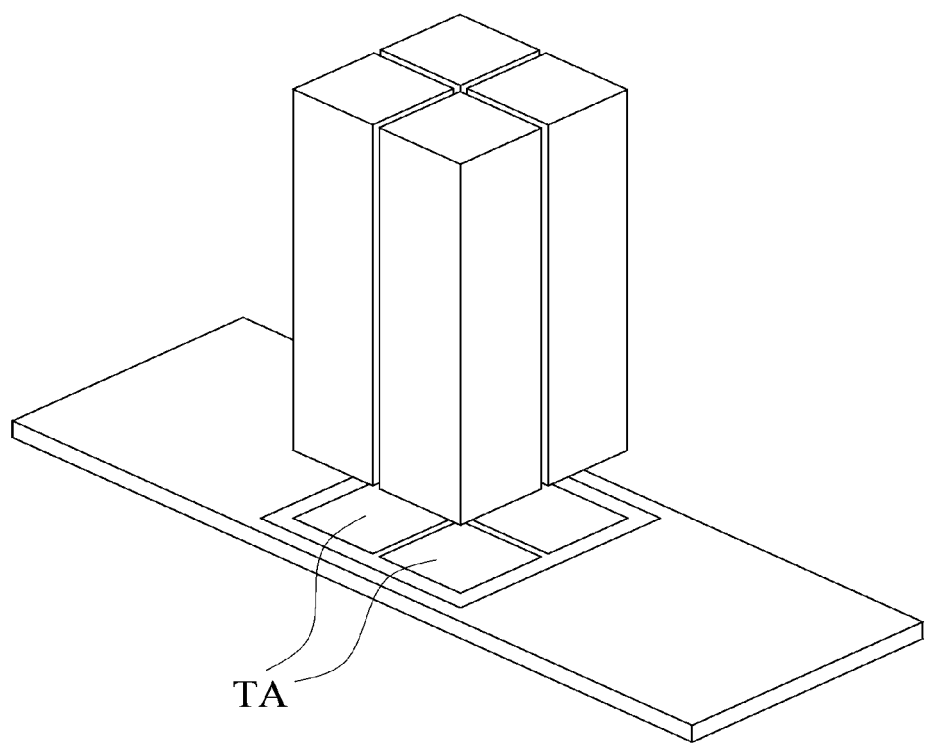
FIG. 34 illustrates an implementation of a plurality of patches and a plate having a plurality of target regions as an embodiment of a patch according to the present application.

FIG. 34 illustrates a case in which the plurality of patches PA are used and the plate PL includes a plurality of target regions TA. According to FIG. 34, the plurality of patches PA according to an embodiment of the present application may simultaneously come into contact with the plurality of target regions TA placed on the plate PL. The plurality of patches PA may include a first patch PA and a second patch PA, the plurality of target regions TA may include a first target region and a second target region, and the first patch may come into contact with the first target region and the second patch may come into contact with the second target region.

3.3.2 Fifth Embodiment

The plurality of patches PA may perform a plurality of functions. As described above, the patches PA may simultaneously perform a plurality of functions, and the patches PA may also simultaneously perform different functions. However, embodiments are not limited to the above, and the functions may also be combined and performed in the plurality of patches PA.

First, in the case in which the patches PA simultaneously perform the plurality of functions, the patches PA may perform both containing and release of a substance. For example, the patches PA may contain different substances and release substances contained in the target regions TA. In this case, the contained substances may be simultaneously or sequentially released.

Next, in the case in which the patches PA simultaneously perform different functions, the patches PA may separately perform containing and release of a substance. In this case, only some of the patches PA may come into contact with a target region TA and release a substance to the target region TA.

3.3.3 Sixth Embodiment

When a plurality of patches PA are used, as described above, the plurality of patches PA may perform a plurality of functions. First, the patches PA may simultaneously perform containing, releasing, and absorbing of substances. Alternatively, the patches PA may also separately perform the containing, releasing, and absorbing of the substances. However, embodiments are not limited thereto, and the functions may also be combined and performed in the plurality of patches PA.

For example, at least some of the plurality of patches PA may contain a substance and release the contained substance to the target region TA. In this case, at least a remainder of the plurality of patches PA may absorb a substance from the target region TA. Some of the plurality of patches PA may release a substance that binds specifically to a substance placed in the target region TA. In this case, specific binding may be detected by absorption of a substance that has not formed specific binding from the substance placed in the target region TA using another patch PA.

3.3.4 Seventh Embodiment

When a plurality of patches PA are used, the patches PA may simultaneously perform containing and release of a substance and providing of an environment. Alternatively, the patches PA may separately perform the containing and release of a substance and providing of an environment. However, embodiments are not limited thereto, and the functions may also be performed in combination in the plurality of patches PA.

For example, a patch PA among the plurality of patches PA may release a substance contained therein to the target region TA. In this case, another patch PA may provide an environment to the target region TA. Here, the providing of an environment may be implemented in the form in which an environmental condition of a substance contained in the other patch PA is provided to the target region TA. More specifically, a reacting substance may be provided to the target region TA by the patch PA, and the other patch PA may come into contact with the target region TA and provide a buffering environment.

As another example, the plurality of patches PA may be in contact with each other. In this case, at least one patch PA may contain a substance and release the substance contained therein to another patch PA configured to provide an environment. In the present embodiment, the patch PA configured to provide an environment may release a substance, come into contact with at least one other patch PA that is not in contact with the patch PA configured to provide an environment, and absorb a substance from the patch PA.

4. Generals for PCR

PCR refers to a polymerase chain reaction, which is a method of amplifying a target genetic material that is desired to be detected. PCR is used in various fields such as disease diagnosis (e.g., cancer diagnosis, acquired immunodeficiency syndrome (AIDS) diagnosis, tuberculosis diagnosis), gene replication, forensic evidence, and gene identification.

Figure 35:
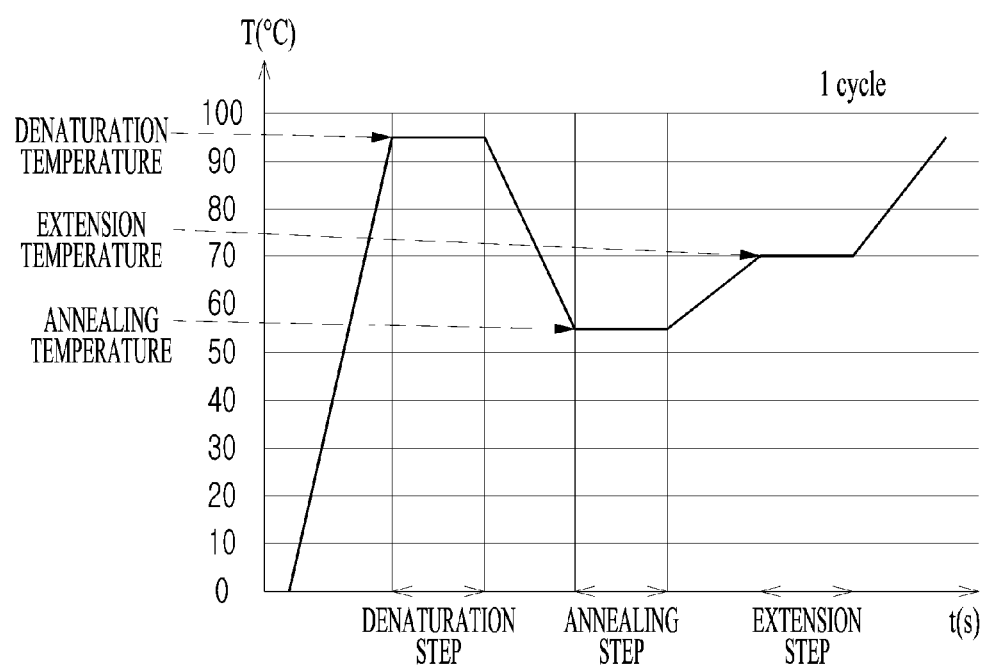
FIG. 35 is a graph for describing a polymerase chain reaction (PCR) process according to the present application.

FIG. 35 is a graph for describing a PCR process according to the present application.

Generally, a PCR may include three steps. Specifically, a general PCR may consist of: 1) a denaturation step in which the double helix DNA structure is separated using heat; 2) an annealing step in which a primer is be able to bind to an end of a DNA sequence that is desired to be amplified; and 3) an extension step in which a DNA bound with the primer, is elongated.

The denaturation step is a process in which double strands of DNA forming the double helix structure are separated into two single strands of DNA. In the denaturation step, a test object (hereinafter, "sample") is normally heated to 95° C. to break a hydrogen bond formed between complementary bases of the double strands of DNA. In this way, the double strands of DNA may be separated into a pair of single strands of DNA. Hereinafter, temperature at which the double strands of DNA can be separated into a pair of single strands of DNA (e.g., 95° C.) will be defined as a "denaturation temperature."

The annealing step is a process in which a complementary primer binds to a base sequence of a single strand of DNA. The annealing step is normally performed at a temperature in the range of 55 to 65° C., and a primer that corresponds to a part of sequences of a target genetic material may be used. The primer may include a forward primer and a reverse primer, and the forward primer and the reverse primer may have complementary base sequences. The primer may have been labeled with a fluorescent substance. Hereinafter, temperature at which a primer complementary to a base sequence of the single strand of DNA may bind to a single strand of DNA (e.g., 55 to 65° C.) will be defined as an "annealing temperature."

The extension step is a process in which a complementary base is synthesized on the single strand of DNA bound to the primer so that the single strand of DNA is extended to double strands of DNA. The extension step is normally performed at about 70° C., and a deoxyribonucleotide triphosphate (hereinafter, dNTP) and a DNA polymerase that synthesizes the dNTP to the DNA may be used. Hereinafter, a temperature at which a complementary base can be synthesized on the single strand of DNA so that the single strand of DNA becomes to double strands of DNA (e.g., 70° C.) will be defined as an "extension temperature."

In performing a PCR, a coenzyme may be used for stable activity of the DNA polymerase. For example, if the above-described DNA polymerase is Taq polymerase which is highly heat-resistant, magnesium ions may be added for stable activity of a Taq enzyme. In this case, the magnesium ions may be added in the form of $MgCl_2$ or $MgSO_4$ aqueous solution.

In performing a PCR, a buffer solution may be used to provide an optimal pH and/or salt concentration to a DNA amplification reaction.

During a PCR, the above-described denaturation step, annealing step, and extension step may be performed. These three steps may be performed sequentially and repeatedly. The amount of amplified target genetic material may be increased through repetition of the PCR.

Hereinafter, a patch applied to a PCR will be disclosed on the basis of the general functions of a patch (e.g., delivery of substance, providing of environment). "Required solutions" normally refer to dNTP, DNA polymerase, primer, coenzyme, and buffer solution described herein, although a solution other than dNTP, DNA polymerase, primer, coenzyme, and buffer solution may be further used as necessary,.

The above-described few temperatures are merely general numerical values to assist in understanding the present application, and the scope of the present application should not be limitedly interpreted through the disclosed numerical values. That is, even when temperature of a sample is adjusted differently from some of the above-mentioned numerical values, the temperature should still be interpreted as belonging to the equivalent scope if a result is similar.

5. Preparation of Target Sample

A PCR process using a patch PA may be performed on a sample SA that includes a target genetic material.

For example, the PCR process using the patch PA may be performed on an extracted genetic material. The genetic material may be extracted on a site for gene identification or extracted using tissue or blood of a person who is subject to diagnosis.

For the extraction of genetic material, a process using a PCR pre-treatment apparatus may be performed, or a lysozyme reagent for a cell wall lysis and a sodium dodecyl sulfate (SDS) reagent for detergent may be used.

As another example, the PCR process using the patch PA may be performed directly on blood without a separate pre-treating process.

When a PCR process is performed for diagnosis of viral disease, a target genetic material that is desired to be detected may be the DNA or RNA of viruses. Consequently, the PCR process may be performed on a sample SA that includes genetic material of viruses.

Blood infected with viruses may include the DNA and/or RNA of viruses. For example, a RNA of the virus (that is, viral RNA) may float in blood of a patient infected with Zika virus.

By targeting on a viral genetic material which is present in blood as a target, the PCR process for diagnosis of viral disease may also be performed on a blood sample SA without the pre-treating process.

Figure 36:
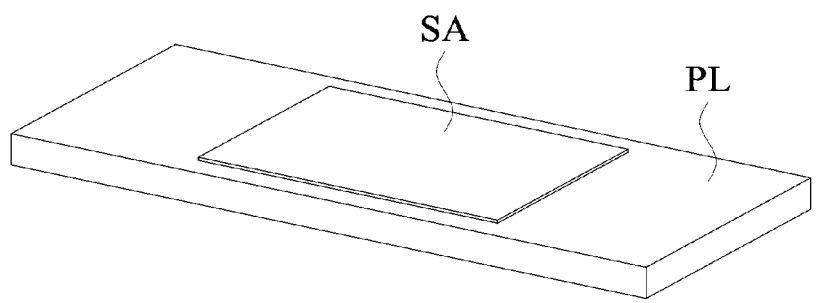
FIG. 36 is a view for describing provision of a target sample according to the present application.

FIG. 36 is a view for describing provision of a target sample SA according to the present application.

While a sample SA may be provided in a PCR tube to allow the sample SA to be mixed with a reagent RA in the form of an aqueous solution in a general PCR process, the sample SA may be provided on a plate PL (e.g., a slide glass) in a PCR process using a patch PA. This may be understood as being due to the function of the patch, which is capable of retaining the reagent RA in the form of an aqueous solution and also transferring the substance to the sample SA located on the plate.

The sample SA may be provided in a single layer on the plate PL. To provide the sample SA in a single layer on the plate PL, a method of smearing the sample SA on the plate PL or printing the sample SA on the plate PL with adjusting a discharge speed and a discharge position of the sample SA may be used.

In a PCR process using blood, when the sample SA (that is, blood) is provided in a single layer, a part of cells included in the sample SA (for example, white blood cells and red blood cells) may be arranged in a two-dimensional array. When the sample SA is provided in a single layer on the plate PL, the number of overlapping cells may be reduced in comparison to when the sample SA is discharged using a dropping pipet or provided in multiple layers. Therefore, when the sample SA is provided in a single layer, an analysis result of the sample SA (e.g., an image of the sample SA) may become more accurate may occur.

The sample SA provided on the plate PL may be fixated. For example, a sample SA smeared on the plate PL may be fixated on the plate PL. For another example, a sample SA printed on the plate PL may be fixated on the plate PL. For yet another example, a sample SA discharged using a dropping pipet may be fixated on the plate.

The sample SA being fixated on the plate PL refers to a state in which a force of resistance is generated to allow the sample SA to stay on the plate PL until a external force of a reference strength is applied to the sample SA. As a result, even when the patch PA and the plate PL are contacted to each other or separated from each other, the sample SA may not be absorbed into the patch PA.

The sample SA may be fixated on the plate PL using any method that is used in the art to which the present application pertains. For example, a method of providing methanol for the sample SA and volatilizing the methanol may be used to fixate the sample SA to the plate PL.

Hereinafter, a patch PA applied to a PCR, a PCR method using the patch PA, and a diagnostic apparatus will be described in more detail. However, in describing the above-described patch PA, method, and apparatus, it will be assumed that the sample SA is provided on the plate PL.

Also, a PCR process using an RNA sample SA that includes RNA and a PCR process using a DNA sample SA that includes DNA are substantially similar to each other. Hereinafter, a PCR process will be described by assuming that a sample SA is DNA, and a PCR process using an RNA sample SA will be described in a description of a tenth embodiment on the basis of differences from the PCR process using the DNA sample SA.

6. Patch Used in PCR Process

A patch PA according to the present application may be used in a PCR process. The patch PA may include at least a part of reagents RA used in the PCR process.

The patch PA may contain the reagents RA. The reagents RA retained in the patch PA may be contained in the patch PA due to the polarity of the patch PA. For example, when the polarity of the net-like structure and the polarity of the reagents RA are same, the reagents RA may be maintained in the patch PA for a predetermined time duration due to an attractive force between the net-like structure and the reagents RA.

The patch PA may contain plural types of reagents RA used in one cycle of a PCR process. For example, the patch PA may contain a dNTP, a DNA polymerase, a primer, a buffer solution, and a coenzyme. When the PCR process is performed using the patch PA containing the dNTP, DNA polymerase, primer, buffer solution, and coenzyme (hereinafter, "all-in-one patch PA"), one cycle of the PCR process (that is, sequential performance of the denaturation step, the annealing step, and the extension step in that order) may be performed even without any medium other than the all-in-one patch PA for providing the reagents RA.

The patch PA may contain at least a part of reagents RA among the plural types of reagents RA used in one cycle of the PCR process.

When the patch PA contains at least a part of reagents RA among the reagents RA used in the PCR process, the remaining reagents RA may be contained in other patch PA. The other patch PA refers to a separate patch PA which is separated from the patch PA, but it does not necessarily mean that reagents RA contained in the patch PA are different from reagents RA contained in the other patch PA.

Alternatively, when the patch PA contains at least a part of reagents RA among the reagents RA used in the PCR process, the remaining reagents RA may be applied on the plate PL on which a sample is provided.

Alternatively, when the patch PA contains at least a part of reagents RA among the reagents RA used in the PCR process, the remaining reagents RA may be kept in a medium configured to be applied to a sample SA during the PCR process. For example, the medium may be a sheet of paper, a thread, or other materials which may keep a reagent RA, and the reagent kept in the medium may be soluble and delivered into a aqueous by contacting.

Alternatively, when the patch PA contains at least a part of reagents RA among the reagents RA used in the PCR process, at least a part of the remaining reagents RA may be contained in other patch, and at least a part of the remaining reagents RA may be applied on the plate PL on which the sample SA is provided.

Regarding the reagents RA used in the PCR process that may be kept using various means, combinations of reagents RA contained together may be classified through some of the above-described methods.

Factors that may be taken into consideration in finding a preferable combination of reagents RA will be listed below. However, the factors listed below are not essential factors to be considered when storing reagents RA in the patch PA.

Hereinafter, for convenience of description, the description will be given by assuming that reagents RA used in a PCR are separately contained in a first patch PA and a second patch PA unless otherwise mentioned. Also, the description will be given by assuming that at least a part of reagents RA contained in the first patch PA are first reagents RA, and at least of a part of reagents RA contained in the second patch PA are second reagents RA.

Reagents may be contained in the first patch PA and the second patch PA by taking into consideration relationships between reagents RA with which non-specific binding may occur among the multiple types of reagents.

For example, to prevent the primer-dimer phenomenon in which a forward primer and a reverse primer bind non-specifically, the forward primer may be contained in the first patch, and the reverse primer may be contained in the second patch.

Reagents RA may be contained in the first patch PA and the second patch PA by taking into consideration reagents RA that create an active environment and reagents RA that receive the active environment among the multiple types of reagents RA.

For example, to prevent the coenzyme from activating the DNA polymerase, the DNA polymerase may be contained in the first patch PA, and the coenzyme may be contained in the second patch PA.

As another example, the buffer solution may be contained in the first patch PA, and the dNTP and the DNA polymerase may be contained in the second patch PA, to prevent the DNA polymerase and the dNTP from receiving an activation conditions for the extension during a PCR process by the buffer solution prior to the extension step. Alternatively, for the same reasons as the above, the dNTP, the primer, and the DNA polymerase may be applied on the plate PL, and the buffer solution and the coenzyme may be contained in the first patch PA.

Reagents RA may be contained in the first patch PA and the second patch PA by taking into consideration time points when the multiple types of reagents RA should be provided to a sample SA.

For example, during a PCR process, to provide at the same time reagents RA that should be provided to a sample SA during the same step, the primer may be contained in the first patch PA, and the DNA polymerase, the dNTP, the buffer solution, and the coenzyme may be contained in the second patch PA.

According to the above-described embodiment, when a primer needs to be changed to diagnose a disease different from that diagnosed by previous PCR testing, by separately constituting the patch PA to contain the primer which should be changed in accordance with a sequence of a target genetic material, it is advantageous that a waste for replacing a patch containing all reagents RA with other patch can be resolved.

Reagents RA may be contained in the first patch PA and the second patch PA by taking into consideration reagents RA that are consumed during a PCR process among the multiple types of reagents RA.

For example, after comparing an appropriate amount of substance that is applicable on the plate PL and an appropriate amount of substance that is storable in the patch PA, reagents RA that are consumed as the PCR process is performed may be contained in a region capable of storing a large amount of substance.

More specifically, when the amount of substance applicable on the plate PL is smaller than the amount of substance storable in the patch PA, the DNA polymerase may be applied on the plate, and the primer and dNTP which are consumed when one cycle is performed may be contained in the patch.

By taking into consideration advantages that may be derived in accordance with some factors described above, the factors may also be taken into consideration in combination.

For example, in consideration of non-specific binding relationships, a forward primer may be contained in the first patch PA, and a reverse primer may be contained in the second patch PA. In consideration of time points when the reagents RA should be provided to a sample SA, the dNTP, the DNA polymerase, the buffer solution, and the coenzyme may be contained in a third patch PA.

The PCR process using the patch PA and the plate PL according to some embodiments described above may be easily understood through embodiments of the PCR process which will be described below.

The patch PA including lysozyme (hereinafter, "lysis patch") may be used in the PCR process. The lysis patch PA does not always have to be applied to a PCR process which will be described below, but may be optionally used as necessary. For example, the lysis patch PA may be used for a purpose of breaking down a membrane structure such as a cell wall included in the sample SA provided on the plate PL, or may also be used at one or more time points during which a pre-processing process of the sample SA is performed.

A patch PA that does not include a reagent RA (hereinafter, "empty patch PA") may be used in the PCR process. Like the lysis patch PA, the empty patch PA does not always have to be applied to the PCR process but may be optionally used. For example, the empty patch PA may be used for a purpose of absorbing and removing a substance provided on the plate PL or may also be used for a purpose of absorbing a sample SA provided on the plate PL in order to provide a space in which the sample SA may react.

7. Providing Reagents

The patch PA according to the present application may provide reagents RA to the plate PL. The patch PA may come into contact with the plate PL and, due to the contact, provide reagents RA contained in the patch PA to the plate PL.

The final destination of the reagents RA provided to the plate PL may be a region on the plate PL in which the sample SA is provided. To provide the reagents RA to the sample SA, the patch PA may come into contact with a region on the plate PL in which the sample SA is provided.

The contact between the plate PL and the patch PA may be released. Due to the release of contact between the plate PL and the patch PA, the reagents RA provided to the plate PL may be absorbed into the patch PA.

Hereinafter, contact between the patch PA and the plate PL and an outline of a mechanism in which the reagents RA are provided due to a release of the contact, and a means in which the reagents RA are provided will be described in more detail.

Figure 37:
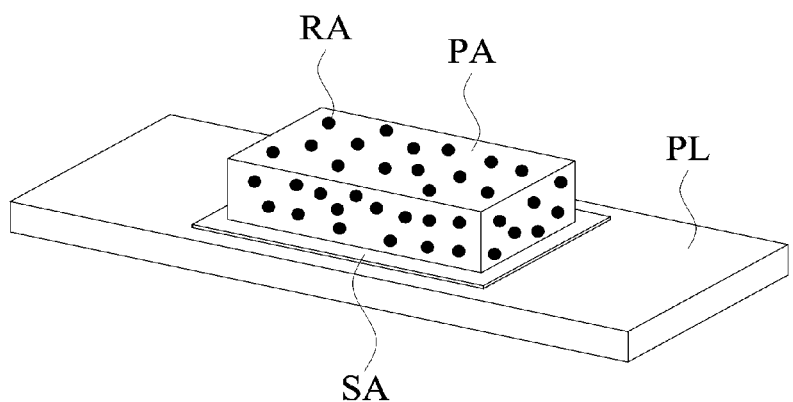
FIG. 37 is a view for describing contact between a patch and a plate according to an embodiment of the present application.

FIG. 37 is a view for describing contact between the patch PA and the plate PL according to an embodiment of the present application.

Contact between the patch PA and the plate PL allows reagents RA (that is, a liquid substance) included in the patch PA to move to the plate PL. Due to the contact between the patch PA and the plate PL, a substance located on the plate PL may also move to the patch PA. Such a function of the patch PA has been described above in detail in the section related to delivery by the patch.

The reagents RA may be provided to the sample SA while the patch PA is in contact with the plate PL.

While the reagents RA are being provided, a part of the reagents RA that have moved from the patch PA to the plate PL may get closer to the sample SA at a distance smaller than or equal to a reference distance, and when some substances on which a force of binding with the reagents RA acts is present in the sample SA, at least a part of the reagents RA may bind to the some of the substances. For example, when the reagents RA that have moved to the plate PL by the patch PA are primers, the primers may bind to a DNA, which is included in the sample SA, in the annealing step.

The reagents RA that have moved to the plate may provide a specific environment to the sample SA. Here, the specific environment may refer to a pH condition, a salt concentration, and/or an ionic concentration. As an example in which a specific environment is provided to the sample SA, a patch PA that includes a buffer solution may provide an environment, which provides a pH optimal for the extension step, to the sample SA.

Figure 38:
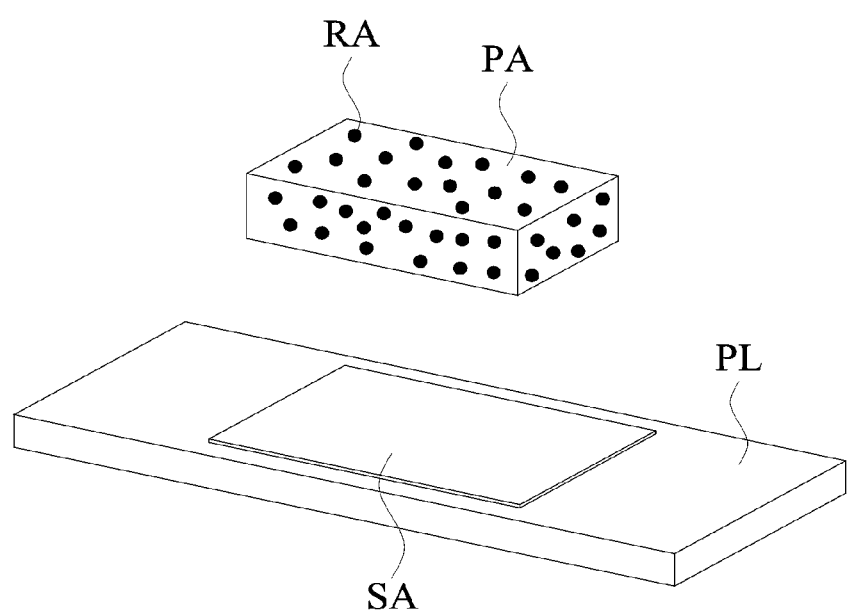
FIG. 38 is a view for describing separation between a patch and a plate according to an embodiment of the present application.

FIG. 38 is a view for describing a release (separation) between the patch PA and the plate PL according to an embodiment of the present application.

When contact between the patch PA and the plate PL is released, the reagents RA that have been provided to the plate PL by the patch PA may be captured in the patch PA again.

A liquid substance that includes the reagents RA that have been provided to the plate PL by the patch PA may be captured in the patch PA again. In comparison to the liquid substance that has been provided to the sample SA by the patch PA, the liquid substance that is captured again may be in a state in which at least a part of the substances are lost.

For example, when primers are included in the patch PA, a liquid substance including the primers may be provided to the sample SA upon contact between the patch PA and the plate PI. When the annealing step is performed, at least a part of the primers contained in the patch PA may bind to DNA included in the sample SA. When the patch PA and the plate PL are separated, the liquid substance, excluding at least a part of the primers bound to the sample SA, may be re-captured into the patch PA. In this case, in comparison to the liquid substance provided to the plate PL, the re-captured liquid substance may be in a state in which at least a part of primers are lost.

When the contact between the patch PA and the plate PL is released, an environment that has been provided to the plate PL by the patch PA may be blocked.

Even after the contact between the patch PA and the plate PL is released, the patch PA may maintain its original function. For example, a substance contained in the patch PA may be diffused in the patch PA.

Figure 39:
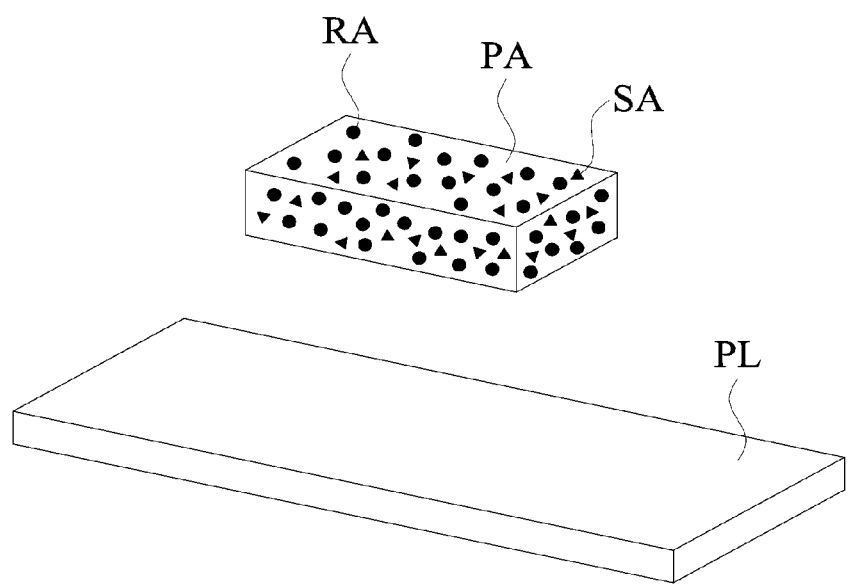
FIG. 39 is a view for describing separation between a patch and a plate when a sample is not fixated on the plate according to an embodiment of the present application.

FIG. 39 is a view for describing separation between the patch PA and the plate PL when a sample SA is not fixated on the plate PL according to an embodiment of the present application.

When the sample SA provided on the plate PL is not fixated, the sample SA may move to the patch PA upon contact between the patch PA and the plate PL. The patch PA may capture the sample SA. The sample SA captured in the patch PA may move in the patch PA. Due to diffusion of the sample SA, a position of the sample SA may be changed.

The reagents RA that have been contained in the patch PA may move to the plate PL due to contact between the patch PA and the plate PL. The reagents RA may be diffused in the patch PA.

The sample SA may be introduced into the patch PA, and a PCR may be performed. The patch PA may capture the sample SA and provide a reaction space. For example, the sample SA may react with the reagents RA that have been contained in the patch PA. As another example, the sample SA may react with a substance that is absorbed together with the sample SA. In this case, the reagents RA that have been contained in the patch PA may also perform a function of providing a specific environment to the sample SA.

When the sample SA provided on the plate PL is not fixated, the sample SA may be separated from the plate PL and captured in the patch PA upon a release of the contact between the patch PA and the plate PL.

Even after the contact between the patch PA and the plate PL is released, the patch PA may maintain its original function. For example, a substance captured in the patch PA may be diffused in the patch PA. Consequently, the sample SA may move in the patch PA, and the reagents RA and the sample SA contained together may react with each other even after the contact between the patch PA and the plate PL is released.

Figure 40:
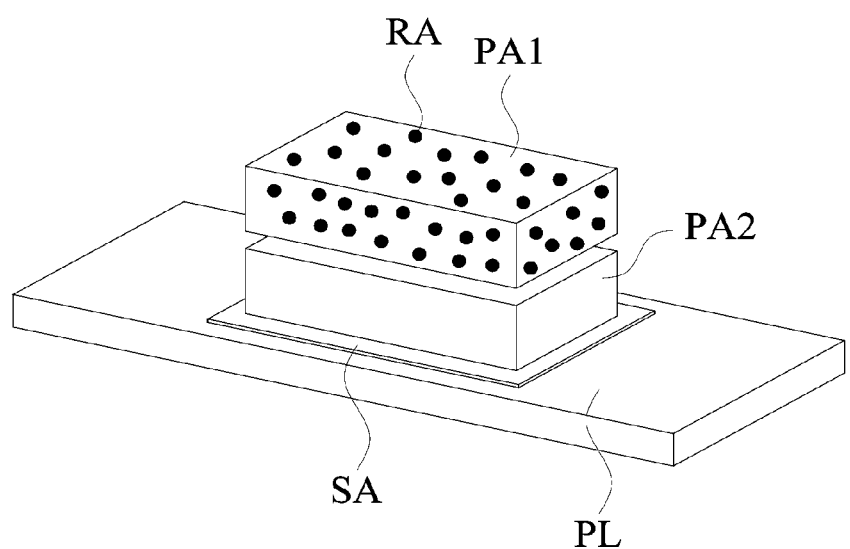
FIG. 40 is a view for describing contact between a patch and a plate through a medium according to an embodiment of the present application.

FIG. 40 is a view for describing contact between a patch PA and a plate PL through a medium according to an embodiment of the present application.

Instead of directly contacting the patch PA and the plate PL may come into contact using a separate medium that performs channeling between the patch PA and the plate PL. Even when the patch PA and the plate PL are connected through a medium, the patch PA may provide reagents RA to the plate PL.

The medium may be a patch PA2. The patch PA2 may be a separate patch PA that is different from a patch PA1 that contains reagents RA. Hereinafter, for convenience of description, the patch PA2 which serves as a medium will be defined as "second patch PA2," and the patch PA1 which contains reagents will be defined as "first patch PA1."

The medium may be a medium that is implemented to interact with the sample SA during a PCR process. The medium may be provided between the plate PL and the patch PA and receive a moist environment (liquid environment) from the patch PA. Reagents RA contained in the medium may move to the plate PL.

"Contacting" of the patch PA and the plate PL includes both direct contact between the patch PA and the plate PL and indirect contact between the patch PA and the plate PL using a medium, unless otherwise mentioned.

When the first patch PA1 contacts with the plate PL through the second patch PA2, reagents RA contained in the first patch PA may move to the plate PL. This is due to a function in which a substance included in the first patch PA1 may move to the second patch PA2 through contact between the first patch PA1 and the second patch PA2, and a substance included in the second patch PA2 may move to the plate PL through contact between the second patch PA2 and the plate PL.

The region where the substance is movable can be expanded due to contact between the first patch PA1and the second patch PA2 and contact between the second patch PA2 and the plate PL, and a function similar to that in the case that the patch PA and the plate PL come into direct contact may be performed.

Figure 41:
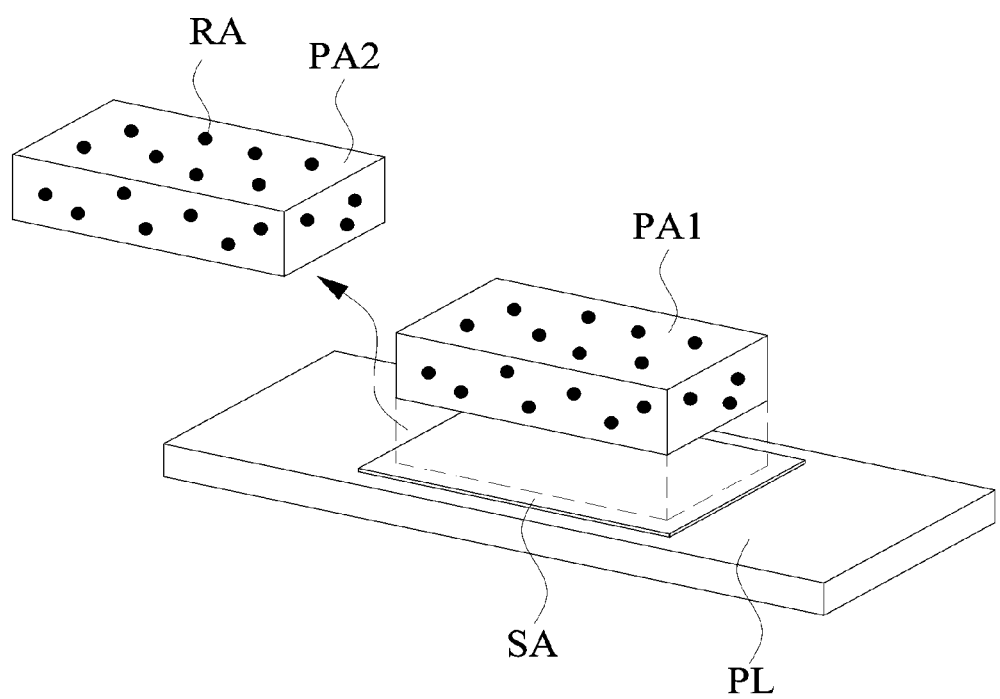
FIG. 41 is a view for describing a release of contact between a patch and a plate through a medium according to an embodiment of the present application.
Figure 42:
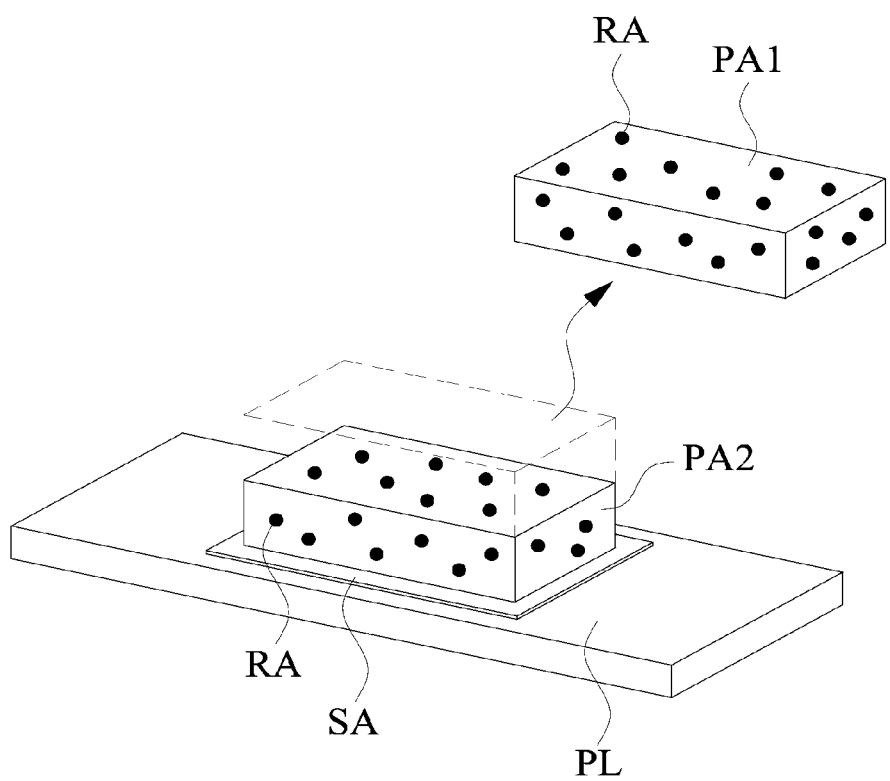
FIG. 42 is a view for describing a release of contact between a patch and a plate through a medium according to an embodiment of the present application.

FIGS. 41 and 42 are views for describing a release of contact between the patch PA and the plate PL through a medium according to an embodiment of the present application.

The above-described contact between the patch PA and the plate PL using a medium may be separated by releasing contact between the medium and the plate PL.

In case that the medium is a patch, when the contact between the first patch PA1 and the plate PL is released via a release of contact between the second patch PA2 and the plate PL, the reagents that have been provided to the sample SA may be absorbed back into the second patch and the first patch.

The reagents RA that have been contained in the first patch PA1 may no longer be movable to the plate PL.

Substantially, when the plate PL and the sample SA contact with each other using a medium or when the contact between the plate PL and the sample SA are released by removing the medium, a function similar to the case of that the sample SA and the plate PL are directly contacted or are separated from each other may be performed.

The "release" of contact between the patch PA and the plate PL includes both a release of a direct contact between the patch PA and the plate PL and a release of an indirect contact between the patch PA and the plate PL using a medium, unless otherwise mentioned. Also, "separation (disconnection) of contact" may be used interchangeably with the above-described "release of contact."

The contact between the patch PA and the plate PL using a medium may be disconnected by releasing contact between the medium and the patch PA. In this case, the medium may remain in contact with the plate PL.

In case that the medium is a patch, when the contact between the first patch PA1 and the plate PL is released via a release of contact between the first patch PA1 and the second patch PA2, the reagents RA contained in the first patch PA1 are no longer movable to the second patch PA2 or the plate PL. However, the second patch PA2 and the plate PL remain in contact, and the reagents RA contained in the second patch PA2 may move to the plate PL.

When the first patch PA1 and the second patch PA2 are separated, a liquid substance in a predetermined range remains in the second patch PA2. Also, a part of the reagents RA that have been moved through contact between the first patch PA1 and the second patch PA2 may be remained in the second patch PA2.

As a result, even when the first patch PA1 and the plate PL are separated, a part of the reagents RA contained in the first patch PA1 may be provided to the sample SA. This may exhibit an effect different from that of the case that the patch PA comes into direct contact with the plate PL and the case that the plate PL and the patch PA come into contact using a medium and are separated by removing the medium. For example, the patch PA used for contact between the patch PA and the plate PL may have an advantage in that the reagents RA may be continuously provided to the sample SA even after the patch PA, which is configured to provide the reagents RA, is separated from the patch PA used for the contact.

Even when the plate PL and the patch PA are contacted using a medium, an unfixated sample SA may be introduced into the patch PA. Such a process may be easily understood by those of ordinary skill in the art. However, since there is a disadvantage in that a portion of the sample SA may be separated together with the patch PA and a tiny amount of sample SA may be lost when the medium and the patch PA are separated, detailed description of the process will be omitted.

Various embodiments related to contact between the plate PL and the patch PA for providing reagents RA to the sample SA have been described above. Hereinafter, time points and a number of contacts between the patch PA and the plate PL will be described in more detail.

However, unless otherwise mentioned, "contact between the plate PL and the patch PA" will be assumed as including all of the above-described various embodiments.

Figure 43:
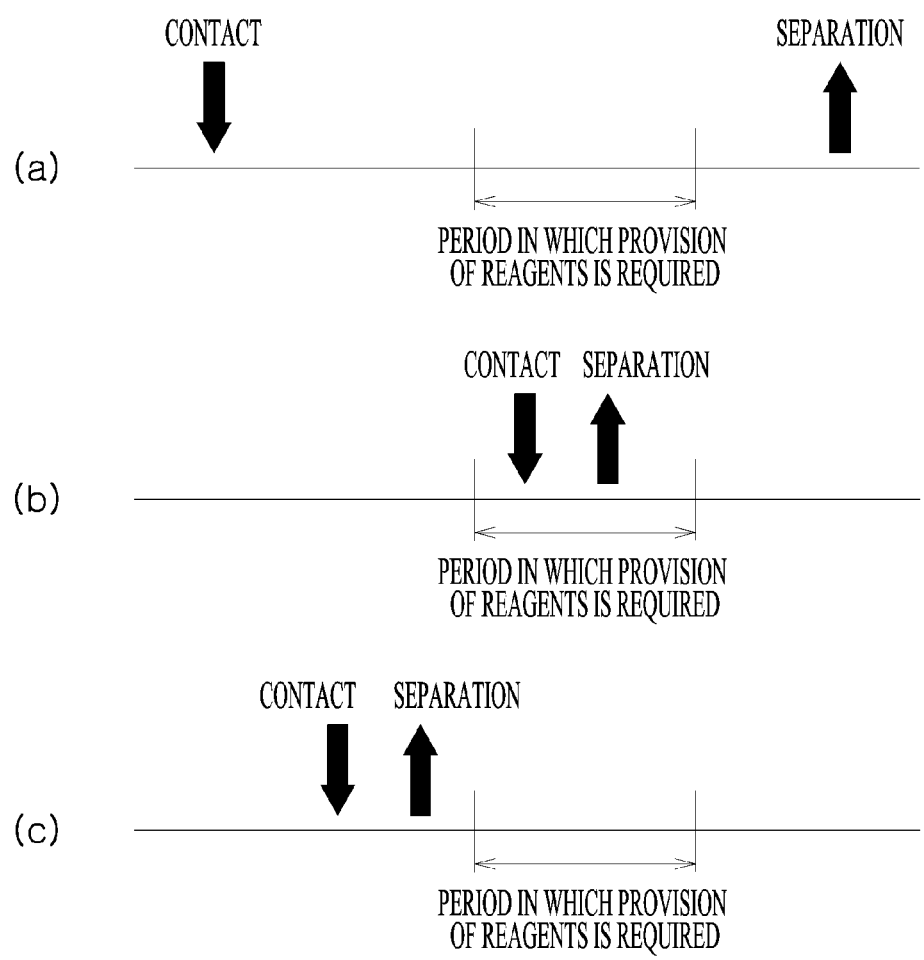
FIG. 43 is a view for describing an interval of contact between a patch and a plate according to an embodiment of the present application.

FIG. 43 is a view for describing a period of contact between a patch PA and a plate PL according to an embodiment of the present application.

Referring to FIG. 43A, the patch PA may be contacted with the plate PL in an period in which providing the reagents RA is required. Generally, the patch PA may provide the reagents RA to the plate PL by contact between the patch PA and the plate PL.

The patch PA may contact with the plate PL before the period in which the providing the reagents RA is required, and the contact between the patch PA and the plate PL may be released after the period in which the providing the reagents RA is required.

Referring to FIG. 43B, the patch PA may contact with the plate PL in a portion of the period in which the providing the reagents RA is required. On the basis of the fact that the reagents RA are provided while the patch PA and the plate PL are in contact, a time of contact between the plate PL and the patch PA may be adjusted in order to adjust an amount of reagents RA provided to the patch PA.

The patch PA may come into contact with the plate PL at any point in time within the period in which the providing the reagents RA is required, and the contact between the patch PA and the plate PL may be released at any point in time within the period in which the providing the reagents RA is required.

Referring to FIG. 43C, the patch PA may not be in contact with the plate PL in at least a part of the period in which the providing the reagents RA is required.

The patch PA may come into contact with the plate PL and then be separated therefrom before the period in which the reagents RA are required.

When the providing the reagents RA can be maintained even after the contact between the patch PA and the plate PL is released, the patch PA and the plate PL can be separated in the period in which the providing the reagents RA is required.

For example, when the patch PA and the plate PL come into contact using a medium (that is, the patch PA) and the contact between the patch PA and the plate PL is disconnected through the release of the contact between the medium and the patch PA, the providing the reagents RA may be maintained. As another example, when the patch PA and the plate PL are in contact and then the sample SA is introduced into the patch PA, the provision of the reagents RA may be maintained even when the patch PA and the plate PL are separated.

Even when the patch PA comes into contact with the plate PL before the period in which the reagents RA are required and then is separated from the plate PL at any time point within the period in which the reagents RA are required, the reagents may be provided to the sample SA in the period in which the reagents RA are required.

Figure 44:
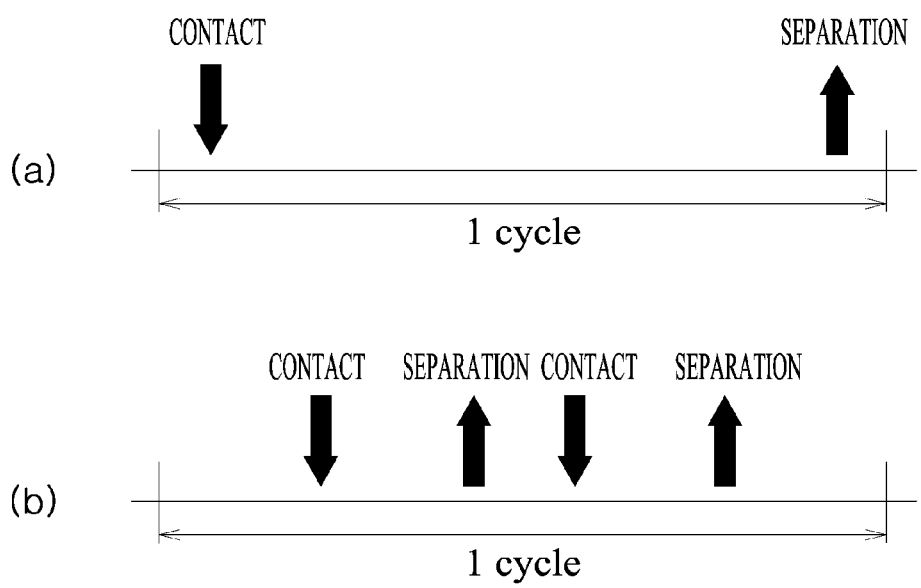
FIG. 44 is a view for describing a number of contacts between a patch and a plate according to an embodiment of the present application.

FIG. 44 is a view for describing a number of contacts between the patch PA and the plate PL according to an embodiment of the present application.

Referring to FIG. 44A, in a process using the patch PA, the patch PA and the plate PL may contact one time for providing the reagents RA. This may mean that, when a DNA amplification process is performed using the patch PA, the patch PA and the plate PL may contact one time while the denaturation step, the annealing step, and the extension step are performed.

Contacting one time for providing the reagents RA has an advantage in that, by omitting unnecessary contact and separation, a procedure of the process is simplified. For example, the PCR process using the all-in-one patch PA may be performed by contacting the all-in-one patch PA with the plate PL, adjusting a temperature to amplify DNA, and separating the all-in-one patch PA and the plate PL after the DNA amplification is completed.

Referring to FIG. 44B, in the process using the patch PA, the patch PA and the plate PL may contact several times for providing the reagents RA. For example, when the patch PA includes the primer used in the annealing step and the DNA polymerase used in the extension step, the patch PA and the plate PL may come into contact at least one time in the annealing step and at least one time in the extension step. As another example, the patch PA may contact with the plate PL several times in the annealing step. As yet another example, the patch PA may contact with the plate PL several times in the extension step. Contacting several times for providing the reagents RA may bring about an effect of preventing denaturation (degeneration) of the patch PA.

For example, the separation of the patch PA from the plate PL at a point in time at which the reagents RA are not required to be provided may prevent the reagents RA contained in the patch PA from being affected by the plate PL. In this way, the patch PA may be prevented from being heated, cooled, or made to contain a different substance from the plate PL. This effect will be disclosed in more detail in description of a sixth embodiment which will be given below.

Figure 45:
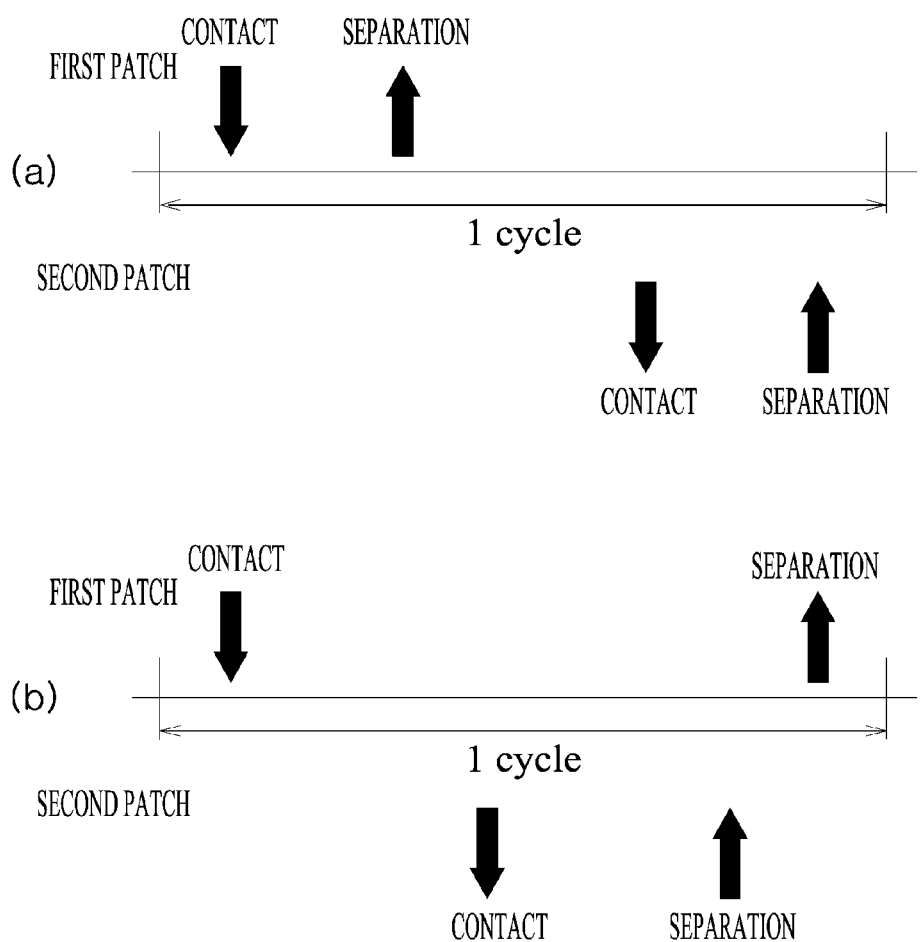
FIG. 45 is a view for describing contact between a plurality of patches and a plate according to an embodiment of the present application.

FIG. 45 is a view for describing contact between a plurality of patches PA and a plate PL according to an embodiment of the present application.

Referring to FIG. 45A, in performing a process using a patch PA, when a plurality of patches PA are used to provide reagents RA to the plate PL, one patch PA may contact with the plate PL to provide reagents RA, and after the one patch PA is separated from the plate PL, other patch PA may come into contact with the plate PL.

When reagents RA are provided by the other patch PA after the one patch PA and the plate PL are separated, the sample SA provided on the plate PL may receive the reagents RA contained in the other patch PA.

In case that the providing the reagents RA is terminated via a release of the contact between the patch PA and the plate PL (for example, when the patch PA and the plate PL on which the sample SA is fixated come into contact and are separated without a medium therebetween), the reagents RA contained in the one patch PA are not movable to the other patch PA. That is, the reagents RA that the sample SA receives may be limited to the reagents RA contained in the other patch PA that is in contact with the plate PL. In this way, it may be prevented that at least a part of substances of the reagents RA included in the separated one patch PA bind to at least a part of substances of the reagents RA included in the other patch PA being contacted with the plate PL afterwards.

In case that the providing the reagents RA is not terminated even upon a release of the contact between the patch PA and the plate PL (for example, when the patch PA comes into contact with and is separated from a medium located on the plate PL), the other patch PA may also receive at least a part of the reagents RA that have been contained in the separated one patch PA. In this way, a function similar to that of the case that a plurality of patches PA are simultaneously provided on the plate PL within a predetermined interval, which will be described below, may be performed.

Referring to FIG. 45B, in performing a PCR process using a patch PA, when a plurality of patches PA are used to provide reagents RA to the plate PL, while one patch PA is in contact with the plate PL and provides reagents RA (that is, before the one patch PA and the plate PL are separated), other patch PA may contact with the plate PL.

The plate PL may simultaneously be in contact with the plurality of patches PA for a predetermined time duration.

The simultaneous contact of the plurality of patches PA may be performed by direct contact between the plate PL and the first patch PA and direct contact between the plate PL and the second patch PA. Here, "direct contact" may refer to contact between the patch PA and the plate PL without any medium therebetween.

Alternatively, the simultaneous contact of the plurality of patches PA may be performed by direct contact between the first patch PA and the plate PL and indirect contact between the second patch PA and the plate PL. Here, "indirect contact" may refer to contact between the patch PA and the plate PL through a medium and may refer to contact between the second patch PA and the first patch PA that allows the reagents RA contained in the second patch PA to be provided to the plate PL.

In case that the reagents RA contained in the other patch PA are provided to the sample SA, it may be required that the reagents RA contained in the other patch PA should be provided together with the reagents RA contained in the patch PA that has come into contact with the plate PL first. In this case, the process method may be used more efficiently.

For example, the first patch PA may include a primer and a coenzyme, and the second patch PA may include a dNTP, a DNA polymerase, and a buffer solution. When the first patch PA and the second patch PA are used in a PCR process, the reagents RA included in the first patch PA and the reagents RA included in the second patch PA are required to be provided together in the extension step, and the above-described method may be applied in this case.

Even in the process in which the reagents RA are provided by the plurality of patches PA, at least a part of the plurality of patches PA may come into contact with the plate PL several times. Since this may be performed similarly to the single patch PA coming into contact with the plate PL several times, detailed description thereof will be omitted.

Hereinafter, unless otherwise mentioned, the description will be given by assuming that the patch and the plate come into direct contact and the sample is fixated on the plate. However, the description below may also be easily applied to the case that the patch and the plate come into indirect contact and/or the case that the sample is not fixated on the plate.

8. Temperature Adjustment

The patch PA according to the present application may be used in a PCR process. Each step of the PCR process requires that a temperature of the sample SA be maintained at a suitable temperature. The temperature of the sample SA may be maintained at the denaturation temperature, the annealing temperature, or the extension temperature.

To adjust the temperature of the sample SA to an optimal temperature condition, the plate PL may be heated, cooled, or maintained a target temperature. Alternatively, to adjust the temperature of the sample SA to an optimal temperature condition, the patch PA may be heated, cooled, or maintained a target temperature. Alternatively, to adjust the temperature of the sample SA to an optimal temperature condition, both the plate PL and the patch PA may be heated, cooled, or maintained a target temperature.

When the patch PA and the plate PL are in contact, the temperature of the sample SA may be adjusted by adjusting a temperature of the plate PL. Also, even when the patch PA and the plate PL are separated, the temperature of the sample SA may be adjusted by adjusting the temperature of the plate PL.

However, in case that the temperature of the sample SA is adjusted by adjusting the temperature of the patch PA, although the temperature of the sample SA can be adjusted by adjusting the temperature of the patch PA when the patch PA and the plate PL are in contact, the temperature of the sample SA cannot be adjusted by adjusting the temperature of the patch PA when the patch PA and the plate PL are separated. Because the thermal equilibrium is generally caused via heat transfer by contact between two objects, when the patch PA and the plate PL are separated, the temperature of the sample SA may not be adjusted by adjusting the temperature of the patch PA.

The temperature of the sample SA may be adjusted by controlling temperatures of the patch PA and the plate PL. When the temperatures of the patch PA and the plate PL are controlled, a faster temperature adjustment may be possible in comparison to when the temperature of the sample SA is adjusted by controlling temperature of any one entity.

Figure 46:
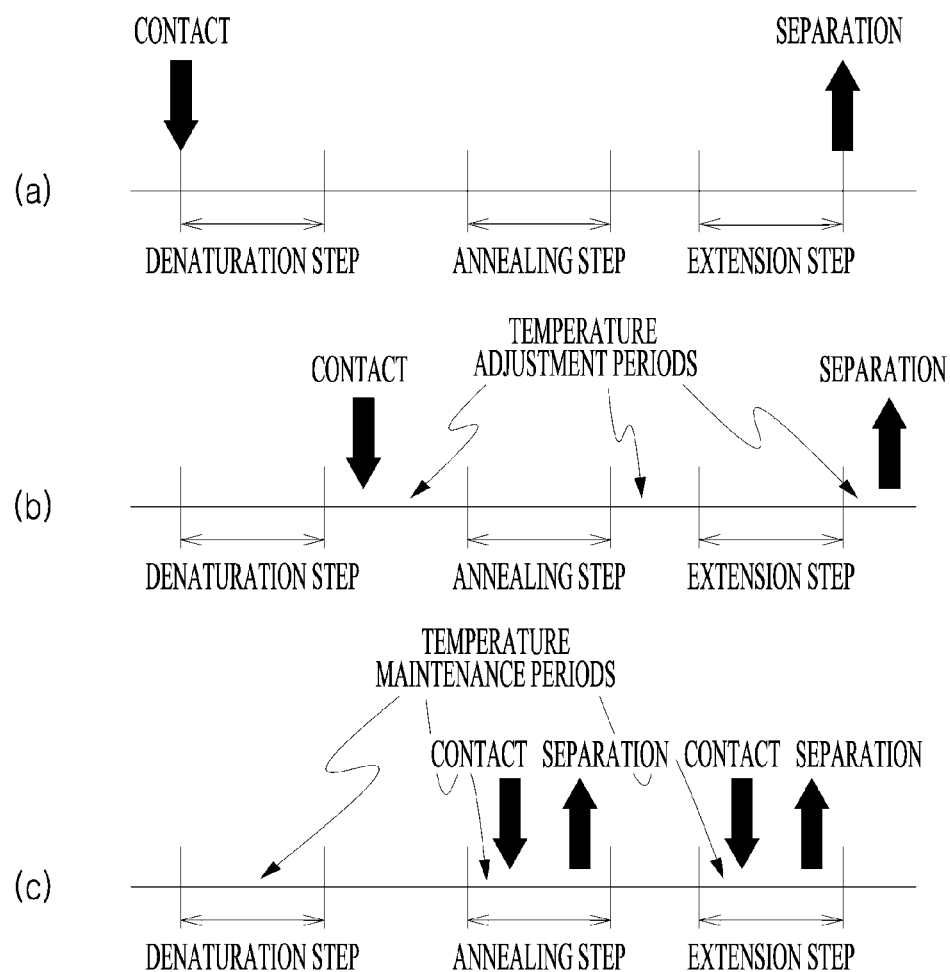
FIG. 46 is a view for describing a point in time of contact between a patch and a plate in relation to different steps according to an embodiment of the present application.

FIG. 46 is a view for describing a point in time of contact between a patch PA and a plate PL in relation to different steps according to an embodiment of the present application.

Referring to FIG. 46A, the patch PA may contact with the plate PL before a DNA amplification process begins and may remain in contact with the plate PL until the DNA amplification process ends. This has an advantage in that a PCR process may be performed through the simplest procedure of the process.

However, considering that the temperature in the denaturation step is about 95° C., whether the patch PA is degenerated may become a problem. More specifically, when the patch PA is implemented with a material that may be deformed by heat, to prevent degeneration of the patch PA, it may be preferable that the patch PA be separated from the sample SA in the denaturation step. In consideration of this aspect, a time point of a contact between the patch PA and the sample SA and/or a time point of a release of the contact may be set.

This will be described in more detail in the description of the sixth embodiment which will be given below.

Referring to FIG. 46B, the patch PA may contact with the sample SA in temperature adjustment periods.

Hereinafter, the temperature adjustment periods will be defined as a period in which the temperature of the sample SA is changed due to heating before the denaturation step, a period in which the temperature of the sample SA is changed due to cooling before the annealing step, and a period in which the temperature of the sample SA is changed due to heating before the extension step.

When the patch PA comes into contact with the plate PL in the temperature adjustment periods of the sample SA, the temperatures of the sample SA and the patch PA may become similar due to the thermal equilibrium, and this prevents a sharp change of the temperature of the sample SA in temperature maintenance periods caused by a temperature difference between the patch PA and the sample SA. Accordingly, when the patch PA comes into contact with the sample SA in the temperature adjustment periods, a more stable PCR process may be performed.

The patch PA may be separated from the sample SA in the temperature adjustment periods. In the temperature adjustment periods, the temperature of the sample SA may be increased or decreased. To prevent denaturation of the reagents RA due to a rapid temperature change of the sample SA, the sample SA and the patch PA may be separated in the temperature adjustment intervals.

Referring to FIG. 46C, the patch PA may come into contact with the sample SA in temperature maintenance periods.

Hereinafter, the temperature maintenance periods will be defined as a period in which the temperature of the sample SA is maintained at the denaturation temperature, a period in which the temperature of the sample SA is maintained at the annealing temperature, and a period in which the temperature of the sample SA is maintained at the extension temperature.

When the patch PA comes into contact with the plate PL in the temperature maintenance periods of the sample SA, since temperatures of the sample SA and the patch PA are different, the temperature of the sample SA that has been adjusted to an optimal temperature may be changed. This may be improved by a method of increasing or decreasing the temperature of the patch PA before the patch PA and the plate PL come into contact. This will be described in more detail below in description of an eighth embodiment.

The patch PA may be separated from the sample SA in the temperature maintenance periods. Taking into consideration that the reagents RA contained in the patch PA are provided to the sample SA due to contact between the patch PA and the plate PL, the contact between the patch PA and the plate PL may be released to block the providing reagents RA to the sample SA. Such a function may be applied to adjust a length of DNA being amplified in the extension step.

The above-described contact and separation between the patch PA and the plate PL may be independent from each other. The patch PA may come into contact with the plate PL in the temperature adjustment periods and be separated from the plate PL in the temperature adjustment periods. As another example, the patch PA may come into contact with the plate PL in the temperature maintenance periods and be separated from the plate PL in the temperature maintenance periods. As yet another example, the patch PA may come into contact with a patch PA in the temperature adjustment periods and be separated from the patch PA in the temperature maintenance periods. As still another example, the patch PA may come into contact with a patch PA in the temperature maintenance periods and be separated from the patch PA in the temperature adjustment periods.

To help in understanding the present application, some embodiments about a PCR process which are related to the temperature of the sample SA and contact between the patch PA and the plate PL will be disclosed. However, the scope of the present application is not limited to the embodiments disclosed below.

Prior to description, the patch PA will be assumed as being the all-in-one patch (that is, a patch including a dNTP, a DNA polymerase, a primer, a buffer solution, and a coenzyme).

For example, the patch PA may be in contact with the plate PL during a DNA amplification process. The patch PA and the plate PL may be in contact in a period in which the temperature of the sample SA is adjusted to the denaturation temperature or a period in which the temperature of the sample SA is maintained at the denaturation temperature. Via the contact, the reagents RA contained in the patch PA may be provided to the plate PL. The temperature of the sample SA may be sequentially adjusted to each of the denaturation temperature, the annealing temperature, and the extension temperature. The temperature adjustment may be performed by adjusting the temperature of the patch PA and/or adjusting the temperature of the plate PL. The patch PA may be separated from the plate PL in a period in which the temperature of the sample SA is maintained at the extension temperature or a period in which the temperature of the sample SA is adjusted to a denaturation step of a different cycle.

As another example, the patch PA may come into contact with the plate PL during the annealing step and the extension step. The patch PA may come into contact with the plate PL in a period in which the temperature of the sample SA is adjusted to the annealing temperature. The reagents RA contained in the patch PA may be provided to the plate PL via the contact. The temperature of the sample SA may be maintained at the annealing temperature, adjusted to the extension temperature, and maintained thereat. The patch PA may be separated from the plate PL in a period in which the temperature of the sample SA is re-adjusted to the denaturation temperature from the extension temperature.

As yet another example, the patch PA may come into contact with the plate PL in the annealing step and the extension step. The patch PA may come into contact with the plate PL several times in one cycle of PCR process. The patch PA may come into contact with the plate PL in a period in which the temperature of the sample SA is maintained at the annealing temperature. The reagents RA contained in the patch PA may be provided to the plate PL due to the contact. The patch PA may be in contact with the plate PL and then separated therefrom during any time point within the period in which the temperature of the sample SA is maintained at the annealing temperature. The reagents RA that have been provided to the plate PL may be blocked via the separation. The temperature of the sample SA may be adjusted to the extension temperature and maintained thereat. The patch PA may be in contact with the plate PL and then separated therefrom in a period in which the extension temperature is maintained. This contact may also allow the reagents RA contained in the patch PA to be provided to the plate PL.

The above-described process may be similarly applied even to a PCR process using a plurality of patches PA.

Taking into consideration that the PCR process using a plurality of patches PA is a PCR process in which a plurality of single patches PA are used, one or more of the plurality of patches PA may come into contact with the plate PL in the temperature adjustment periods or come into contact with the plate PL in the temperature maintenance periods. Also, contact between the one or more of the plurality of patches PA and the plate PL may be separated in the temperature adjustment periods or separated in the temperature maintenance periods.

One or more of the plurality of patches PA are independent from each other. In other words, contact and separation of the first patch does not affect whether the second patch is in contact or separated.

The plurality of patches PA may also simultaneously come into contact with the plate PL during a predetermined period.

Hereinafter, contact between the plurality of patches PA and the plate PL in one cycle of process will be described on the basis of differences thereof from contact between a single patch PA and the plate PL.

To assist in understanding the present application, some embodiments about a PCR process which are related to the temperature of the sample SA and contact between the plurality of patches PA and the plate PL will be disclosed. However, the scope of the present application is not limited to the embodiments disclosed below.

Prior to description, the plurality of patches will be assumed as including the first patch PA and the second patch PA. Also, it will be assumed that the first patch PA includes a primer, and the second patch PA includes a dNTP, a DNA polymerase, a buffer solution, and a coenzyme).

Figure 47:
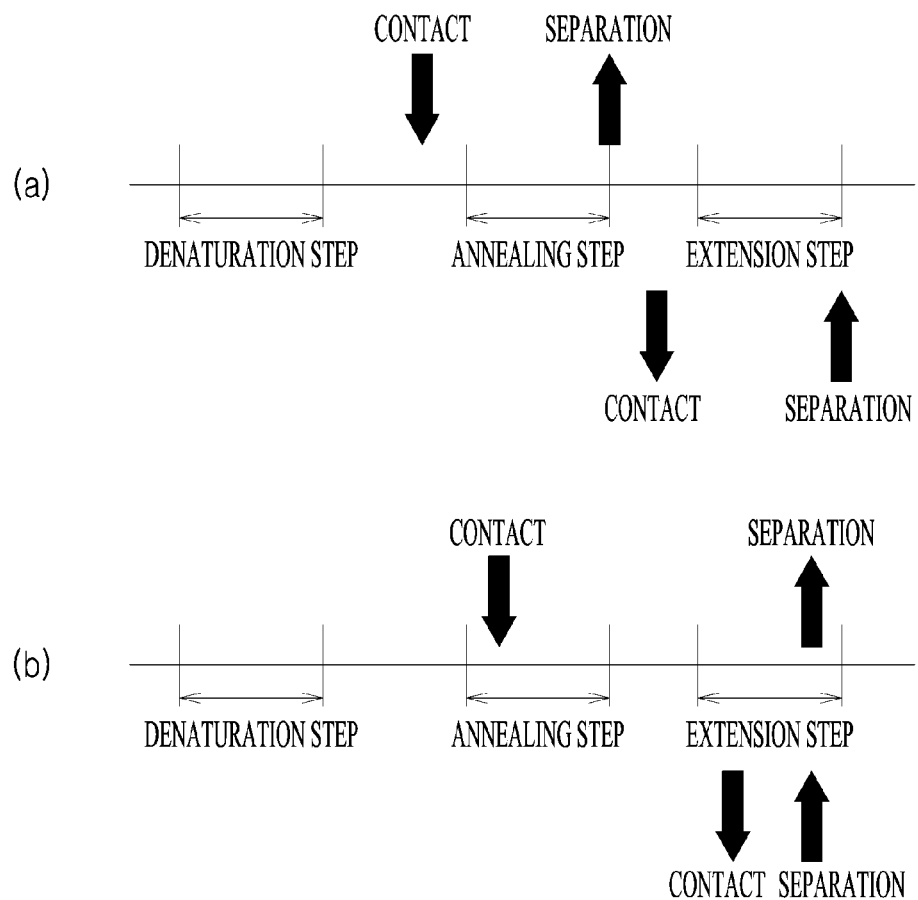
FIG. 47 is a view for describing a point in time of contact between a patch and a plate in relation to different steps according to an embodiment of the present application.

FIG. 47 is a view for describing a point in time of contact between a patch PA and a plate PL in relation to different steps according to an embodiment of the present application.

Referring to FIG. 47A, the first patch PA may contact with the plate PL in a period in which the temperature of the sample SA is adjusted to the annealing temperature. The sample SA may receive the reagents RA contained in the first patch PA via the contact. The temperature of the sample SA may be maintained at the annealing temperature for a predetermined duration. The first patch PA may be separated from the plate PL and the second patch PA may come into contact with the plate PL in a period in which the annealing temperature is adjusted to the extension temperature. The plate PL may receive the reagents RA contained in the second patch PA via the contact. The temperature of the sample SA may be maintained at the extension temperature for a predetermined duration. After the predetermined duration has elapsed, the second patch PA may be separated from the plate PL.

Referring to FIG. 47B, the first patch PA may contact with the plate PL in a period in which the temperature of the sample SA is maintained at the annealing temperature. The sample SA may receive the reagents RA contained in the first patch PA via the contact. The temperature of the sample SA may be maintained at the annealing temperature for a predetermined duration and then be adjusted to the extension temperature. While the temperature of the sample SA is maintained at the extension temperature, the second patch PA may come into contact with the plate PL. In this case, the first patch PA may already have been in contact with the plate PL. The sample SA may receive the reagents RA contained in the second patch PA. The reagents RA contained in the first patch PA may also be provided to the sample SA. The first patch PA and the second patch PA may be separated from the plate PL at any time point. For example, any time point may be within a period in which the temperature of the sample SA is maintained at the extension temperature and may be within a period in which the extension temperature is adjusted to a denaturation temperature of a subsequent cycle.

The method of contact, time points of contacts and number of contacts which have been described in detail above in the "providing reagents" section may be applied to the "contact between the patch PA and the plate PL" disclosed in the "temperature adjustment" section. For example, the patch PA and the plate PL may come into contact several times in one cycle of PCR process in the above-described few embodiments.

9. Sample Analysis

To analyze a sample SA on which a PCR process is performed, an image of the sample SA may be acquired. The DNA may have been amplified in the sample SA.

The image may be obtained by imaging a light that is irradiated from a light source and transmitted through the sample SA. That is, transmitted light may be obtained from a sample SA amplified through the PCR process using the patch PA according to the present application.

By the above-described process, a general image of the sample SA may be acquired. For example, a visible light image of the sample SA that has gone through the PCR process may be acquired.

A fluorescence image of DNA included in the sample SA may be acquired. The fluorescence image may be acquired by varying a wavelength band of light irradiated from the light source. The fluorescence image may be acquired by selectively detecting light that has emitted from the sample SA.

A primer to which a fluorescent substance is bound may be used for detecting the DNA through the fluorescence image. The primer may bind to the DNA through the PCR process, and the amplified DNA may exhibit fluorescence due to the fluorescent substance bound to the primer.

The fluorescent substance may be provided with binding to a blocking substance that blocks fluorescence development as necessary. The fluorescent substance may be designed to bind to the substance for blocking fluorescent development and emit light when the sample SA and the primer are bound to each other.

In addition to the method of acquiring a fluorescence image of the amplified DNA, a method of measuring an amount of emitted fluorescent light may be used. More specifically, an increase in the amount of emitted fluorescent light may be analyzed to perform a quantitative analysis of DNA.

Figure 48:
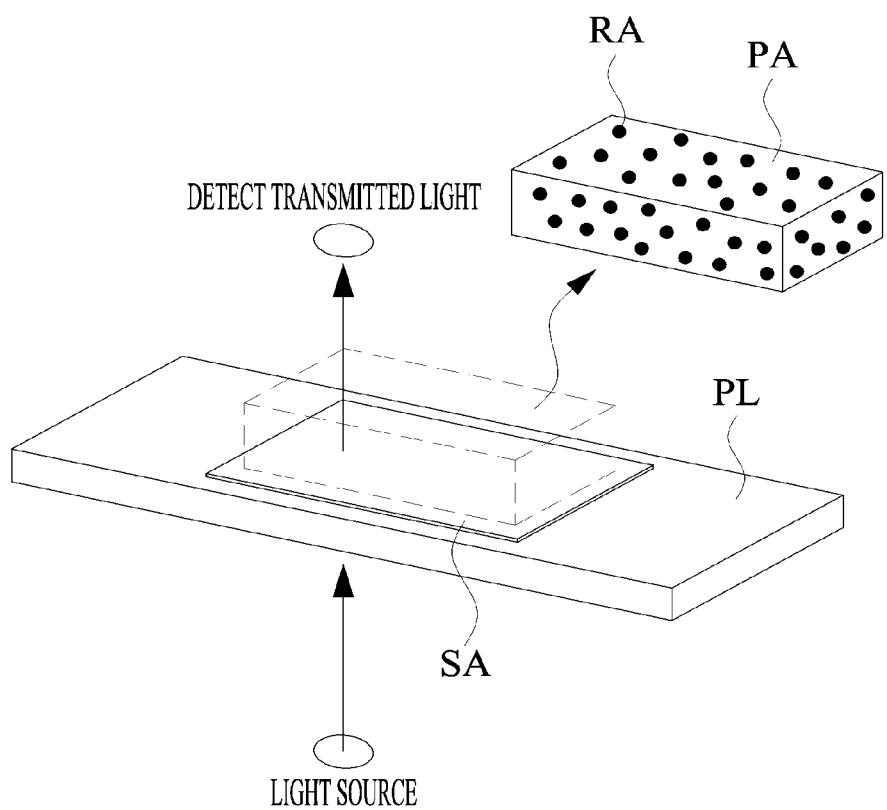
FIG. 48 is a view for describing a method of acquiring an image of a sample according to an embodiment of the present application.
Figure 49:
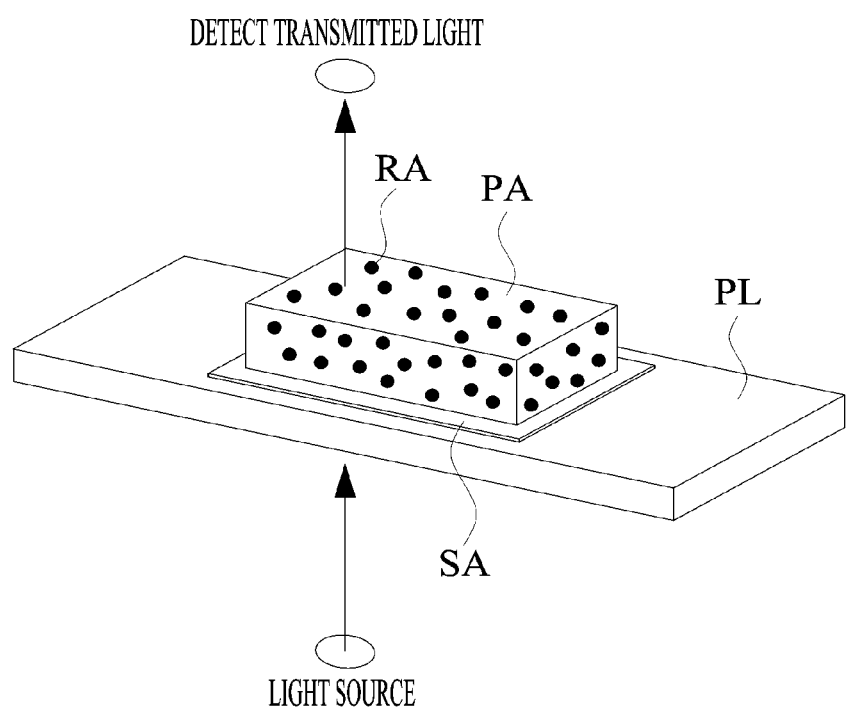
FIG. 49 is a view for describing a method of acquiring an image of a sample according to an embodiment of the present application.

FIGS. 48 and 49 are views for describing a method of acquiring an image of a sample SA according to an embodiment of the present application.

Referring to FIG. 48, an image of a sample SA may be acquired in a state in which the plate PL and the patch PA are not in contact.

To acquire an image of the sample SA, an image of at least a partial region of the plate PL may be acquired. Transmitted light may be acquired through a beam of light that has transmitted through the plate PL.

The sample SA and the plate PL may be separated before obtaining an image of the sample SA. When contact between the sample SA and the plate PL is released, the sample SA that has been provided on the plate PL and the remaining reagents RA excluding some bound to the sample SA may be absorbed into the patch PA. The sample SA provided on the plate PL may be fixated.

When the patch PA and the plate PL are separated, the patch PA may be removed from a light path for the image acquisition. Accordingly, a problem in that light may be scattered while transmitting through the patch PA may be solved. As a result, a clearer image of the sample SA may be acquired.

Referring to FIG. 49, an image of the sample SA may be acquired in a state in which the plate PL and the patch PA are in contact.

To acquire an image of the sample SA, an image of at least a partial region of the plate PL may be acquired. Transmitted light may be acquired via a light that has transmitted through the plate PL. The light that has transmitted through the plate PL may transmit through the patch PA which is in contact with the plate PL.

The acquisition of the image while the patch PA and the plate PL are in contact may also be performed when the sample SA is fixated on the plate PL or also when the sample SA is not fixated on the plate PL such that the sample SA is absorbed into the patch PA.

When the patch PA and the plate PL come into contact, the reagents RA contained in the patch PA may move to the sample SA. Accordingly, an image of the sample SA may be obtained even during a reaction of the sample SA.

The acquisition of the image of the sample SA while the sample SA and the plate PL are in contact may be more suitably applied when performing real-time analysis of the sample SA.

To acquire an image of the sample SA, an image of at least a partial region of the patch PA may be acquired as necessary. That is, by designing a light that has not transmitted through the plate PL to transmit through the patch PA, the transmitted light may be acquired via the light that has transmitted through the patch PA.

Figure 50:
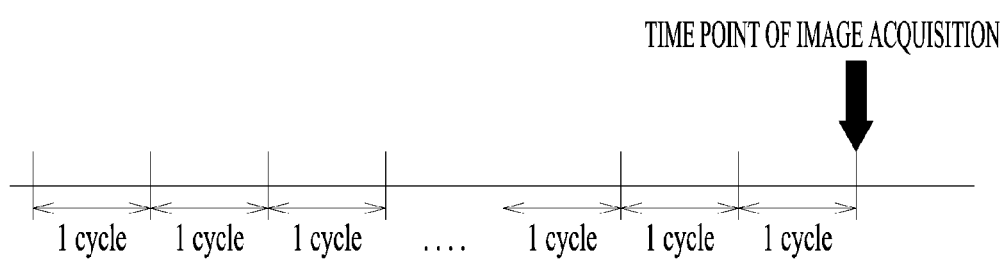
FIG. 50 is a view for describing a point in time of acquisition of an image of a sample according to an embodiment of the present application.
Figure 51:
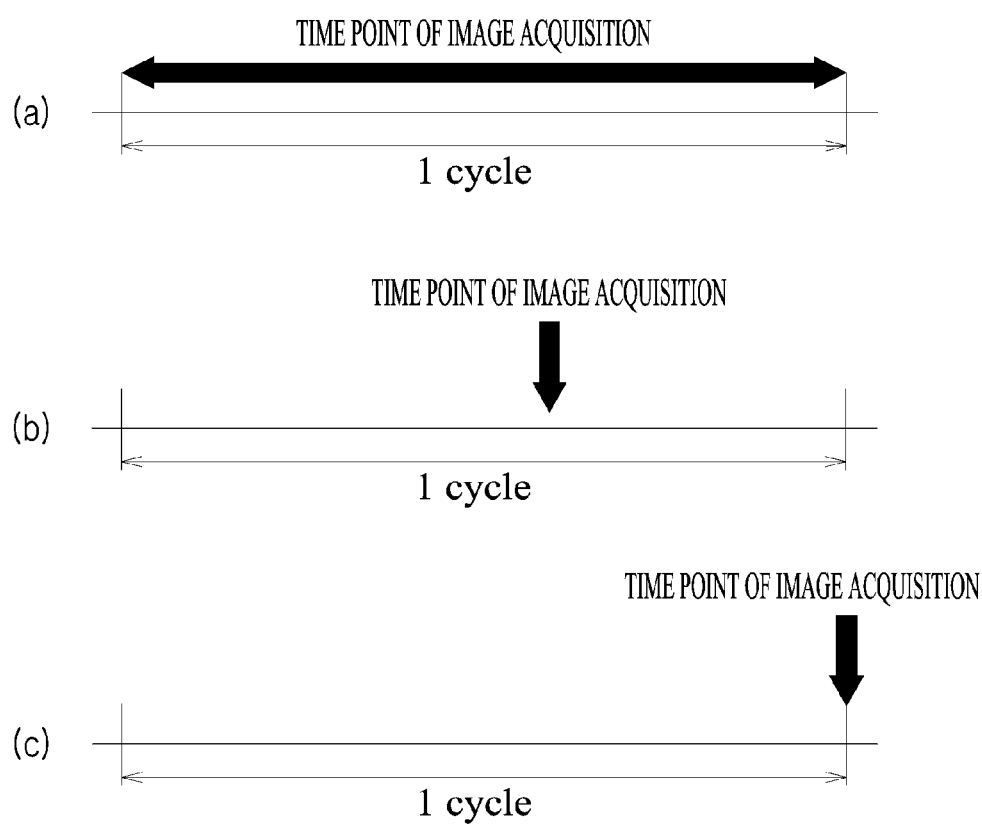
FIG. 51 is a view for describing a point in time of acquisition of an image of a sample according to an embodiment of the present application.

FIGS. 50 and 51 are views for describing a point in time of acquisition of an image of a sample SA according to an embodiment of the present application.

Referring to FIG. 50, an image of a sample SA on which one cycle of PCR process has been performed several times may be acquired. For example, an image of a sample SA on which a desired PCR process has been completed may be acquired.

The image may be acquired at any time point during the PCR process. Instead of an image for measuring a change in the sample SA with time, a one-time image may be acquired for analyzing an amplified target DNA of the sample SA detected at any time point.

The acquisition of an image of the sample SA on which one cycle of PCR process has been performed several times may be more effectively applied when determining a presence of target DNA with the sample SA, on which the amplification of target DNA has been performed several times.

Referring to FIG. 51, an image of the sample SA may be continuously acquired during one cycle. Alternatively, an image of the sample SA may be acquired at any point in time in which one cycle of PCR process is performed. Alternatively, an image of the sample SA may be acquired at a time point at which one cycle of PCR process is completed. Alternatively, an image of the sample SA may also be acquired at a plurality of points in time at which one cycle of PCR process is performed.

An image of the sample SA may be acquired at predetermined intervals. By comparing a plurality of images acquired at the predetermined intervals, an effect similar to that of a real-time PCR process in which amplification of target DNA may be checked in real time may be obtained. More specifically, by comparing the amounts of fluorescence of DNA and increasing rates of the amounts of fluorescence of DNA of a previously-acquired image and a subsequently-acquired image, there is an advantage in that more accurate diagnosis is possible.

10. Diagnostic Apparatus

Figure 52:
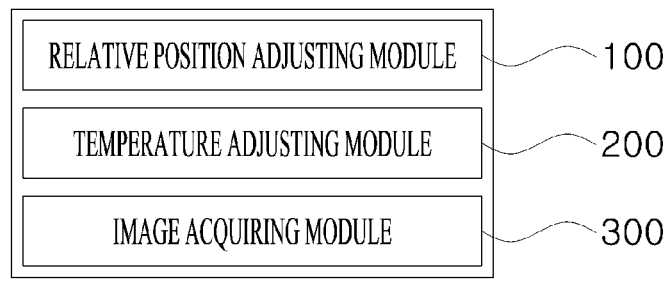
FIG. 52 is a block diagram of a diagnostic apparatus according to an embodiment of the present application.

FIG. 52 is a block diagram of a diagnostic apparatus according to an embodiment of the present application.

A diagnostic apparatus according to the present application may include a relative position adjusting module 100, a temperature adjusting module 200, and an image acquiring module 300. The diagnostic apparatus according to the present application may include more or less elements.

The relative position adjusting module 100 may perform a function of moving the patch PA and the plate PL relative to each other. The relative position adjusting module 100 may relatively move the patch PA and the plate PL to each other in a horizontal direction and/or a vertical direction.

The horizontal direction may refer to a direction parallel to a surface at which the plate PL and the patch PA come into contact. The vertical direction may refer to a direction perpendicular to the surface at which the plate PL and the patch PA come into contact.

Figure 53:
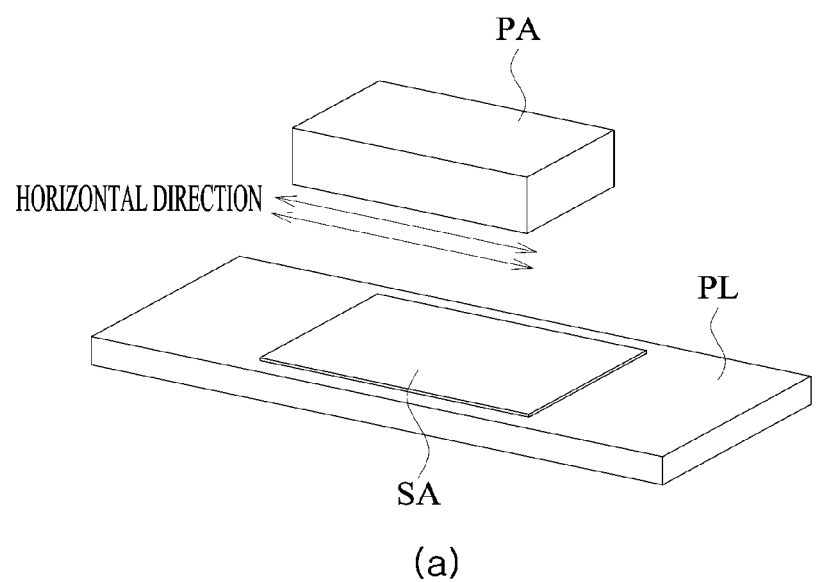
FIG. 53 is a conceptual diagram illustrating an example in which a structure of a diagnostic apparatus is moved due to a relative movement operation of a relative position adjusting module (100) according to an embodiment of the present application.
Figure 53:
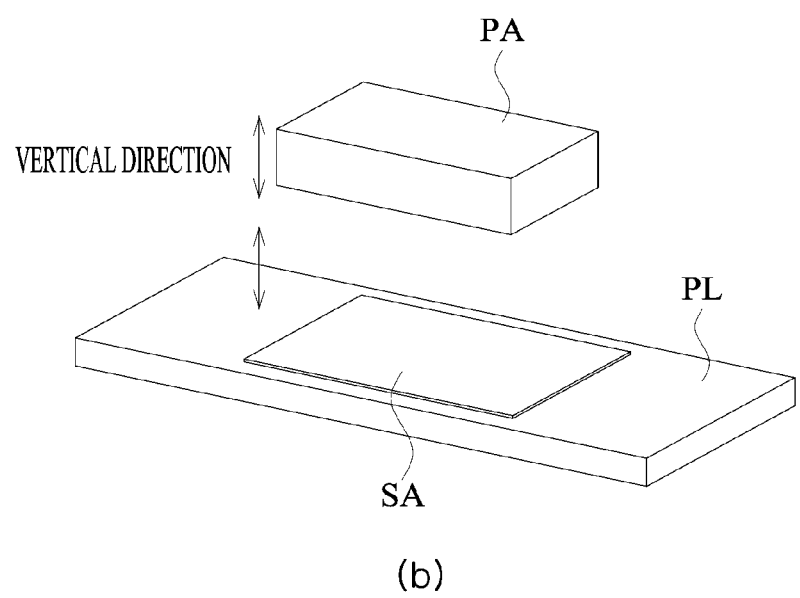

FIG. 53 is a conceptual diagram illustrating an example in which a structure of the diagnostic apparatus is moved due to a relative movement operation of the relative position adjusting module 100 according to an embodiment of the present application.

Referring to FIG. 53a, the relative position adjusting module 100 may relatively move the patch PA and the plate PL to each other in the horizontal direction and change a relative position of the patch PA on the plate PL.

The relative position adjusting module 100 may relatively move the patch PA and the plate PL to each other in the horizontal direction and perform a function of changing a patch PA that is disposed to come into contact with the sample SA. The changing of the patch PA to be contacted with the sample SA may allow a liquid substance provided from other patch PA to be delivered to the sample SA.

Referring to FIG. 53b, the relative position adjusting module 100 may relatively move the patch PA and the plate PL to each other in the vertical direction and control whether the plate PL and the sample SA are brought into contact. The contacting the patch PA and the sample SA may be involved in delivery of a substance contained in the patch PA to the sample SA.

The relative position adjusting module 100 may include a separate moving power source configured to relatively move the patch PA and the plate PL to each other in the horizontal direction and a separate moving power source configured to relatively move the patch PA and the plate PL to each other in the vertical direction. Alternatively, the relative position adjusting module 100 may use a single moving power source to relatively move the patch PA and the plate PL in the horizontal and/or vertical directions.

The temperature adjusting module 200 may perform a function of controlling temperature. The temperature adjusting module 200 may perform heating or cooling of the plate PL and/or the patch PA. Also, the temperature adjusting module 200 may perform a function of adjusting temperature of the sample SA and maintaining a constant temperature.

For example, the temperature adjusting module 200 may be used to adjust temperature of the sample SA to the above-described denaturation temperature, annealing temperature, and/or extension temperature.

The temperature adjusting module 200 may perform an exothermic operation and an endothermic operation. Accordingly, the temperature adjusting module 200 may include a heating element or a thermoelectric element. The temperature adjusting module 200 is not limited thereto, and any substance capable of heating may be used as the temperature adjusting module 200 without limitations.

The temperature adjusting module 200 may further include a temperature sensor as necessary. The temperature sensor may be used to identify a current temperature of a target that is subject to temperature adjustment.

The image acquiring module 300 may perform a function of acquiring an image of the sample SA. That is, to analyze genetic material amplified through the PCR process, the image acquiring module 300 may perform a function of acquiring an image of the sample SA on which the PCR process has been completed.

For example, the image acquisition may be performed by a method in which a partial image or an entire image of a plate PL or an entire plate PL is acquired, a method in which a partial image or an entire image of the patch PA is acquired, or a method in which an image of the sample SA is directly acquired.

The image acquiring module 300 may acquire an image of the sample SA in a state in which the PCR process has been ended or acquire an image of the sample SA in a state in which the PCR process is in progress.

The image acquiring module 300 may include a means for acquiring an image. For example, the image acquiring module 300 may include an image generator configured to generate an image, such as an image sensor including a complementary metal oxide semiconductor (CMOS) image sensor and a charge-coupled device (CCD) image sensor, a predetermined light beam generator configured to generate a beam of light that transmits through the sample SA, and/or an optical system configured to image a beam of light that has transmitted through the sample SA.

The image acquiring module 300 may also detect fluorescence or acquire a fluorescence image for quantitative and/or qualitative analysis of the sample SA.

An image generated from the image acquiring module 300 may have various magnifications. For example, the image may be an image with a magnification that enlarges the sample SA, an image with a fixated magnification, or may also be an image with a magnification that reduces the sample SA as necessary.

The image acquiring module 300 may also include a moving power member configured to move the plate PL on which the sample SA is located or move an element of the image acquiring module 300, thereby acquiring an image of the sample SA.

Hereinafter, a few embodiments of the PCR process using the patch PA according to an embodiment of the present application will be described in detail.

11. Embodiments

11.1 First Embodiment

Figure 54:
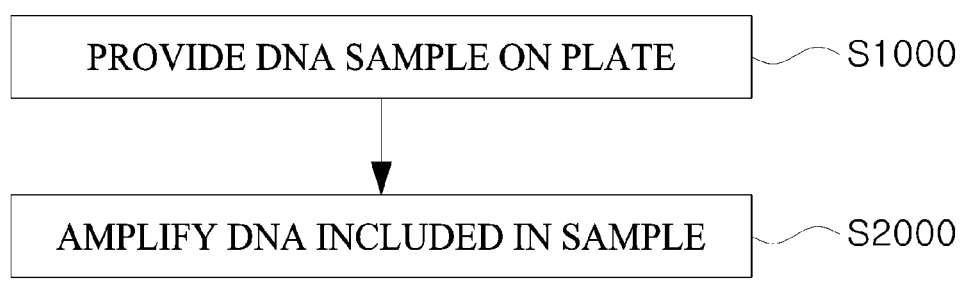
FIG. 54 is a flowchart for describing a PCR process according to an embodiment of the present application.

FIG. 54 is a flowchart for describing a PCR process according to an embodiment of the present application.

To perform the PCR process, a DNA sample SA may be provided on the plate PL (S1000). As described above, the sample SA may be provided in a single layer on the plate PL. The sample SA provided in a single layer may be fixated on the plate PL using a general method.

When the sample SA is provided on the plate PL, a procedure for amplifying the DNA included in the sample SA (S2000) may be performed. To amplify the DNA, as described above, reagents RA and temperature conditions required for the denaturation step, the annealing step, and the extension step should be provided to the sample SA.

In the PCR process according to an embodiment of the present application, when a single patch PA is used in the PCR process, the PCR process may be performed in the following order.

Figure 55:
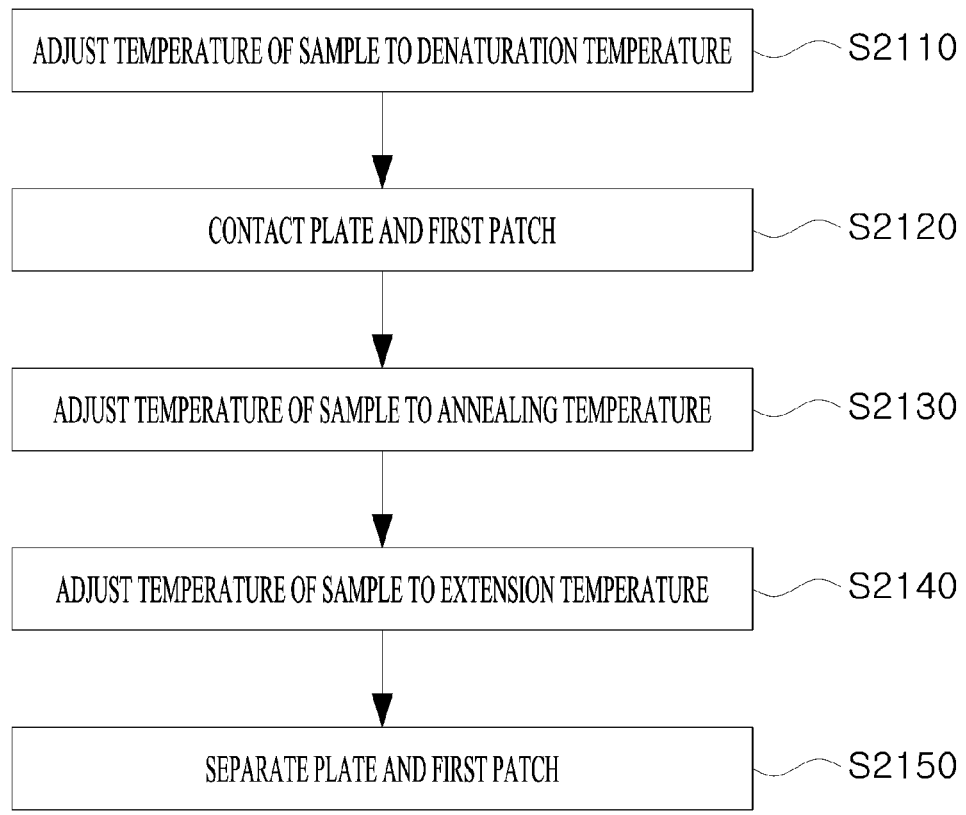
FIG. 55 is a flowchart for describing amplifying a DNA included in a sample according to an embodiment of the present application.

Referring to FIG. 55, the plate PL on which the sample SA is located may be heated so that temperature of the sample SA is adjusted to the denaturation temperature (S2110).

The first patch PA may be brought into contact with the heated plate PL (S2220). Here, the "first patch PA" merely refers to any patch PA that may be used in the PCR process and is not limited to the above-described first patch PA.

Some or all of reagents RA used in the annealing step may be contained in the first patch PA. Alternatively, a liquid substance for providing a moist environment to the plate PL may be contained in the first patch PA.

Via contact between the first patch PA and the plate PL, the reagents RA contained in the first patch PA may be provided to the plate PL.

After the contact between the first patch PA and the plate PL, the temperature of the sample SA may be adjusted to the annealing temperature (S2130). The temperature of the sample SA may be cooled to the annealing temperature and maintained at the annealing temperature.

The temperature of the sample SA may be re-adjusted to the extension temperature (S2140). The temperature of the sample SA may be increased to the extension temperature and maintained at the extension temperature. As a method of adjusting the temperature of the sample SA, as described above, the patch PA and/or the plate PL may be heated or cooled, or the sample SA may also be directly heated or cooled.

The above-described heat treatment process of the PCR may be repeated an predetermined number of times. This may be done to increase the amount of amplified DNA included in the sample SA.

When the above-described process for DNA amplification is completed, the contact between the plate PL and the first patch PA may be released (or disconnected)(S2150).

However, in the present embodiment, the contact between the first patch PA and the plate PL may be maintained while the temperature of the sample SA is being increased to the annealing temperature or while the temperature of the sample SA is maintained at the annealing temperature. Alternatively, the contact between the first patch PA and the plate PL may also be maintained while the temperature of the sample SA is being adjusted to the denaturation temperature or while the temperature of the sample SA is maintained at the denaturation temperature. Also, the contact between the first patch PA and the plate PL may be performed several times during one cycle (that is, while each of the denaturation step, the annealing step, and the extension step are performed once).

11.2 Second Embodiment

In the PCR process in which a plurality of patches PA are used according to an embodiment of the present application, the PCR process may be performed in the following order.

Figure 56:
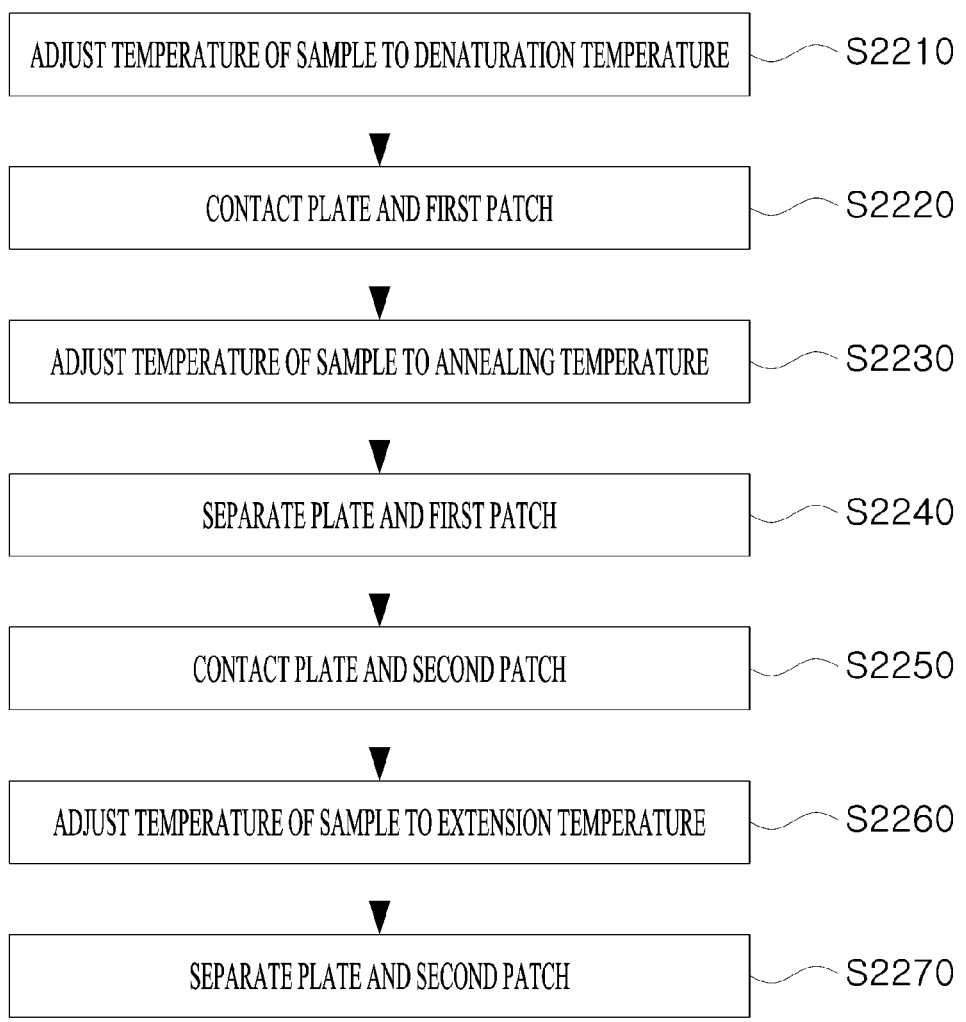
FIG. 56 is a flowchart for describing amplifying a DNA included in a sample according to an embodiment of the present application.

Referring to FIG. 56, the temperature of the sample SA may be adjusted to the denaturation temperature (S2210). To adjust the temperature of the sample SA, the temperature of the plate PL may be adjusted.

The first patch PA may be contacted with the plate PL on which the sample SA is located (S2220). The first patch PA may include some or all of reagents RA required in the annealing step. Via contact between the sample SA and the patch PA, some or all of the reagents RA contained in the patch PA may move to the plate PL. This is due to the function of the patch PA in which a region in which a substance is movable expands due to contact between the patch PA and the plate PL.

The temperature of the sample SA may be adjusted to the annealing temperature (S2230). While the temperature of the sample SA is maintained at the annealing temperature, some of the reagents RA that have moved from the patch PA may bind to the DNA included in the sample SA.

The contact between the first patch PA and the plate PL may be released (S2240). Via a release of the contact between the first patch PA and the plate PL, some of the reagents RA provided by the first patch PA may be delivered to the plate PL. The reagents RA delivered to the plate PL may be in a state of having been bound to the sample SA.

The second patch PA may come into contact with the plate PL (S2250) upon a release of the contact between the first patch PA and the plate PL. The second patch PA may include some or all of the reagents RA required in the extension step. Some or all of the reagents RA contained in the second patch PA may move to the plate PL.

The temperature of the sample SA may be adjusted to the extension temperature (S2260). The temperature of the sample SA may be increased to be adjusted to the extension temperature and may be maintained at the desired temperature. While the temperature of the sample SA is maintained at the extension temperature, the dNTP may bind to the DNA.

The second patch PA and the plate PL may be separated (S2270).

Similar to when a single patch PA is used, the above-described heat treatment process of the PCR may be repeated a predetermined number of times.

The first patch PA and the plate PL may be contacted several times and the second patch PA and the plate PL may be also contacted several times during one cycle (that is, while the denaturation step, the annealing step, and the extension step are performed once).

However, in the present embodiment, the first patch PA and the plate PL may be brought into contact while the temperature of the sample SA is adjusted to the annealing temperature or while the temperature of the sample SA is maintained at the annealing temperature. Alternatively, the first patch PA and the plate PL may be brought into contact while the temperature of the sample SA is adjusted to the denaturation temperature or while the temperature of the sample SA is maintained at the denaturation temperature.

The second patch PA and the plate PL may be brought into contact while the temperature of the sample SA is adjusted to the extension temperature or while the temperature of the sample SA is maintained at the extension temperature. Alternatively, the second patch PA and the plate PL may be brought into contact while the temperature of the sample SA is adjusted to the annealing temperature or while the temperature of the sample SA is maintained at the annealing temperature.

In the present embodiment, the "first patch PA" and the "second patch PA" merely refer to any patch PA that may be used in the PCR process, and are not limited to the above-described first patch PA or second patch PA. Also, the "first patch PA" and the "second patch PA" refer to separate patches PA but do not necessarily mean that the first patch PA and the second patch PA should contain different reagents RA.

The separation of the first patch PA and the second patch PA from the plate PL may be omitted. For example, by bringing the first patch PA and the second patch PA into contact while the separation between the first patch PA and the plate PL (S2240) is not performed, the reagents RA contained in the second patch PA may be made to move to the plate PL.

11.3 Third Embodiment

The PCR process according to an embodiment of the present application may perform diagnoses of various diseases through a one-time PCR process.

The PCR process for various genetic materials may be performed using a patch PA with divided regions. The patch PA may be divided into at least two or more regions.

The patch PA according to the present application may form a water film (aquaplane, hydroplane) through contact with the sample SA, and a liquid substance captured in the patch PA may move inside the water film. Using such a feature, the patch PA may deliver the substance to an external region.

In this way, while maintaining still the form of the substance contained in the patch PA even after contact with an external substance, the patch PA performs delivery of the substance in an area similar to a contact area of the patch PA. By such a function of the patch PA, a dividing of a single patch PA may make that movement of a substance is not possible between the divided regions, and different reagents RA may be delivered to different regions.

Figure 57:
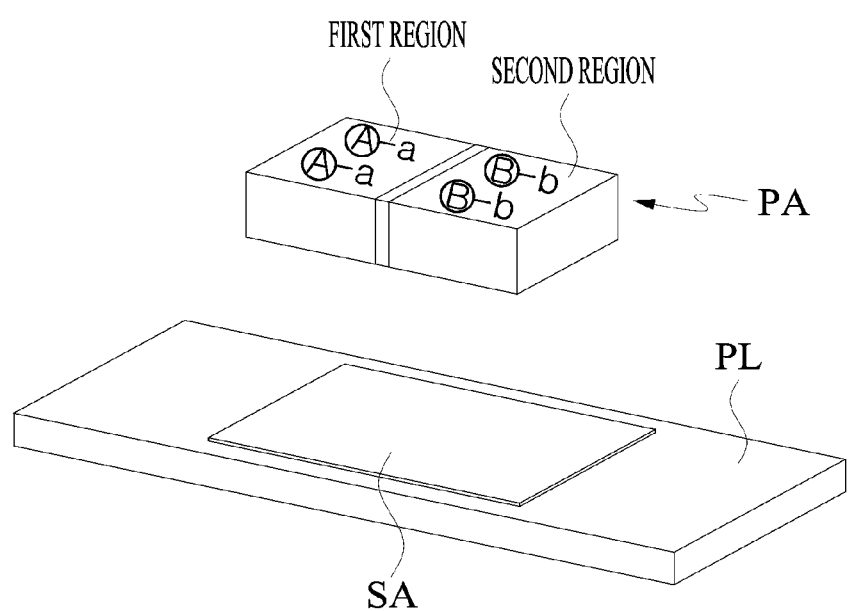
FIG. 57 is a view for describing a PCR process for a plurality of target genetic materials according to an embodiment of the present application.

FIG. 57 is a view for describing a PCR process for a plurality of target genetic materials according to an embodiment of the present application.

Referring to FIG. 57, primers for different target DNAs may be contained in a first region and a second region. When the PCR process is performed using a patch PA in which primers that correspond to different target DNAs are separately contained in a first region and a second region, an image of the sample SA may be acquired, and diagnosis may be performed for the plurality of target genetic materials.

For example, whether fluorescence is detected from one region of the sample SA that corresponds to the first region may be checked through a fluorescence image, and whether a genetic material that corresponds to the primer contained in the first region is present in the sample SA may be determined. Also, whether fluorescence is detected from one region of the sample SA that corresponds to the second region may be identified, and whether a genetic material that corresponds to the primer contained in the second region is present in the sample SA may be determined.

More specifically, both the PCR process using a single patch PA and the PCR process using a plurality of patches PA may be applied to the PCR process using a divided patch PA.

However, taking into consideration that a mechanism in which reagents RA are delivered between the patch PA and the plate PL is related to water film formation, a more accurate diagnosis may be performed through the PCR process using only a divided patch PA (that is, using a single patch PA). This is due to an independent water film being generated in a region of the sample SA corresponding to the first region and a region of the sample SA corresponding to the second region until the PCR process ends.

11.4 Fourth Embodiment

For diagnosis of various diseases as with the third embodiment, a patch PA in which multiple types of primers, to which different types of fluorescent color development reagents RA are attached, are contained may be used.

More specifically, for a sample SA in the PCR process using multiple types of primers to which different types of fluorescent color development reagents RA are attached, wavelength bands of light irradiated to the sample SA during image acquisition may vary so that diagnosis for various genetic materials is possible.

Figure 58:
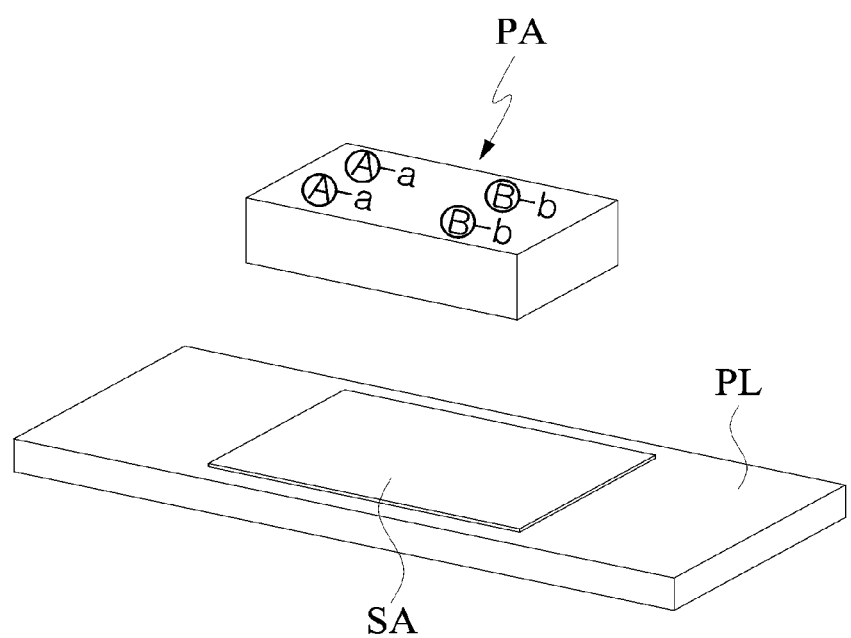
FIG. 58 is a view for describing a PCR process for a plurality of target genetic materials according to an embodiment of the present application.
Figure 59:
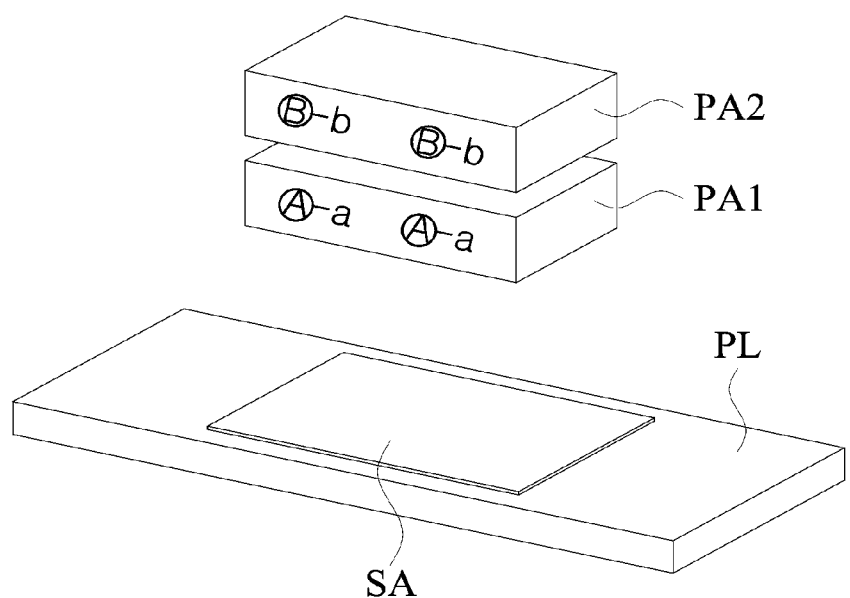
FIG. 59 is a view for describing a PCR process for a plurality of target genetic materials according to an embodiment of the present application.

FIGS. 58 and 59 are views for describing a PCR process for a plurality of target genetic materials according to an embodiment of the present application.

Referring to FIG. 58, a single patch PA according to an embodiment of the present application may include various primers that correspond to various specific sequences of genetic materials. Regarding the various primers, a single fluorescent substance may correspond to a single sequence. That is, a fluorescent substance having wavelength band "a" may be bound to a primer that corresponds to a genetic sequence A, and a fluorescent substance having wavelength band "b" may be bound to a primer that corresponds to a genetic sequence B.

The PCR process may be performed using the patch PA including the various primers. In this case, the above-described method of the PCR process using a single patch PA or the PCR process using a plurality of patches PA may be applied. The patch PA including the various primers may further include a dNTP, a dNA polymerase, a coenzyme, and/or a buffer solution.

Referring to FIG. 59, a patch according to an embodiment of the present application may include primers that correspond to specific sequences of genetic materials. The primers may bind to fluorescent substances that develop different colors when target genetic materials are different.

The patch that includes the primers may be one or more. For example, the PCR process may be performed using a first patch that includes a first primer (a primer that corresponds to a genetic sequence A) and a second patch that includes a second primer (a primer that corresponds to a genetic sequence B).

The patches may be in contact with the sample SA at a time point at which the primers need to be provided to the sample SA.

At the time point at which the primers need to be provided to the sample SA, a first patch PA1 may be provided to the sample SA, and a second patch PA2 may come into contact with the first patch PAL Alternatively, at the time point at which the primers need to be provided to the sample SA, the second patch PA2 may be provided to the sample SA, and the first patch PA1 may come into contact with the second patch PA2.

An image of a sample SA on which the PCR process has been completed or is in progress may be obtained. In this case, images related to a plurality of wavelength bands may be acquired for the image of the sample SA. A plurality of filters may be used for the acquisition of the images related to the plurality of wavelength bands.

More specifically, light in a wavelength band A may be irradiated to identify whether a genetic material that corresponds to a primer, to which a fluorescent substance having the wavelength band A is bound, is present, and light in a wavelength band B may be irradiated to check whether a genetic material that corresponds to a primer, to which a fluorescent substance having the wavelength band B is bound, is present. In this way, diagnosis for multiple diseases may also be performed in the PCR process using a single patch.

11.5 Fifth Embodiment

Figure 60:
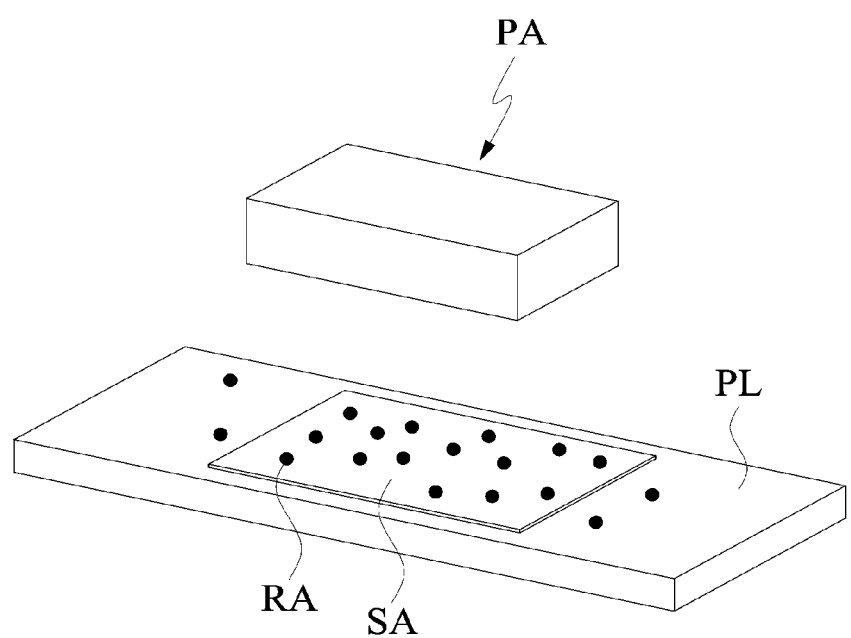
FIG. 60 is a view for describing a PCR process using a plate, on which a reagent is provided, and a patch according to an embodiment of the present application.
Figure 61:
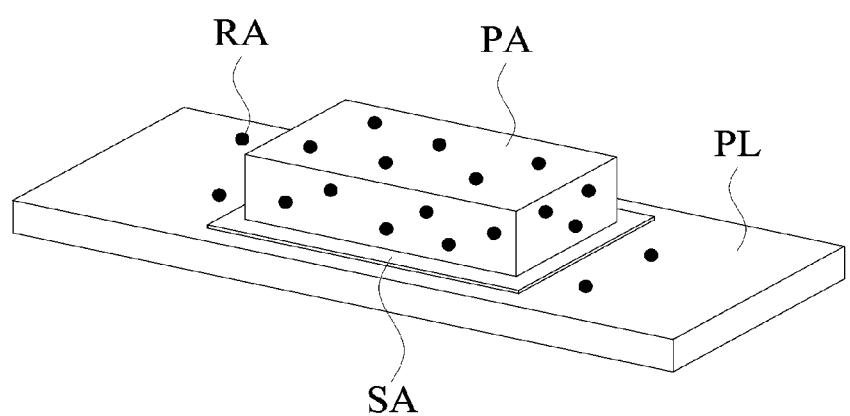
FIG. 61 is a view for describing a PCR process using a plate, on which a reagent is provided, and a patch according to an embodiment of the present application.

FIGS. 60 and 61 are views for describing a PCR process using a plate PL on which a reagent RA is provided and a patch PA according to an embodiment of the present application.

Referring to FIG. 60, a part or all of reagents RA used in the PCR process may be applied on the plate PL. Also, when a sample SA is smeared on the plate PL, the reagents RA applied on the plate PL may be coated thereon to maintain uniformity of the reagents RA.

The plate PL on which the reagents RA are provided in advance may be manufactured using a method in which the reagents RA are applied on the plate PL and the plate PL is frozen and dried. Through such a process, the reagents RA may have a predetermined force of resistance and be maintained at predetermined positions on the plate PL.

Referring to FIG. 61, the plate PL on which the reagents RA are coated may receive a moist environment from the patch PA. When the patch PA comes into contact with the plate PL, a liquid substance contained in the patch PA may move to the plate PL, and due to the movement of the liquid substance, a moist environment may be provided to the plate PL. When the reagents RA coated on the plate PL receive the moist environment by the patch PA, conditions for reaction between the reagents and the sample SA provided on the plate PL are provided in the sample SA. When the temperature of the sample SA is adjusted to a suitable temperature, the denaturation step, the annealing step, or the extension step may be performed on the sample SA.

Further, in the present embodiment, creation of conditions that allow the sample SA to react with the reagents RA due to the contact between the patch PA and the plate PL derives an effect similar to that of the above-described provision of the reagents RA to the sample SA due to contact between the patch PA and the plate PL.

Accordingly, by applying a PCR process using a various type of a patch PA that are disclosed herein or may be easily derived from embodiments disclosed herein, the conditions that allow the sample SA to react with the reagents RA may be provided using the plate PL on which the reagents RA are applied, and the PCR process may be performed using the plate PL on which the reagents RA are applied.

For example, the PCR process may be performed using the plate PL on which the reagents RA are applied and the patch PA capable of providing a moist environment.

Figure 62:
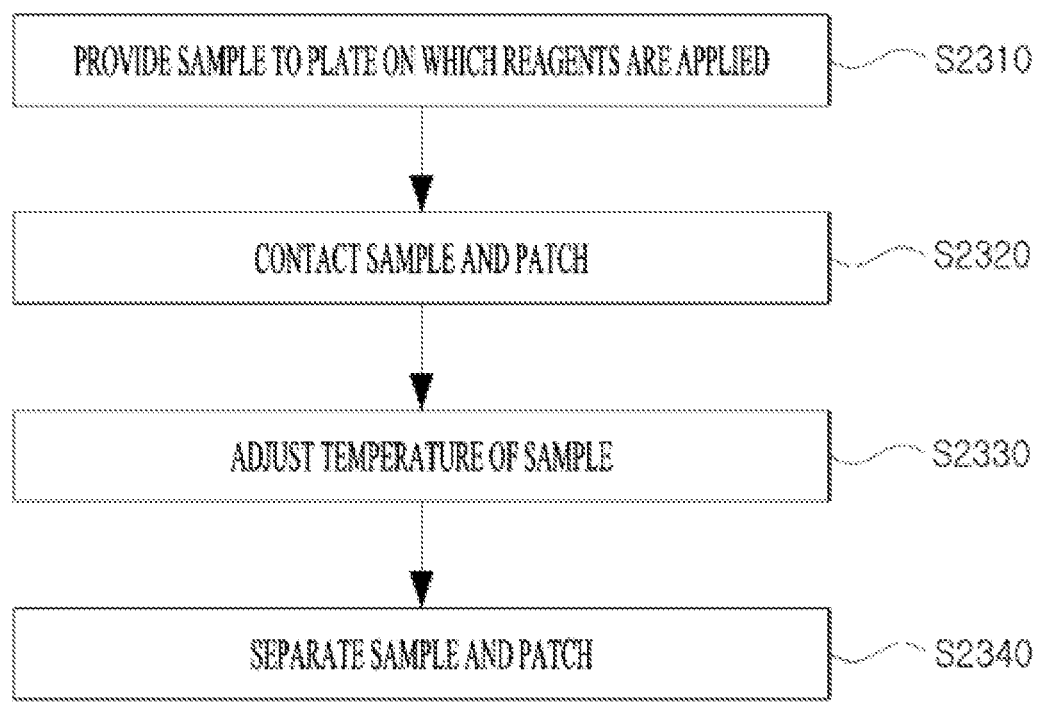
FIG. 62 is a flowchart for describing a PCR process using a plate, on which a reagent is provided, and a patch according to an embodiment of the present application.

FIG. 62 is a flowchart for describing a PCR process using a plate PL, on which a reagent RA is provided, and a patch PA according to an embodiment of the present application.

In the PCR process, a sample SA may be provided on a plate PL on which reagents RA are applied (S2310). The reagents RA applied on the plate PL (hereinafter "first substance") may be a part or all of reagents RA used in the PCR process. The sample SA provided on the plate PL may be fixated on the plate PL so that the sample SA is prevented from being absorbed into the patch PA when contact between the patch PA and the plate PL is released.

The sample SA provided on the plate PL may be contacted with the patch PA (S2320). As described above, the first substance that receives the moist environment due to the contact becomes to have mobility. Accordingly, the first substance may move within a region in which the sample SA is applied and may also move to the patch PA. When the sample SA and the patch PA come into contact, a liquid substance provided to the plate PL by the patch PA (hereinafter "second substance") may move to the sample SA.

When the sample SA and the patch PA are in contact, the temperature of the sample SA may be adjusted (S2330). The temperature of the sample SA may be adjusted to each of the denaturation step, the annealing step, and the extension step sequentially. While the temperature of the sample SA is adjusted and maintained at a suitable temperature, the first substance may bind to the DNA included in the sample SA. Alternatively, the second substance may bind to the DNA included in the sample SA. Alternatively, the second substance may bind to the first substance. Through such a process, the DNA included in the sample SA may be amplified.

When the DNA amplification has ended, the sample SA and the patch PA may be separated (S2340). Due to the separation between the sample SA and the patch PA, the liquid substance on the plate PL, excluding the sample SA and a part of substances bound to the sample SA, may be re-absorbed into the patch PA. Alternatively, due to the separation between the sample SA and the patch PA, the sample SA and the substance provided on the plate PL may be absorbed into the patch PA.

The above-described few steps may be repeated sequentially in the above-given order or in a slightly different order.

Also, some of the above-described steps may be omitted or performed by adding another procedure.

11.6 Sixth Embodiment

Additional effects and improvement examples due to control of contact between the patch PA and the plate PL that is applicable to the PCR process according to an embodiment of the present application will be described in more detail.

Figure 63:
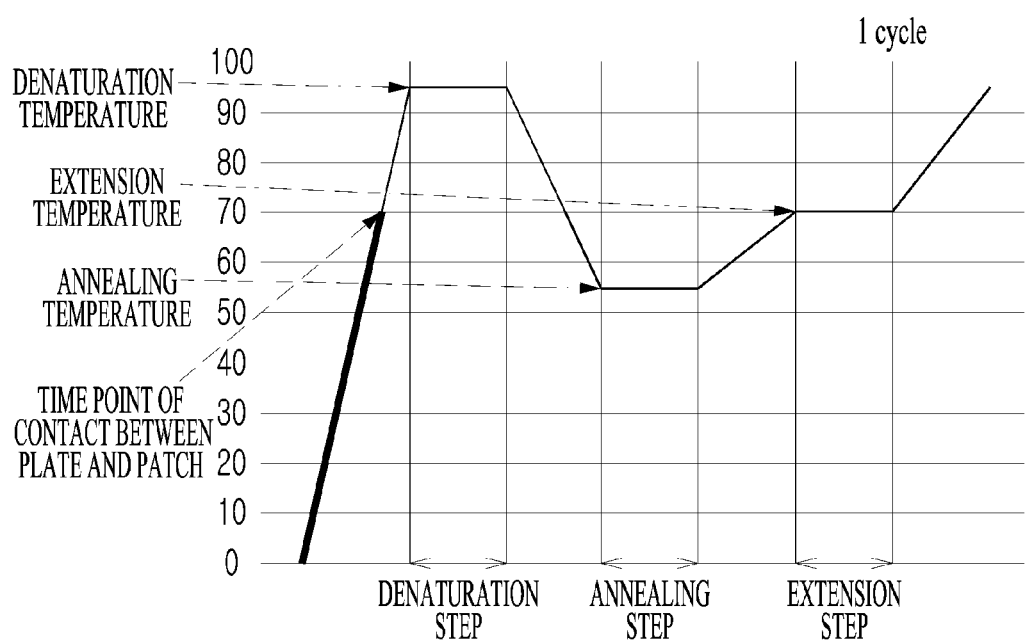
FIG. 63 is a flowchart of a method of controlling contact between a patch and a plate according to an embodiment of the present application.

FIG. 63 is a flowchart of a method of controlling contact between a patch PA and a plate PL according to an embodiment of the present application.

The present embodiment may be applied to a process in which temperature of the plate PL is adjusted to the denaturation temperature.

The denaturation temperature is higher than temperature of a generally-provided sample SA or an extension temperature in a previous cycle. Accordingly, to adjust the temperature of the sample SA to the denaturation temperature, heating the plate PL (S2410) may be required. The heating may be performed by the temperature adjusting module 200.

While the plate PL is being heated, the temperature of the plate PL may be monitored continuously or at predetermined time interval (S2420). Whether the patch PA and the plate PL come into contact may be controlled when the checked temperature of the plate PL is higher than or equal to a preset reference temperature (S2430).

For example, when the patch PA is manufactured with a material that may be deformed by heat, there is a problem in that the patch PA may be degenerated when the temperature of the plate PL is further increased in comparison to the denaturation temperature of the patch PA. To solve this problem, the temperature of the plate PL may be monitored while the plate PL is being heated, and when the temperature of the plate PL is higher than or equal to a reference temperature (that is, temperature at which the patch PA is denatured), the plate PL and the patch PA may be separated. The contact between the patch PA and the plate PL may also be adjusted by the relative position adjusting module 100.

11.7 Seventh Embodiment

In a modified example of the sixth embodiment, the contact between the patch PA and the plate PL may be controlled in accordance with temperature of the sample SA.

In the modified example, as with the above-described embodiment, the temperature of the sample SA provided on the plate PL may be monitored continuously or at predetermined time interval while the plate PL is being heated. Whether the patch PA and the plate PL come into contact may be controlled when the monitored temperature of the sample SA is higher than or equal to a preset reference temperature.

Figure 64:
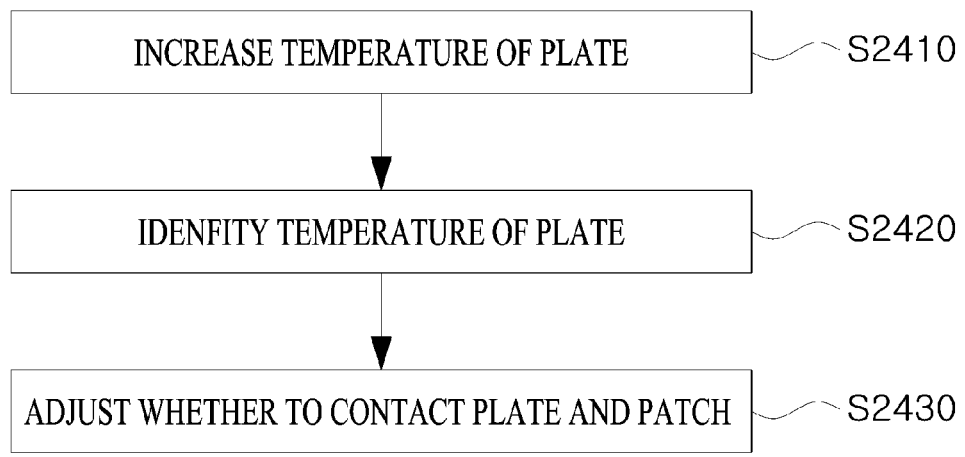
FIG. 64 is a view for describing a time of contact between a patch and a plate according to an embodiment of the present application.

For example, referring to FIG. 64, the sample SA may be heated in a process in which the temperature of the sample SA is adjusted to the denaturation temperature. When the temperature of the sample SA is higher than about 70° C., the patch PA (for example, a patch PA that includes a primer) may come into contact with the plate PL. When the temperature of the sample SA is higher than or equal to a reference temperature, contact between the patch PA and the plate PL may be controlled so that reagents RA are provided to the sample. In this way, an effect similar to that of a general hot-start PCR process may be implemented. This is significant in that the same effect may be obtained even without an inconvenient process of the conventional hot-start PCR in which wax is used for separating upper and lower substances.

11.8 Eighth Embodiment

In the PCR process according to an embodiment of the present application, an embodiment in which temperature of the patch PA is adjusted to adjust temperature of the sample SA will be described in more detail.

As described above, to control the temperature of the sample SA to a temperature suitable for each step (for example, denaturation step), temperatures of the patch PA and/or the plate PL may be controlled.

Figure 65:
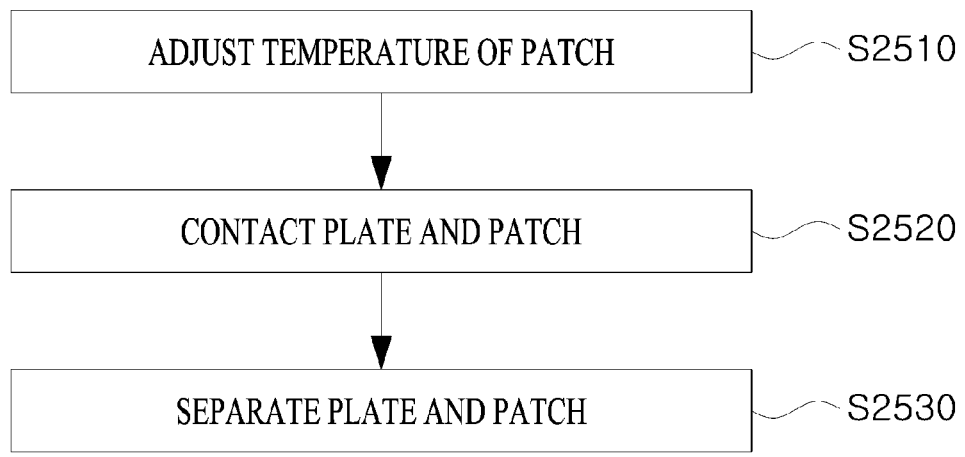
FIG. 65 is a flowchart for describing a method in which temperature of a patch is adjusted to adjust temperature of a sample according to an embodiment of the present application.

FIG. 65 is a flowchart for describing a method in which temperature of a patch PA is adjusted to adjust temperature of a sample SA according to an embodiment of the present application.

To control the temperature of the sample SA, the temperature of the patch PA may be adjusted (S2510). To adjust the temperature of the patch PA, temperature of at least a part of a region that comes into contact with the patch PA may be adjusted. The adjustment of the temperature of the patch PA may be performed by the temperature adjusting module 200.

When the temperature of the patch PA is adjusted to a temperature suitable for a current step (for example, in the case of the annealing step, the temperature of the patch PA is adjusted to a temperature for adjusting the temperature of the sample SA to the annealing temperature), the patch PA and the plate PL may come into contact. In this case, the patch PA may include a part or all of reagents RA required for the current step.

The patch PA and the plate PL may come into contact and remain in contact for a predetermined duration. This is to provide time for the temperature of the sample SA to be adjusted to a suitable temperature in each step.

The plate PL and the patch PA may be separated (S2530). The plate PL and the patch PA may be separated for heating or cooling of the patch PA.

When a plurality of patches PA are used in the PCR process, temperatures of some or all of the plurality of patches PA may be adjusted. For example, when a first patch PA, a second patch PA, and a third patch PA are used in the PCR process, the temperature of the sample SA may be adjusted using the first patch PA and the second patch PA, and a temperature of the third patch PA may not be adjusted.

When a plurality of patches PA are used in the PCR process, temperatures of at least some of the plurality of patches PA may be adjusted to different temperatures.

For example, a temperature of each of the plurality of patches PA may be adjusted to a temperature suitable for each step. The first patch PA may be heated to an optimal temperature in order to adjust temperature of the sample SA that is in contact with the first patch PA in the denaturation step, the second patch PA may be heated to an optimal temperature in order to adjust temperature of the sample SA that is in contact with the second patch PA in the annealing step, and the third patch PA may be heated to an optimal temperature in order to adjust temperature of the sample SA that is in contact with the third patch PA in the extension step.

Temperatures of at least some of the plurality of patches PA may be adjusted sequentially. Temperatures of at least some of the plurality of patches PA may be adjusted simultaneously.

Figure 66:
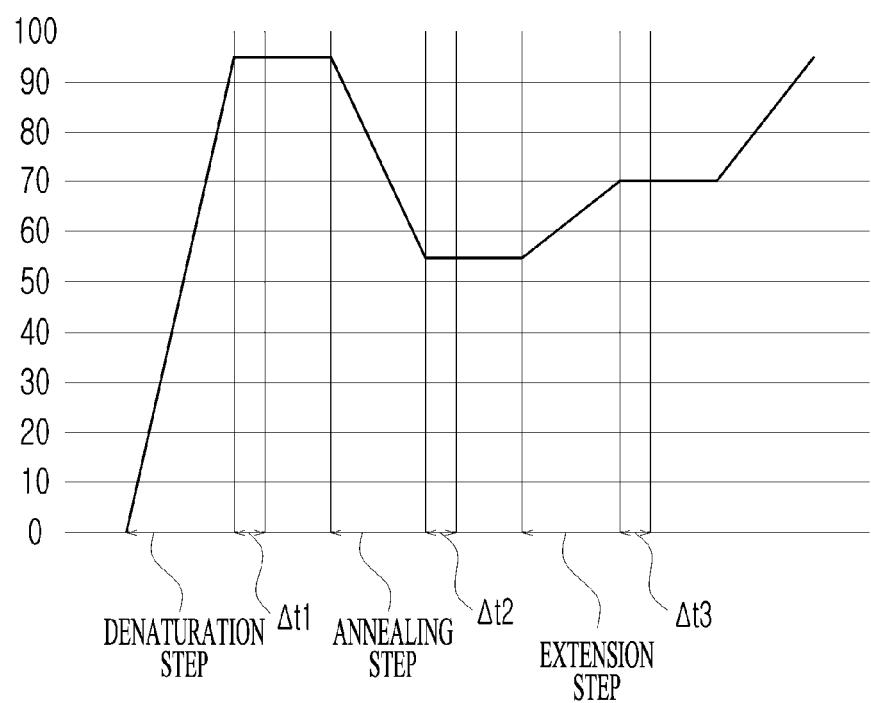
FIG. 66 is a view for describing an effect of using a plurality of patches to adjust temperature of a sample according to an embodiment of the present application.

FIG. 66 is a view for describing an effect of using a plurality of patches PA to adjust temperature of a sample SA according to an embodiment of the present application.

In the case of the present embodiment, a different patch PA is used for each step so that at least some of the reagents RA used in each step are contained in each patch PA, and a temperature of each patch PA is adjusted.

Particularly, while one of the patches PA is in contact with the sample SA and adjusts the temperature of the sample SA, other patch PA among the patches PA may be heated, cooled, or maintained at a desired temperature. In this way, it is expected that time taken for temperature adjustment in the PCR process according to the present embodiment would be shorten. More specifically, time $\Delta t2$ is shortened in a period in which the temperature of the sample SA is adjusted to the annealing temperature, and time $\Delta t3$ is shortened in a period in which the temperature of the sample SA is adjusted to the extension temperature. In this way, a faster PCR process may be performed.

In a general PCR process, a large amount of time is taken mostly for adjusting temperatures of the sample SA and the reagents RA. Taking this into consideration, it is expected that the PCR process using the patch PA according to the present application may be efficiently used in PCR testing.

Also, as described above, when the temperature of the sample SA is adjusted using a plurality of patches PA as necessary, the plate PL may be additionally used for adjusting temperature of the sample SA. Temperature adjustment by the patch PA and temperature adjustment by the plate PL may be sequentially performed or simultaneously performed. In such a case, efficiency of temperature control of the sample SA using the plurality of patches PA may be significantly improved in comparison to a general PCR process.

11.9 Ninth Embodiment

In the PCR process, when the temperature of the patch PA is adjusted to adjust the temperature of the sample SA, a separate material with high heat conductivity, instead of the patch PA, may adjust the temperature of the sample SA in the denaturation step.

For example, the separate material may be a metal material. That is, temperature of the metal material may be adjusted in the adjusting of the temperature of the patch PA (S2510), and the plate PL and the metal material may be contacted for adjusting temperature of the sample SA.

The adjustment of temperature of the sample SA using the metal material may be performed in a process in which the temperature of the sample SA is adjusted to the denaturation temperature. This may be an advantage since reagents RA are not required to be provided to the sample SA and the temperature of the sample SA has to be adjusted to about 90° C. or higher in the denaturation step. In other words, there is no need to deliver the reagents RA to the sample SA using the delivery function of the patch PA, there is no possibility that the patch PA may be denatured by heat at about 90° C., and due to high heat conductivity of the metal material, time taken for the PCR process may be shortened.

In relation to this, the temperature adjusting module 200 may include a thermoelectric element. For example, when the thermoelectric element (for example, a Peltier element) is used, absorption or generation of heat due to electric current (that is, the Peltier effect) may be caused. The adjustment of temperature using the thermoelectric element has advantages in that a target that is subject to temperature adjustment may be cooled as well as heated, heat absorption and heat generation may be freely switched along a direction of current, and a temperature is easily kept constant.

11.10 Tenth Embodiment

The PCR process according to an embodiment of the present application may be performed on an RNA sample SA. When the PCR process is performed on the RNA sample SA, the RNA sample SA may be synthesized into DNA through a reverse transcription PCR process. A general PCR may be performed on the synthesized DNA.

Figure 67:
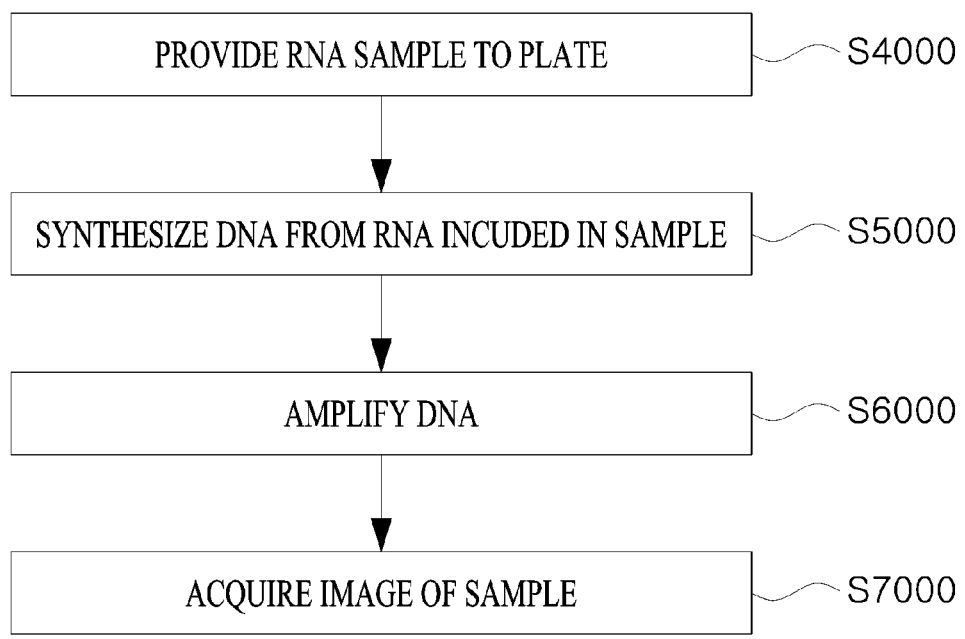
FIG. 67 is a flowchart for describing a process of performing a PCR process on an RNA sample according to an embodiment of the present application.

FIG. 67 is a flowchart for describing a process of performing a PCR process on an RNA sample according to an embodiment of the present application.

In the PCR process according to the present embodiment, the RNA sample SA may be provided on the plate PL (S4000). The providing the RNA sample SA on the plate PL (S4000) may be performed similarly to the providing the DNA sample SA on the plate PL (S1000).

The RNA sample SA provided on the plate PL may be synthesized into the DNA (S5000). Messenger RNA (mRNA) included in the RNA sample SA may be synthesized into complementary DNA (cDNA).

To synthesize the DNA from the RNA included in the sample SA, a reverse transcriptase, a primer, and a dNTP may be used. Although, essentially, the DNA polymerase among the reagents RA being used has to be replaced with a reverse transcriptase in a procedure in which the DNA is synthesized from the RNA, the procedure may be similar to the procedure in which the DNA is amplified. Accordingly, even when the sample SA is RNA, the technical spirit and embodiments disclosed herein are applicable.

However, to assist in understanding the present application, an example of a process in which DNA is synthesized from RNA will be described.

As an example, patches PA used in the DNA synthesis process may be a first patch PA that includes a primer and a second patch PA that includes dNTP and a reverse transcriptase. Accordingly, the DNA synthesis process may be performed similarly to the PCR process described above with reference to FIG. 56.

To deform an RNA secondary structure, the RNA sample SA may be heated. After the RNA sample SA is heated, temperature thereof may be maintained for a predetermined duration. A preferred temperature may be changed in accordance with manuals of the reagents RA being used.

The plate PL and the first patch PA may come into contact. The RNA sample SA may come into contact with the first patch PA, and the primer that has been contained in the first patch PA may move to the RNA sample SA due to the first patch PA.

The temperature of the RNA sample SA may be adjusted so that the primer may bind to the RNA. When the temperature of the RNA is maintained for a predetermined duration, the primer may bind to a portion of the sample SA. Then, the plate PL and the first patch PA may be separated.

The plate PL and the second patch PA may come into contact. Due to contact between the RNA sample SA and the second patch PA, the reagents RA contained in the second patch PA may move to the RNA sample SA. The reagents RA moved to the sample SA may be the dNTP and the reverse transcriptase.

The temperature of the sample SA may be adjusted so that the dNTP may bind to the RNA and the RNA may be synthesized into the DNA. When the temperature of the RNA is maintained for a predetermined amount of time, DNA may be synthesized.

The RNA sample SA may be cooled as necessary for a predetermined period prior to the movement of the dNTP and the reverse transcriptase to the RNA sample SA. For example, the present process may be performed when a reaction temperature of the reverse transcriptase is lower than a temperature in the range of 55 to 60° C.

When the DNA is synthesized from the RNA, a PCR may be performed on the synthesized DNA. That is, the synthesized DNA may be amplified (S6000). The process of amplifying the DNA may be a PCR process using a patch PA that may be performed in accordance with the present specification or may be a general PCR process.

An image of the sample SA on which the DNA amplification has been completed may be acquired (S7000).

In the PCR process disclosed herein, each of the above-described steps may be omitted, another procedure may be additionally performed, and the PCR process may be modified and practiced to the extent that the PCR process may be easily performed by those of ordinary skill in the art to which the present application pertains.

For example, in addition to being usable in a PCR process for DNA amplification, the patch PA may also be used to check whether a target DNA is included in a sample SA in which DNAs have already been randomly amplified.

More specifically, when the sample SA in which the DNA is amplified is smeared on the plate PL, a primer that corresponds to a sequence of a target DNA that is desired to be detected may be contained in the patch PA. In this case, a label such as a fluorescent substance may be attached to the primer.

The patch PA in which the primer is contained and the plate PL may come into contact and be separated. Through contact and separation between the patch PA and the plate PL, the primer that has been contained in the patch PA may bind to some of the DNA included in the sample SA, and the remaining primer that fails to bind to the DNA may be re-absorbed into the patch PA.

When a DNA that binds complimentarily to the primer is present in the sample SA, fluorescence may be detected from the sample SA. Accordingly, whether a target DNA is included in the sample SA may be identified.

Further, a sample SA that has gone through the PCR process may be contained in the patch PA. In this case, a label such as a fluorescent substance may be attached to the DNA (or RNA) included in the sample SA. A single strand of a DNA molecule (for example, a DNA probe) may be applied on the plate PL that comes into contact with the patch PA.

As described above, the plate PL and the patch PA may come into contact and be separated. Through contact and separation between the patch PA and the plate PL, DNA molecules that have been applied on the plate PL may bind to the DNA (or RNA) contained in the patch PA, and a sample SA, excluding the DNA (or RNA) bound to the DNA molecules, may be re-absorbed into the patch PA.

When DNA (or RNA) that binds complementarily to the DNA molecules is present in the sample SA, fluorescence may be detected from a region in which the DNA molecules are located. Consequently, whether a target DNA is included in the sample SA may be checked.

The "first patch PA," the "second patch PA," and the third patch PA" used herein refer to separate patches PA which are physically separated, but do not necessarily mean that the patches PA contain different reagents RA.

The diagnostic apparatus according to the present application may perform the PCR process described above. Description of the process in terms of a mechanical aspect will be omitted since it is deemed that those of ordinary skill in the art to which the present application pertains would be able to easily understand the process without repetitive description of the details.

The above description is merely illustrative of the technical spirit of the present application, and those of ordinary skill in the art to which the present application pertains should be able to make various modifications and changes within a scope not departing from essential characteristics of the present application. Therefore, the above-described embodiments of the present application may also be implemented separately or in combination.

The embodiments disclosed herein are for describing the technical spirit of the present application instead of limiting the same, and the scope of the technical spirit of the present application is not limited by such embodiments. The scope of the present application should be interpreted on the basis of the claims below, and all technical spirits within the equivalent scope should be interpreted as belonging to the scope of the present application.

The invention claimed is:

1. A polymerase chain reaction (PCR) method for performing a PCR of a target DNA within a sample, the PCR method comprising:
   placing a sample on a plate:
   contacting a first patch comprising a first reagent within a gel-type net-like structure forming micro-cavities to the plate on which the sample is placed to deliver a portion of the contained first reagent to the plate;
   adjusting a temperature of the sample to cause the PCR; and
   separating the first patch from the plate by spacing the first patch a predetermined distance or more apart from the plate to absorb a portion of the delivered first reagent that has not reacted with the target DNA in to the first patch,
   wherein the placing of the sample on the plate comprises smearing or printing a sample on the plate.

2. The PCR method of claim 1, wherein the placing of the sample on the plate further comprises fixing the sample onto the plate.

3. The PCR method of claim 1, wherein the adjusting the temperature of the sample comprises adjusting a temperature of the plate in order to adjust the temperature of the sample provided on the plate.

4. The PCR method of claim 3, wherein the separating the first patch from the plate further comprises separating the first patch from the plate when the temperature of the plate is higher than or equal to a reference temperature.

5. The PCR method of claim 2, further comprising contacting a second patch comprising a second reagent to the plate on which the sample is placed to deliver a portion of the contained second reagent to the plate, wherein the first reagent is different from the second reagent.

6. The PCR method of claim 5, wherein the first patch further comprises the second reagent.

7. The PCR method of claim 5, wherein the adjusting the temperature of the sample comprises at least one of adjusting a temperature of the first patch and adjusting a temperature of the second patch.

8. The PCR method of claim 7, wherein:
   the first reagent is delivered to the sample after the adjusting the temperature of the first patch; and
   the second reagent is delivered to the sample after the adjusting the temperature of the second patch.

9. The PCR method of claim 8, wherein:
   the first reagent comprises a first substance that reacts specifically with the target DNA, and
   the second reagent comprises a second substance that reacts with a DNA bound to the first substance.

* * * * *